US012419786B2

(12) United States Patent
George et al.

(10) Patent No.: US 12,419,786 B2
(45) Date of Patent: Sep. 23, 2025

(54) EXTERNAL EAR CANAL PRESSURE REGULATION SYSTEM

(71) Applicant: NOCIRA, LLC, Tempe, AZ (US)

(72) Inventors: David George, Scottsdale, AZ (US); George Buckler, Phoenix, AZ (US); David Brice Sullivan, Mechanicsburg, PA (US)

(73) Assignee: Nocira, LLC, Tempe, AZ (US)

( * ) Notice: Subject to any disclaimer, the term of this patent is extended or adjusted under 35 U.S.C. 154(b) by 0 days.

(21) Appl. No.: 17/407,503

(22) Filed: Aug. 20, 2021

(65) Prior Publication Data

US 2022/0226158 A1 Jul. 21, 2022

Related U.S. Application Data

(63) Continuation of application No. 14/980,226, filed on Dec. 28, 2015, now Pat. No. 11,096,828, which is a
(Continued)

(51) Int. Cl.
*A61F 11/12* (2006.01)
*A61H 9/00* (2006.01)
(Continued)

(52) U.S. Cl.
CPC ............ *A61F 11/12* (2013.01); *A61H 9/0071* (2013.01); *A61H 21/00* (2013.01); *A61H 23/02* (2013.01);
(Continued)

(58) Field of Classification Search
CPC ............ A61F 11/12; A61F 2250/0069; A61H 9/0071; A61H 21/00; A61H 23/02;
(Continued)

(56) References Cited

U.S. PATENT DOCUMENTS

| 787,443 A | 4/1905 | Godman et al. |
| 841,146 A | 1/1907 | Hasbrouck |

(Continued)

FOREIGN PATENT DOCUMENTS

| CA | 1136751 | 11/1982 |
| CA | 1222464 | 6/1987 |

(Continued)

OTHER PUBLICATIONS

Akerman, et al. Pearls and pitfalls in experimental in vivo models of migraine: Dural trigeminovascular nociception. Cephalalgia, 2013, 33 (8), pp. 557-592.
(Continued)

*Primary Examiner* — Rachel T Sippel
(74) *Attorney, Agent, or Firm* — Knobbe, Martens, Olson & Bear, LLP

(57) ABSTRACT

An external ear canal pressure regulation device including a fluid flow generator and an earpiece having a first axial earpiece conduit fluidically coupled to the fluid flow generator, whereby the earpiece has a compliant earpiece external surface configured to sealably engage an external ear canal as a barrier between an external ear canal pressure and an ambient pressure.

68 Claims, 27 Drawing Sheets

Related U.S. Application Data continuation of application No. 14/936,332, filed on Nov. 9, 2015, now Pat. No. 10,278,868, which is a continuation of application No. 14/702,428, filed on May 1, 2015, now Pat. No. 9,186,277, which is a continuation of application No. 14/316,668, filed on Jun. 26, 2014, now Pat. No. 9,039,639, which is a continuation-in-part of application No. 14/292,469, filed on May 30, 2014, now Pat. No. 10,251,790.

(60) Provisional application No. 61/983,865, filed on Apr. 24, 2014, provisional application No. 61/863,317, filed on Aug. 7, 2013, provisional application No. 61/841,111, filed on Jun. 28, 2013.

(51) Int. Cl.
*A61H 21/00* (2006.01)
*A61H 23/02* (2006.01)
*A61H 23/04* (2006.01)
*A61M 13/00* (2006.01)
*H04R 1/42* (2006.01)

(52) U.S. Cl.
CPC ........... *A61H 23/04* (2013.01); *A61M 13/003* (2013.01); *H04R 1/42* (2013.01); *A61F 2250/0069* (2013.01); *A61H 2201/0153* (2013.01); *A61H 2201/1207* (2013.01); *A61H 2201/5071* (2013.01); *A61H 2205/027* (2013.01); *A61M 2205/3344* (2013.01); *A61M 2205/362* (2013.01); *A61M 2210/0662* (2013.01)

(58) Field of Classification Search
CPC ........... A61H 23/04; A61H 2201/0153; A61H 2201/1207; A61H 2201/5071; A61H 2205/027; A61M 13/003; A61M 2205/3344; A61M 2205/362; A61M 2210/0662; H04R 1/42
See application file for complete search history.

(56) References Cited

U.S. PATENT DOCUMENTS

| | | | |
|---|---|---|---|
| 853,645 | A | 5/1907 | Meyer |
| 2,176,366 | A | 10/1939 | Smith |
| 2,437,490 | A | 3/1948 | Watson et al. |
| 2,570,675 | A | 10/1951 | Morris |
| 2,652,048 | A | 9/1953 | Joers |
| 3,757,769 | A | 9/1973 | Arguimbau et al. |
| 3,872,559 | A | 3/1975 | Leight |
| 4,002,161 | A | 1/1977 | Klar et al. |
| 4,133,984 | A | 1/1979 | Watson et al. |
| 4,160,449 | A | 7/1979 | Wade |
| 4,206,756 | A | 6/1980 | Grossan |
| 4,244,377 | A | 1/1981 | Grams |
| 4,289,143 | A | 9/1981 | Canavesio et al. |
| 4,325,386 | A | 4/1982 | Katz |
| 4,349,083 | A | 9/1982 | Bennett |
| 4,472,342 | A | 9/1984 | Carr |
| 4,552,137 | A | 11/1985 | Strauss |
| 4,594,058 | A | 6/1986 | Fischell |
| 4,632,104 | A | 12/1986 | Conrow |
| 4,667,676 | A | 5/1987 | Guinta |
| 4,688,582 | A | 8/1987 | Heller et al. |
| 4,754,748 | A | 7/1988 | Antowski |
| 4,757,807 | A | 7/1988 | Densert et al. |
| 4,775,370 | A | 10/1988 | Berry |
| 4,809,708 | A | 3/1989 | Geisler et al. |
| 4,896,380 | A | 1/1990 | Kamitani |
| 4,896,679 | A | 1/1990 | St. Pierre |
| 4,964,769 | A | 10/1990 | Hass |
| 4,984,579 | A | 1/1991 | Burgert et al. |
| 5,024,612 | A | 6/1991 | van den Honert et al. |
| 5,105,822 | A | 4/1992 | Stevens et al. |
| 5,131,411 | A | 7/1992 | Casali et al. |
| 5,228,431 | A | 7/1993 | Giarretto |
| 5,241,967 | A | 9/1993 | Yasushi et al. |
| 5,421,818 | A | 6/1995 | Arenberg |
| 5,431,636 | A | 7/1995 | Stangerup |
| 5,467,784 | A | 11/1995 | Mobley et al. |
| 5,476,446 | A | 12/1995 | Arenburg |
| 5,483,027 | A | 1/1996 | Krause |
| 5,483,975 | A | 1/1996 | Hirschebain |
| 5,488,961 | A | 2/1996 | Adams |
| 5,631,965 | A | 5/1997 | Chang et al. |
| 5,699,809 | A | 12/1997 | Combs et al. |
| 5,740,258 | A | 4/1998 | Goodwin-Johansson |
| 5,746,725 | A | 5/1998 | Shalon et al. |
| 5,755,234 | A | 5/1998 | Mobley et al. |
| 5,769,891 | A | 6/1998 | Clayton |
| 5,776,179 | A | 7/1998 | Ren et al. |
| 5,819,745 | A | 10/1998 | Mobley et al. |
| 5,865,183 | A | 2/1999 | Hirschebain |
| 5,868,682 | A | 2/1999 | Combe et al. |
| 5,944,711 | A | 8/1999 | Pender |
| 6,004,274 | A | 12/1999 | Nolan et al. |
| 6,016,499 | A | 1/2000 | Ferguson |
| 6,024,726 | A | 2/2000 | Hill |
| 6,129,174 | A | 10/2000 | Brown et al. |
| 6,139,507 | A | 10/2000 | Jeng |
| 6,159,171 | A | 12/2000 | Densert et al. |
| 6,186,959 | B1 | 2/2001 | Canfield et al. |
| 6,258,067 | B1 | 7/2001 | Hill |
| 6,296,652 | B1 | 10/2001 | Qingmin |
| 6,359,993 | B2 | 3/2002 | Birmhall |
| 6,430,443 | B1 | 8/2002 | Karell |
| 6,511,437 | B1 | 1/2003 | Nakamura et al. |
| 6,592,512 | B2 | 7/2003 | Stöckert et al. |
| 6,629,938 | B1 | 10/2003 | Engvall et al. |
| 6,725,568 | B2 | 4/2004 | Gronka |
| 6,748,275 | B2 | 6/2004 | Lattner et al. |
| 6,800,062 | B2 | 10/2004 | Epley |
| 6,820,717 | B2 | 11/2004 | Fleming et al. |
| 6,878,128 | B2 | 4/2005 | MacMahon et al. |
| 6,958,043 | B2 | 10/2005 | Hissong |
| 6,981,569 | B2 | 1/2006 | Stilp |
| 7,022,090 | B1 | 4/2006 | Engvall et al. |
| 7,162,039 | B1 | 1/2007 | Callahan |
| 7,179,238 | B2 | 2/2007 | Hissong |
| 7,189,252 | B2 | 3/2007 | Krueger |
| 7,268,466 | B2 | 9/2007 | Rasmussen |
| 7,352,871 | B1 | 4/2008 | Mozo |
| D570,457 | S | 6/2008 | Brown |
| 7,613,519 | B2 | 11/2009 | De Ridder |
| 7,766,858 | B2 | 8/2010 | Franz et al. |
| 7,779,844 | B2 | 8/2010 | Purcell et al. |
| 7,785,346 | B2 | 8/2010 | Blumberg |
| 7,797,042 | B2 | 9/2010 | Dietrich et al. |
| 7,833,282 | B2 | 11/2010 | Mandpe |
| 7,892,180 | B2 | 2/2011 | Epley |
| 7,959,597 | B2 | 6/2011 | Baker et al. |
| 7,988,657 | B2 | 8/2011 | Shapiro et al. |
| 8,020,563 | B2 | 9/2011 | Pfanstiehl |
| 8,047,207 | B2 | 11/2011 | Perez et al. |
| 8,052,693 | B2 | 11/2011 | Shahoian |
| 8,122,892 | B2 | 2/2012 | Johnson et al. |
| 8,142,373 | B1 | 3/2012 | Riles |
| 8,199,919 | B2 | 6/2012 | Goldstein et al. |
| 8,241,224 | B2 | 8/2012 | Keefe |
| 8,249,285 | B2 | 8/2012 | Killion et al. |
| 8,251,925 | B2 | 8/2012 | Keady et al. |
| 8,262,717 | B2 | 9/2012 | Rogers et al. |
| 8,267,983 | B2 | 9/2012 | Rogers et al. |
| 8,267,984 | B2 | 9/2012 | Rogers |
| 8,328,830 | B1 | 12/2012 | Pandit |
| 8,398,562 | B2 | 3/2013 | Keller |
| 8,414,521 | B2 | 4/2013 | Baker et al. |
| 8,442,632 | B2 | 5/2013 | Kullok et al. |
| 8,460,356 | B2 | 6/2013 | Rogers et al. |
| 8,506,469 | B2 | 8/2013 | Dietrich et al. |
| 8,515,552 | B2 | 8/2013 | Englehart |

(56) References Cited

U.S. PATENT DOCUMENTS

| | | | |
|---|---|---|---|
| 8,550,206 B2 | 10/2013 | Keady et al. | |
| 8,568,348 B2 | 10/2013 | Vlodaver | |
| 8,603,152 B2 | 12/2013 | Smith et al. | |
| 8,625,833 B1 | 1/2014 | Armwood | |
| 8,666,502 B2 | 3/2014 | Hartlep et al. | |
| 8,688,239 B2 | 4/2014 | Hartlep et al. | |
| 8,696,724 B2 | 4/2014 | Rogers | |
| 8,858,430 B2 | 10/2014 | Oyadiran et al. | |
| 8,963,914 B2 | 2/2015 | Rawat et al. | |
| 9,039,639 B2 | 5/2015 | George et al. | |
| 9,168,171 B2 | 10/2015 | Rogers | |
| 9,186,277 B2 | 11/2015 | George et al. | |
| 9,283,111 B2 | 3/2016 | Rogers et al. | |
| 9,526,653 B2 | 12/2016 | Rogers et al. | |
| 9,532,900 B2 | 1/2017 | Smith et al. | |
| 9,579,247 B2 | 2/2017 | Juto et al. | |
| 9,655,772 B2 | 5/2017 | Smith et al. | |
| 9,744,074 B2 | 8/2017 | Rogers | |
| 9,849,026 B2 | 12/2017 | Rogers et al. | |
| 10,076,464 B2 | 9/2018 | George et al. | |
| 10,251,790 B2 | 4/2019 | George et al. | |
| 10,271,992 B2 | 4/2019 | Hayahi et al. | |
| 10,278,868 B2 | 5/2019 | George et al. | |
| 10,319,475 B1* | 6/2019 | Croan | G06Q 50/26 |
| 10,376,695 B2 | 8/2019 | Ericco et al. | |
| 10,760,566 B2 | 9/2020 | George et al. | |
| 10,772,766 B2 | 9/2020 | Sullivan | |
| 11,065,444 B2 | 7/2021 | Ericco et al. | |
| 11,090,194 B2 | 8/2021 | George et al. | |
| 11,096,828 B2 | 8/2021 | George et al. | |
| 11,246,793 B2 | 2/2022 | George et al. | |
| 11,859,606 B2 | 1/2024 | George et al. | |
| 12,016,816 B2 | 6/2024 | George et al. | |
| 12,102,506 B2 | 10/2024 | Sullivan | |
| 12,178,966 B2 | 12/2024 | George et al. | |
| 2001/0025191 A1 | 9/2001 | Montgomery | |
| 2002/0069883 A1 | 6/2002 | Hirchenbain | |
| 2003/0105450 A1 | 6/2003 | Dimick | |
| 2003/0195588 A1 | 10/2003 | Fischell et al. | |
| 2003/0220536 A1 | 11/2003 | Hissong | |
| 2003/0220585 A1* | 11/2003 | Hissong | A61F 11/00 600/560 |
| 2004/0097839 A1 | 5/2004 | Epley | |
| 2004/0163882 A1 | 8/2004 | Fleming et al. | |
| 2004/0225178 A1* | 11/2004 | Kriewall | A61F 11/04 600/25 |
| 2005/0065585 A1 | 3/2005 | Salas | |
| 2005/0165460 A1 | 7/2005 | Erfan | |
| 2005/0209516 A1 | 9/2005 | Fraden | |
| 2005/0267388 A1 | 12/2005 | Hanna | |
| 2006/0100681 A1 | 5/2006 | Salas Carpizo | |
| 2006/0197412 A1 | 9/2006 | Rasmussen | |
| 2006/0253087 A1 | 11/2006 | Vlodaver et al. | |
| 2006/0272650 A1 | 12/2006 | Hoogenakker et al. | |
| 2007/0040454 A1 | 2/2007 | Freudenberger et al. | |
| 2007/0060948 A1* | 3/2007 | Franz | A61F 11/00 606/201 |
| 2007/0112279 A1 | 5/2007 | Iseberg et al. | |
| 2007/0250119 A1 | 10/2007 | Tyler et al. | |
| 2007/0299362 A1 | 12/2007 | Epley et al. | |
| 2008/0011308 A1 | 1/2008 | Fleming | |
| 2008/0154183 A1 | 6/2008 | Baker et al. | |
| 2008/0168775 A1 | 7/2008 | Windheim et al. | |
| 2008/0208100 A1 | 8/2008 | Wolff | |
| 2008/0212787 A1 | 9/2008 | Goldstein et al. | |
| 2008/0220092 A1 | 9/2008 | Dipierro | |
| 2008/0240942 A1 | 10/2008 | Heinrich et al. | |
| 2008/0249439 A1 | 10/2008 | Tracey et al. | |
| 2008/0264464 A1 | 10/2008 | Lee et al. | |
| 2009/0012420 A1 | 1/2009 | Keller | |
| 2009/0082831 A1 | 3/2009 | Paul et al. | |
| 2009/0173353 A1 | 7/2009 | Pursell et al. | |
| 2009/0182399 A1 | 7/2009 | Sylvestre | |
| 2009/0228103 A1 | 9/2009 | Clayton | |
| 2009/0293886 A1 | 12/2009 | Dedrick et al. | |
| 2010/0002897 A1 | 1/2010 | Keady | |
| 2010/0030131 A1 | 2/2010 | Morris et al. | |
| 2010/0071707 A1 | 3/2010 | Wohl | |
| 2010/0071708 A1 | 3/2010 | Lenhardt | |
| 2010/0113991 A1 | 5/2010 | Wu | |
| 2010/0179490 A1 | 7/2010 | Connelly et al. | |
| 2010/0198282 A1 | 8/2010 | Rogers | |
| 2010/0211142 A1 | 8/2010 | Rogers | |
| 2010/0322454 A1 | 12/2010 | Ambrose et al. | |
| 2011/0079227 A1 | 4/2011 | Turcot et al. | |
| 2011/0097141 A1 | 4/2011 | Browm | |
| 2011/0098551 A1 | 4/2011 | Zhang | |
| 2011/0130786 A1 | 6/2011 | Clayton et al. | |
| 2011/0172739 A1 | 7/2011 | Mann et al. | |
| 2011/0184341 A1 | 7/2011 | Baker et al. | |
| 2011/0224493 A1 | 9/2011 | Oyadiran et al. | |
| 2011/0245902 A1 | 10/2011 | Katz | |
| 2011/0301572 A1 | 12/2011 | Vlodaver et al. | |
| 2011/0313481 A1 | 12/2011 | De Vos | |
| 2012/0046607 A1 | 2/2012 | Syk | |
| 2012/0203309 A1 | 8/2012 | Englehart | |
| 2012/0265093 A1 | 10/2012 | Allen et al. | |
| 2012/0296268 A1 | 11/2012 | Vlodavaer et al. | |
| 2012/0302859 A1 | 11/2012 | Keefe | |
| 2012/0310077 A1 | 12/2012 | Rogers | |
| 2012/0310313 A1 | 12/2012 | Rogers et al. | |
| 2012/0318605 A1 | 12/2012 | Brown | |
| 2013/0123889 A1 | 5/2013 | Katz et al. | |
| 2013/0136285 A1 | 5/2013 | Naumann | |
| 2013/0152949 A1 | 6/2013 | Simon | |
| 2013/0177179 A1 | 7/2013 | Ambrose et al. | |
| 2013/0183173 A1 | 7/2013 | Kohli et al. | |
| 2013/0282070 A1 | 10/2013 | Cowan et al. | |
| 2013/0303953 A1 | 11/2013 | Lattner | |
| 2013/0304103 A1 | 11/2013 | Burres | |
| 2013/0310907 A1 | 11/2013 | Rogers et al. | |
| 2013/0324932 A1 | 12/2013 | Cogley | |
| 2013/0331823 A1 | 12/2013 | Askem et al. | |
| 2014/0069442 A1 | 3/2014 | Lewis et al. | |
| 2014/0088671 A1 | 3/2014 | Rogers et al. | |
| 2014/0243941 A1 | 8/2014 | Rogers et al. | |
| 2014/0249608 A1 | 9/2014 | Rogers | |
| 2014/0275827 A1 | 9/2014 | Gill et al. | |
| 2014/0309718 A1 | 10/2014 | Smith et al. | |
| 2014/0334652 A1 | 11/2014 | Gebert | |
| 2014/0344740 A1 | 11/2014 | Kaula et al. | |
| 2014/0365175 A1 | 12/2014 | Packer et al. | |
| 2015/0005661 A1 | 1/2015 | Trammell | |
| 2015/0141879 A1 | 5/2015 | Harper et al. | |
| 2015/0320591 A1 | 11/2015 | Smith et al. | |
| 2015/0320592 A1 | 11/2015 | Black et al. | |
| 2015/0324544 A1 | 11/2015 | Maslowski et al. | |
| 2015/0328413 A1* | 11/2015 | Cain | A61M 11/00 128/200.23 |
| 2015/0335466 A1 | 11/2015 | Schöggler | |
| 2015/0374538 A1 | 12/2015 | Rogers | |
| 2016/0067099 A1 | 3/2016 | Hayashi | |
| 2016/0166203 A1 | 6/2016 | Goldstein | |
| 2016/0279435 A1 | 9/2016 | Hyde et al. | |
| 2016/0346117 A1 | 12/2016 | Rogers et al. | |
| 2016/0378945 A1 | 12/2016 | Mian et al. | |
| 2017/0105876 A1 | 4/2017 | O'Connell, Sr. et al. | |
| 2017/0109988 A1 | 4/2017 | O'Connell, Sr. et al. | |
| 2017/0135854 A1 | 5/2017 | Rogers et al. | |
| 2017/0235889 A1 | 8/2017 | Main et al. | |
| 2018/0008457 A1 | 1/2018 | Smith et al. | |
| 2018/0106244 A1 | 4/2018 | Wang et al. | |
| 2018/0125748 A1 | 5/2018 | Goldenberg et al. | |
| 2020/0121544 A1 | 4/2020 | George et al. | |
| 2020/0222272 A1 | 7/2020 | George et al. | |
| 2021/0222684 A1 | 7/2021 | George et al. | |
| 2021/0228414 A1 | 7/2021 | George et al. | |
| 2021/0330928 A1 | 10/2021 | George et al. | |
| 2022/0202617 A1 | 6/2022 | George et al. | |

(56) References Cited

U.S. PATENT DOCUMENTS

| | | | |
|---|---|---|---|
| 2022/0370286 | A1 | 11/2022 | George et al. |
| 2024/0271609 | A1 | 8/2024 | George |

FOREIGN PATENT DOCUMENTS

| | | |
|---|---|---|
| CA | 1241152 | 8/1988 |
| CA | 2003452 | 6/1990 |
| CA | 2275057 | 10/1999 |
| CA | 2429560 | 1/2004 |
| CN | 2075517 U | 4/1991 |
| CN | 2418864 | 2/2001 |
| CN | 2530645 | 1/2003 |
| CN | 2721057 Y | 8/2005 |
| CN | 1791370 A | 6/2006 |
| CN | 2912525 | 6/2007 |
| CN | 200945215 Y | 9/2007 |
| CN | 201143258 | 11/2008 |
| CN | 201164541 | 12/2008 |
| CN | 101668497 | 3/2010 |
| CN | 201505220 U | 6/2010 |
| CN | 201524178 | 7/2010 |
| CN | 201558360 | 8/2010 |
| CN | 201870809 | 6/2011 |
| CN | 202036187 | 11/2011 |
| CN | 202185057 | 4/2012 |
| CN | 102484761 | 5/2012 |
| CN | 102551957 | 7/2012 |
| CN | 202313927 | 7/2012 |
| CN | 102647966 | 8/2012 |
| CN | 202477966 | 10/2012 |
| CN | 202505833 | 10/2012 |
| CN | 102892392 A | 1/2013 |
| CN | 102986250 | 3/2013 |
| DE | 37 83 917 T2 | 8/1993 |
| DE | 102011008802 | 7/2012 |
| EP | 0 026 247 | 4/1981 |
| EP | 0 400 900 | 12/1990 |
| EP | 1 027 863 | 8/2000 |
| EP | 2 207 366 | 7/2010 |
| EP | 2 990 017 | 3/2016 |
| FR | 2 605 516 A1 | 4/1988 |
| FR | 2 779 944 | 12/1999 |
| GB | 1432572 | 4/1976 |
| GB | 1522031 | 8/1978 |
| GB | 2054387 | 2/1981 |
| GB | 2185688 | 7/1987 |
| GB | 2343263 | 5/2000 |
| GB | 2479891 | 11/2011 |
| IT | 1214840 | 1/1990 |
| JP | S 57-188245 | 11/1982 |
| JP | H 02-220650 | 9/1990 |
| JP | H 07-111987 | 5/1995 |
| JP | H 11-514898 | 12/1999 |
| JP | 2002-519150 | 7/2002 |
| JP | 2003-018359 | 1/2003 |
| JP | 2006-345903 | 12/2006 |
| JP | 2009-022699 | 2/2009 |
| JP | 2010-233643 | 10/2010 |
| JP | 2010-535542 | 11/2010 |
| JP | 2011-217986 | 11/2011 |
| JP | 2012-526498 | 10/2012 |
| JP | 2013-068448 | 4/2013 |
| JP | 2013-102784 | 5/2013 |
| JP | 2020-44371 | 3/2020 |
| KR | 10-1273296 | 6/2013 |
| MX | PA03005598 | 10/2004 |
| MX | 2010014470 | 2/2011 |
| MX | 2011006854 | 8/2011 |
| MX | 2012007726 | 8/2012 |
| RU | 90 333 U1 | 1/2010 |
| WO | WO 1986/01399 | 3/1986 |
| WO | WO 1994/22372 | 10/1994 |
| WO | WO 1996/23293 | 8/1996 |
| WO | WO 1997/23178 | 7/1997 |
| WO | WO 2000/001331 | 1/2000 |
| WO | WO 2000/001346 | 1/2000 |
| WO | WO 2000/010484 | 3/2000 |
| WO | WO 2000/010627 | 3/2000 |
| WO | WO 2000/010848 | 3/2000 |
| WO | WO 2001/19244 | 3/2001 |
| WO | WO 2003/075761 | 9/2003 |
| WO | WO 2004/064672 | 8/2004 |
| WO | WO 2004/100844 | 11/2004 |
| WO | WO 2006/003910 | 1/2006 |
| WO | WO 2006/009545 | 1/2006 |
| WO | WO 2007/084674 | 7/2007 |
| WO | WO 2007/118092 | 10/2007 |
| WO | WO 2007/145853 | 12/2007 |
| WO | WO 2008/036368 | 3/2008 |
| WO | WO 2008/064230 | 5/2008 |
| WO | WO 2008/086187 | 7/2008 |
| WO | WO 2008/128173 | 10/2008 |
| WO | WO 2008/153588 | 12/2008 |
| WO | WO 2009/020862 | 2/2009 |
| WO | WO 2009/050306 | 4/2009 |
| WO | WO 2009/077902 | 6/2009 |
| WO | WO 2010/005899 | 1/2010 |
| WO | WO 2010/016925 | 2/2010 |
| WO | WO 2010/085196 | 7/2010 |
| WO | WO 2011/075573 | 6/2011 |
| WO | WO 2011/075574 | 6/2011 |
| WO | WO 2012/007193 | 1/2012 |
| WO | WO 2012/083098 | 6/2012 |
| WO | WO 2012/083102 | 6/2012 |
| WO | WO 2012/083106 | 6/2012 |
| WO | WO 2012/083126 | 6/2012 |
| WO | WO 2012/083151 | 6/2012 |
| WO | WO 2013/075255 | 5/2013 |
| WO | WO 2014/120947 | 8/2014 |
| WO | WO 2014/175257 | 10/2014 |
| WO | WO 2014/210457 | 12/2014 |
| WO | WO 2015/009421 | 1/2015 |
| WO | WO 2015/074060 | 5/2015 |
| WO | WO 2016/022761 | 2/2016 |
| WO | WO 2017/040739 | 3/2017 |
| WO | WO 2017/040741 | 3/2017 |
| WO | WO 2017/040747 | 3/2017 |
| WO | WO 2017/079783 | 5/2017 |
| WO | WO 2017/197150 | 11/2017 |
| WO | WO 2018/106839 | 6/2018 |
| WO | WO 2018/157143 | 8/2018 |
| WO | WO 2019/246456 | 12/2019 |

OTHER PUBLICATIONS

Baguley et al. Does caloric vestibular stimulation modulate tinnitus? Neuroscience Letters, Mar. 2011, 492(1), pp. 52-54.

Baier, et al.: "Vestibular-Evoked Myogenic Potentials In "Vestibular Migraine" and Meniere's Disease," Ann. N.Y. Acad. Sci., May 2009, 1164, pp. 324-327.

Becker: Weather and migraine: Can so many patients be wrong? Cephalalgia, Mar. 2011, 31(4), pp. 387-390.

Berthold Langguth, Verena Hund, Volker Busch, et al., "Tinnitus and Headache," BioMed Research International, vol. 2015, Article ID 797416, 7 pages, 2015. https://doi.org/10.115/2015/797416 (Year: 2015) in 7 pages.

Bolay et al.,: "Does Low Atmospheric Pressure Independently Trigger Migraine?" Headache, Oct. 2011, 51(9), pp. 1426-1430.

Breathometer. Breathometer—The World's First Smartphone Breathalyzer. Website, http://www.breathometer.com, originally downloaded Jun. 19, 2014, 8 total pages.

Cadwell. Sierra Wave. Website, http://www.cadwell.com, originally downloaded Feb. 27, 2014, 1 page.

Cathcart, et al., "Pain sensitivity mediates the relationship between stress and headache intensity in chronic tension-type headache", Nov. 2012 (Year: 2012) in 5 pages.

Cranial Nerves—Wikipedia, https://en.wikipedia.org/wiki/Cranial_nerves, printed Aug. 16, 2019 in 12 pages.

Croley, Christen, "Mechanicsburg doctor develops new migraine therapy," The Sentinel, Nov. 9, 2012.

(56) References Cited

OTHER PUBLICATIONS

DaSilva, et al.: "tdCS-Induced Analgesia and Electrical Fields in Pain-Related Neural Networks in Chronic Migraine," The Journal of Head and Face Pain, Sep. 2012, 52, pp. 1283-1295.
Dirckx et al. Human tympanic membrane deformation under static pressure. Hearing Research, Jan. 1991, 51(1), pp. 93-106.
Doherty, Colleen. "The Link Between Migraines and Tinnitus". Verywell Health, Nov. 23, 2019, https://www.verywellhealth.com/link-between-migraines-and-tinnitus-4077631#citation-10 (Year: 2019) in 4 pages.
Facebook. Zōk: The first migraine and headache solution, Webpage, https://www.facebook.com, originally downloaded May 18, 2017, 10 pages total.
Fasold et al. Human Vestibular Cortex as Identified with Caloric Stimulation in Functional Magnetic Resonance Imaging. Neuroimage, Nov. 2002, 17(3), pp. 1384-1393.
Ferrotec. Thermal Solutions. Website: http://thermal.ferrotec.com, originally downloaded Feb. 27, 2014, 1 page.
Ferrotec. Thermoelectric Technical Reference—Installation of Thermoelectric Modules. Website, http://thermal.ferrotec.com, originally downloaded May 21, 2014, 4 total pages.
Ferrotec. Thermoelectric Technical Reference—Introduction to Thermoelectric Cooling. Website, http://forrotec.com, originally downloaded Feb. 27, 2014, 2 total pages.
Frangos E, Ellrich J, Komisaruk B. Non-invasive access to the vagus nerve central projections via electrical stimulation of the external ear: fMRI evidence in humans. Brain Stimul. Dec. 6, 2014. 8(3), 624-636 in 13 pages.
George et al. Safety and usability factors in development of a novel, automated treatment device for acute migraine. Biomedical sciences instrumentation. Biomedical sciences instrumentation, Jan. 2017, 53, pp. 398-403.
Hahn: "Let Me Blow in Your Ear, for Migraine Treatment, Of Course," Smile Columbia Dentistry, https://www.tmjtreatments.com, originally downloaded Apr. 25, 2016, 2 pages total.
Hu et al. Burden of migraine in the United States: disability and economic costs. Arch. Intern. Med., Apr. 1999, 159, pp. 813-818.
Janetta Neurovascular Compress in Cranial Nerve and Systemic Disease. Ann Surg, Oct. 1980, 192 (4), pp. 518-524.
Job et al. Cortical Representation of Tympanic Membrane Movements due to Pressure Variation: An ±MRI Study Human Brain Mapping, May 2011, 32(5), pp. 744-749.
Kanzara T, Hall A, Virk J, Leung B, Singh A. Clinical anatomy of the tympanic nerve: A review. World J Otorhinolaryngol. Nov. 2014; 4(4), 17-22 in 8 pages.
Kickstarter. Zōk: The first headache product that solves migraines and headaches. Website, https://www.funded.today, originally downloaded May 18, 2017, 3 pages total.
Kiyokawa J., Yamaguchi K, Okada R, Maehara T, Akita K. Origin, course and distribution of the nerves to the posterosuperior wall of the external acoustic meatus. Anat Sci Int. Mar. 2014; 89(4), 238-245.
Klingner et al.: "Components of vestibular cortical function," Behavioral Brain Research, Jan. 2013, 236(1), pp. 194-199.
Kolev. How caloric vestibular irrigation influences migraine attacks. Cephalalgia. Aug. 1990, vol. 10 issue 4, pp. 167-169 (abstract only).
Lifting the Burden. The Global Campaign Against Headache. Website, http://www.l-t-b.org, originally downloaded Feb. 27, 2014, 1 page.
Liszewski: Ear Pressure Equalizer. Website, http://www.ohgizmo.com, originally downloaded Dec. 18, 2013, 1 page.
Long Island news12.com. Long Island Naturally: Migraines. Website video, http://longisland.news12.com/multimedia/long-island-naturally-migraines-1.6501113, Nov. 26, 2013, 3 total pages.
Mayr: The Origins of Feedback Control. M.I.T. Press, 1970.
McGeoch et al. Vestibular stimulation can relieve central pain of spinal origin. Spinal Cord, Nov. 2008, 46(11), pp. 756-757.
Medscape. Peripheral Nerve Stimulator—Train of Four Monitoring. Website, http://emedicine.medscape.com, originally downloaded Feb. 27, 2014, 2 total pages.
Medtronic. Meniett Device for Meniere's Disease. Meniett Low-Pressure Pulse Generator device. Website, http://www.medtronic.com, originally downloaded Feb. 27, 2014, 2 total pages.
Medtronic. Restore Life's Balance with Meniett Therapy. The Meniett Device for Meniere's Disease. On-line article, http://www.medtronic.com, originally downloaded Mar. 13, 2015, 2 total pages.
Meng et al. Migraine Prevention with a Supraorbital Transcutaneous Stimulator: A Randomized Controlled Trial. Neurology, Sep. 2013, 81, pp. 1102-1103.
Minen. Tinnitus and Headache. American Migraine Foundation, website, downloaded Feb. 8, 2017, 3 pages total.
Mosqueria et al. Vagus Nerve Stimulation in Patients with Migraine. Rev Neurol, 2013, 57(2), English Abstract.
Nagai et al. Encapsulated nerve corpuscles in the human tympanic membrane. Archives of Otorhinolaryngology, 1989, 246(3), pp. 169-172.
New York Health Solutions. Migraine Headaches. Website, http://www.nyhealthsolutions.com, originally downloaded May 23, 2014, 2 pages.
Nihashi et al. Representation of the ear in human primary somatosensory cortex. Neuroimage, Feb. 2001, 13(2), pp. 295-304 (abstract only).
Olesen et al. Emerging Migraine treatments and drug targets. Trends in Pharmacological Sciences, 2011, 32(6), pp. 352-359.
Pederson et al. Neurostimulation in cluster headache: A review of current progress. Cephalalgia, 2013, 33(14), pp. 1179-1193.
Pietrobon, Migraine: new molecular mechanism. Neuroscientist. Aug. 2005, vol. 11, Issue 4, pp. 373-386 (abstract only).
Porta-Etessam et al. Neuro-otological symptoms in patients with migraine. Neurologia, Mar. 2011, 26(2), pp. 100-104.
Ramachandran et al. Rapid Relief of Thalamic Pain Syndrome Induced by Vestibular Caloric Stimulation. Neurocase, Jun. 2007, 13(3), pp. 185-188.
Sakata et al. Air pressure-sensing ability of the middle ear—Investigation of sensing regions and appropriate measurement conditions. Auris Nasus Larynx, Aug. 2009, 36(4), pp. 393-399.
Sameiro-Barbosa et al. Sensory Entrainment Mechanisms in Auditory Perception: Neural Synchronization Cortico-Striatal Activation. Frontiers in Neuroscience, Aug. 2016, vol. 10, Article 361, 8 pages.
Saunders R, Tympanic membrane sensation. Brain. 1985, 108, 378-404 in 18 pages.
Schoenen et al. Migraine prevention with a supraorbital transcutaneous stimulator. Neurology, 2013, 80(8), pp. 697-704.
Schulman. Breath-Holding, Head Pressure, and Hot Water: An Effective Treatment for Migraine Headache. Headache, Nov.-Dec. 2002, 42(10), pp. 1048-1050.
Scion Neurostim. Therapeutic Neuromodulation via Caloric Vestibular Stimulation. Thermoneuromodulation (TNM). Slides for presentation, dated Sep. 2015, 12 pages total.
Sheftell, F, Steiner, TJ, Thhomas, H. Harry Potter and the Curse of Headache. Headache: The Journal of Head and Face Pain. Jun. 2007, vol. 47, Issue 6, pp. 911-916 (abstract only) in 1 page.
Shevel, "Headaches and tinnitus: correlation found", May 2008 (Year: 2006).
Silberstein et al.: "Botulinum Toxin Type A as a Migraine Preventive Treatment," The Journal of Head and Face Pain, Jun. 2000, 40, pp. 445-450.
Smartproducts. Series 100—Cartridge Specialty Check Valves and Pressure Relief Valves. Online catalog, www.smartproducts,com, originally downloaded Mar. 28, 2014, 2 total.
Stender, Dr., "Easing Migraine Symptoms with a Simple Puff of Air into the Ear," Pasadena Pain Management, http://www.pasadenapainmanagement.com, downloaded Apr. 25, 2016, 5 pages total.
Stovnver, LJ, et al. The global burden of headache: a documentation of headache prevalence and disability worldwide. Cephalalgia, 2007. vol. 27, pp. 193-210.
Sullivan: "Ear Insufflation As A Novel Therapy Which Produces Rapid Relief Of Migraine Headache—a Case Study," Funct Neurol Rehabil Egon 2013; vol. 3, Issue 1, pp. 93-107. Published on Jun. 7, 2013. Received on Jan. 2, 2013. Revised Jan. 28, 2013. Accepted Feb. 15, 2013.

(56) References Cited

OTHER PUBLICATIONS

Sullivan: "Ear Insufflation Produces Rapid and Significant Relief of Trigeminal Neuralgia," Funct Neurol Rehabil Egon 2013; vol. 3, Issue 4, pp. 1-6. Published on May 26, 2014. Received on Jun. 21, 2013. Revised Dec. 24, 2013. Accepted Jan. 12, 2014.
Tekdemir I, Aslan A, Elhan A., A clinico-anatomic study of the auricular branch of the vagus nerve and Arnold's ear-cough reflex. Surg Radiol Anat. 1998. 20(4), 253-257 in 5 pages.
Tekdemir I, Aslan A, Tuccar E, He C, Elhan A, Deda H. An anatomical study of the tympanic branch of the glossopharyngeal nerve (nerve of Jacobson). Ann Anat. Aug. 1998; 180(4): 349-52 in 4 pages.
Transcript of News Story, Aug. 22, 2013, video available at: https://www.facebook.com/178787878873891/videos/10201196245541704/.
"New Migraine Therapy," Aug. 22, 2013, video available at https://www.facebook.com/178787878873891/videos/10201196245541704/.
Transcript of News Story, Nov. 13, 2013, video available at: https://www.facebook.com/178787878873891/videos/treatment-for-migraines-and-trigeminal-neuralgia/10201781732138503/.
"Revolutionary Pain Therapy," Nov. 13, 2013, video available at https://www.facebook.com/178787878873891/videos/treatment-for-migraines-and-trigeminal-neuralgia/10201781732138503/.
Transcript of News Story, Jul. 7, 2014, video available at: https://www.facebook.com/178787878873891/videos/681870651898942/.
"New Therapy for Migraines," Jul. 7, 2014, video available at https://www.facebook.com/178787878873891/videos/treatment-for-migraines-and-trigeminal-neuralgia/10201781732138503/.
Transcript of Webinar, Apr. 10, 2013, video available at: https://www.anymeeting.com/WebConference/RecordingDefault.aspx?c_psrid=ED57DC868548.
"A novel application to resolve migraine headaches—A Functional Neurology forum," Apr. 10, 2013, video available at: https://www.anymeeting.com/WebConference/RecordingDefault.aspx?c_psrid=ED57DC868548.
Ultimate Ears. Ultimate Ears Custom In-Ear Monitors. Website, http://pro.ultimateears.com, originally downloaded Feb. 27, 2014, 3 total pages.
Von Korff, et al., "Assessing headaches severity. New Directions", Jul. 1994 (Year: 1994).
Westone. Occupational Earpieces. Website, http://www.westone.com, originally downloaded Feb. 27, 2014, 2 total pages.
Widemar L, Hellstrom S, Schultzberg M, Stenfors LE. Autonomic innervation of the tympanic membrane. An immunocytochemical and histofluorescence study. Acta Otolaryngol. Jul.-Aug. 1985;100(1-2):58:65 in 9 pages.
Wikipedia. Microcurrent electrical neuromuscular stimulator. Website, http://en.wikipedia.org, originally downloaded Feb. 27, 2014, 3 total pages.
Wikipedia. Somatosensory evoked potential. Website, http://en.wikipedia.org, originally downloaded Feb. 27, 2014, 5 pages total.
Wikipedia. Transcutaneous electrical nerve stimulation. Website, http://en.wikipedia.org, originally downloaded Feb. 27, 2014, 5 pages total.
World Health Organization. Headache disorders. Website, http://www.who.int, originally downloaded Feb. 27, 2014, 4 total pages.
Chinese Patent Application No. 201480042665.7; Office Action dated Jan. 22, 2017, 26 pages total.
Chinese Office Action, dated Sep. 4, 2017, re CN Application No. 201480042665.7, 6 pages total.
European Extended Search Report, dated Dec. 8, 2016, re EP Application No. 14816984.0, 9 pages total.
European Office Action, dated Nov. 24, 2017, re EP Application No. 14816984.0, 6 pages total.
International Search Report and Written Opinion in co-pending application No. PCT/US2018/019981, mailed Jun. 27, 2018 in 15 pages.
New Zealand Patent Application No. 713887; Office Action mailed Jul. 13, 2016, 9 pages total.
New Zealand Patent Application No. 713887; Office Action mailed Jul. 3, 2017, 9 pages total.
New Zealand Patent Application No. 713887; Office Action mailed Feb. 20, 2017, 9 pages total.
New Zealand Patent Application No. 713887; Office Action mailed Jun. 7, 2017, 9 pages total.
PCT International Patent Cooperation Treaty Patent Application No. PCT/US14/044159, filed Jun. 25, 2014.
PCT International Patent Application No. PCT/US2014/0066191; Written Opinion of the International Searching Authority mailed Feb. 26, 2015, 7 pages total.
U.S. Appl. No. 61/841,111, filed Jun. 28, 2013.
U.S. Appl. No. 14/292,469, filed May 30, 2014.
U.S. Appl. No. 14/936,332, filed Nov. 9, 2015.
U.S. Appl. No. 61/863,317, filed Aug. 7, 2013.
U.S. Appl. No. 61/905,616, filed Nov. 18, 2013.
U.S. Appl. No. 61/983,865, filed Apr. 24, 2014.
Teixido, Michael: "Migraine—More than a Headache," Dec. 15, 1999, ENT and Allergy of Delaware (Year: 1999).

\* cited by examiner

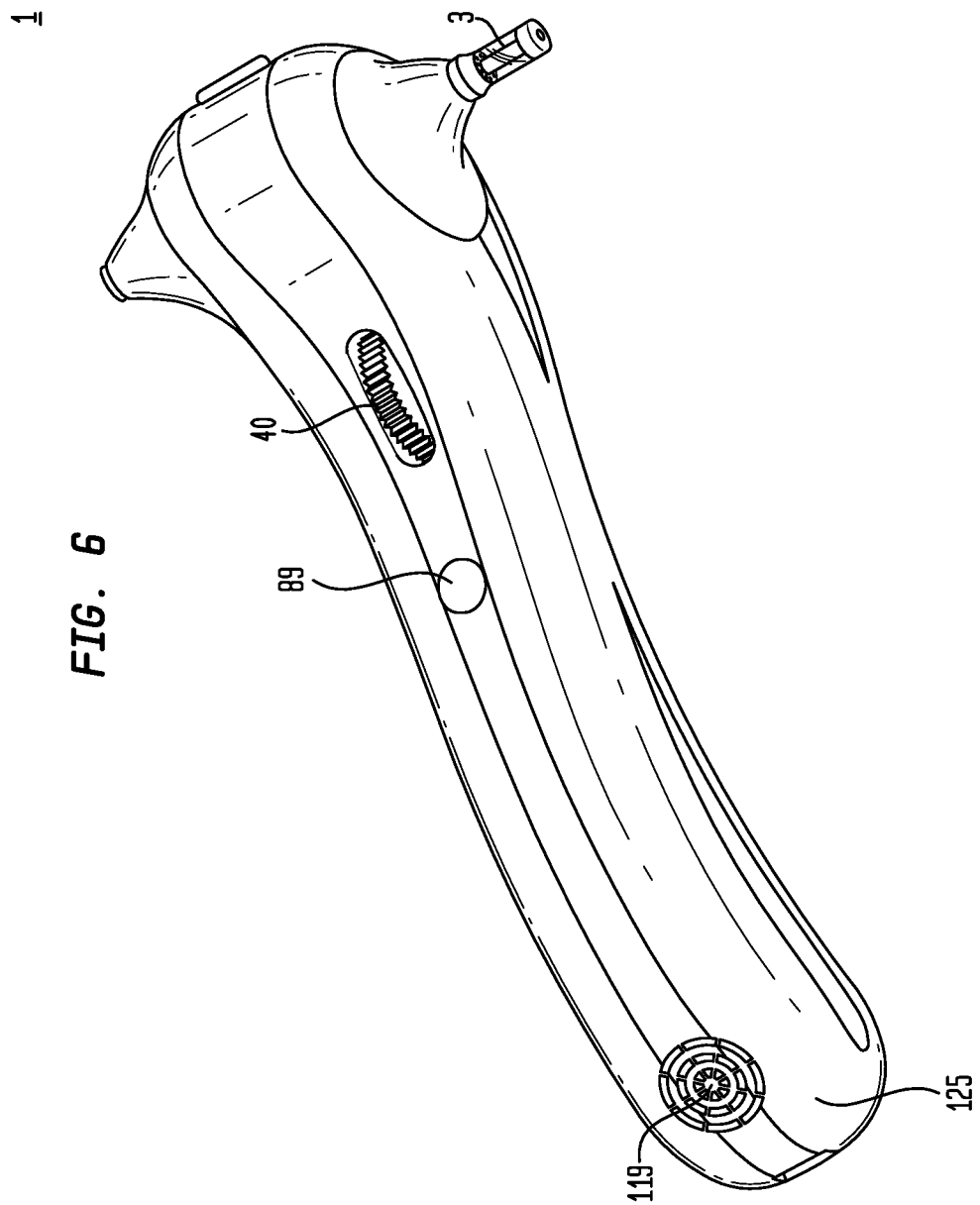

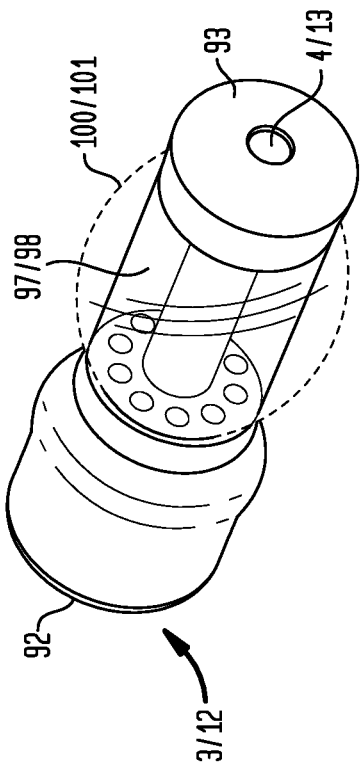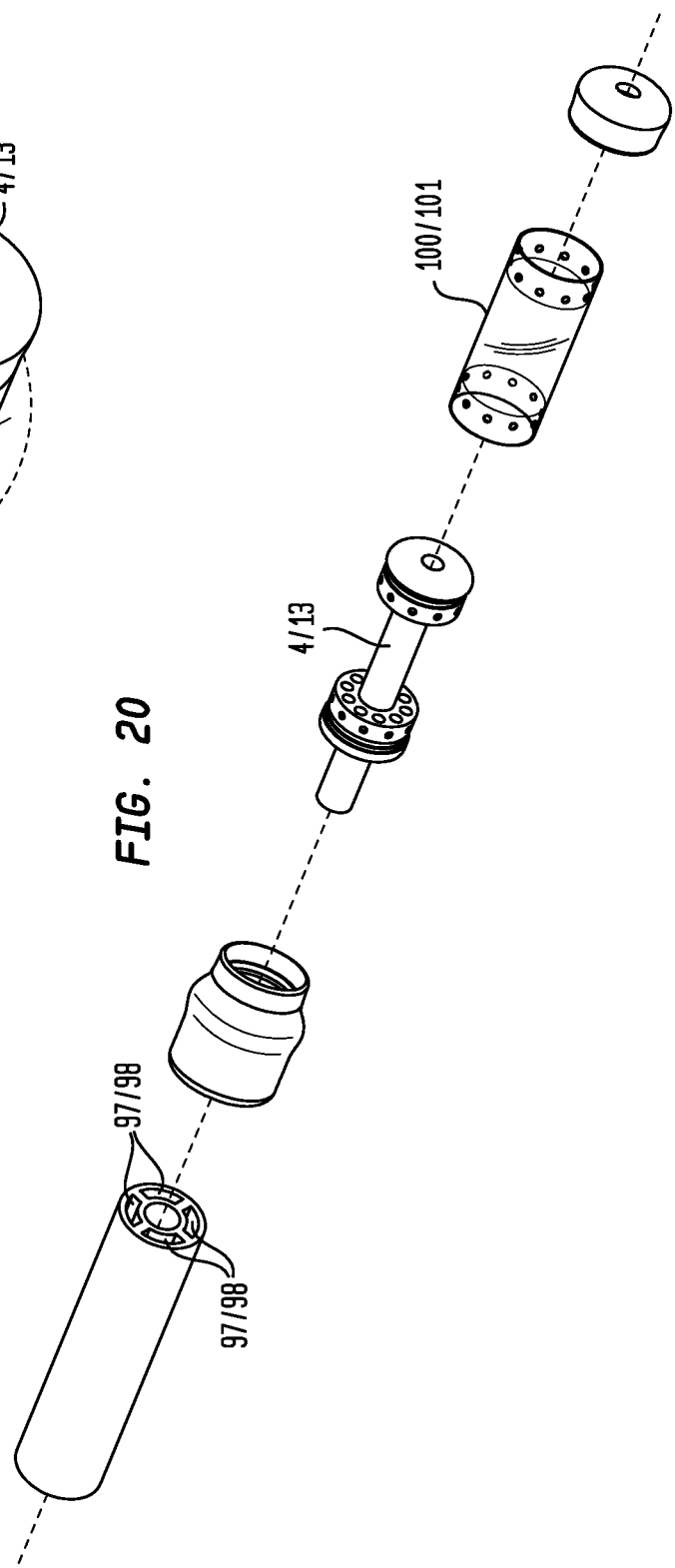

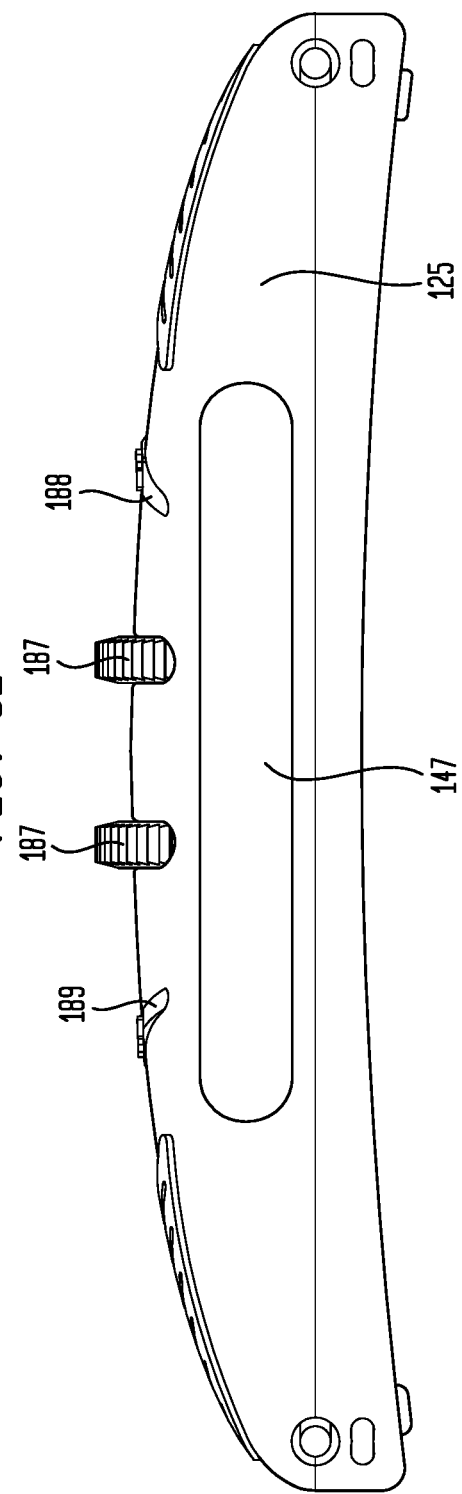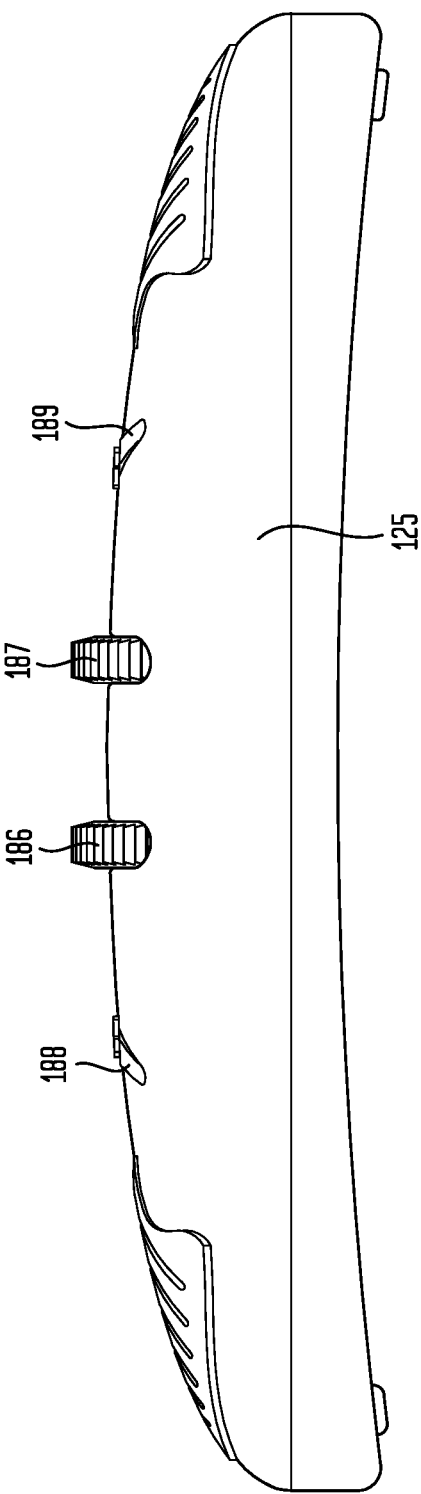

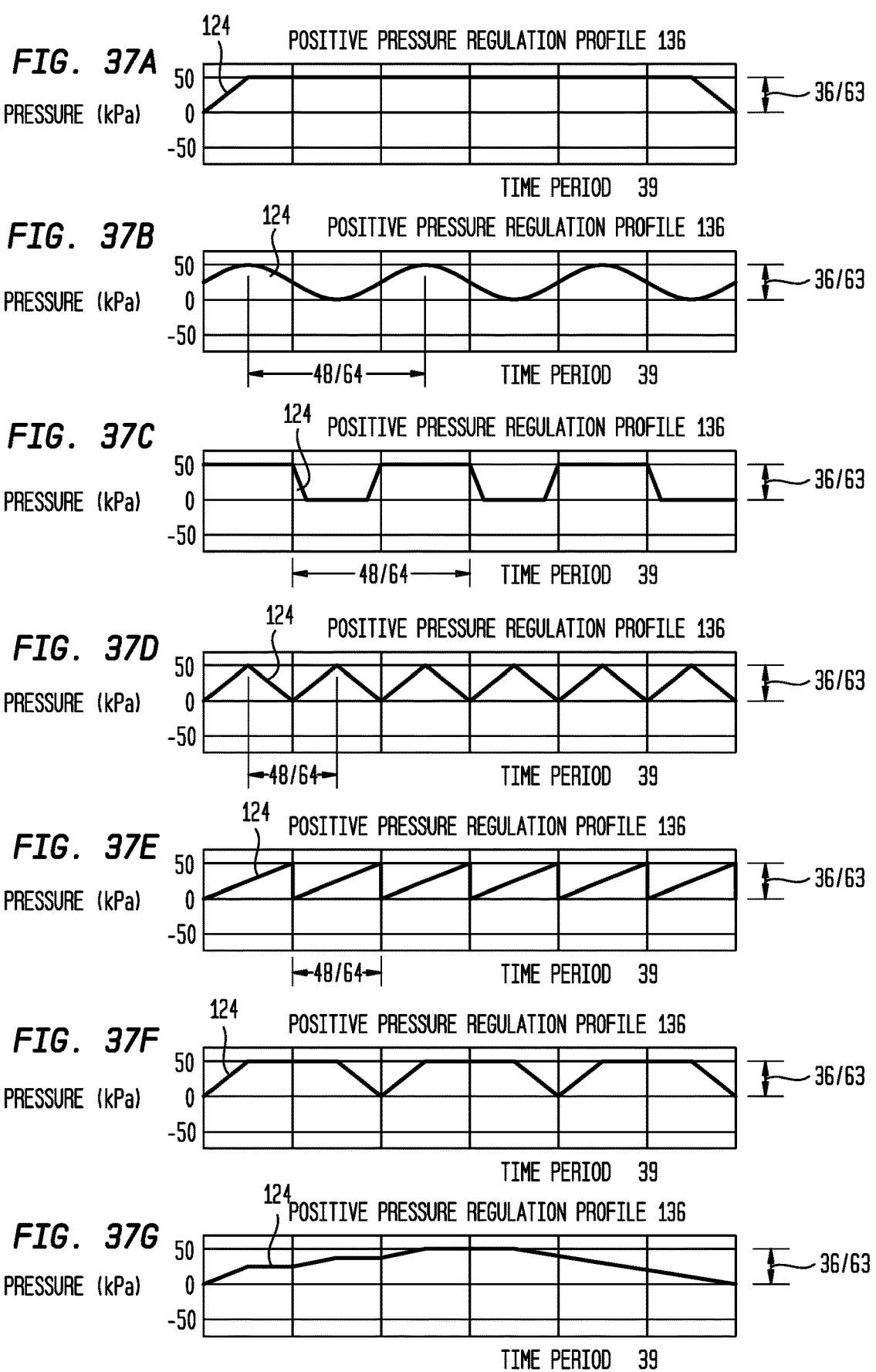

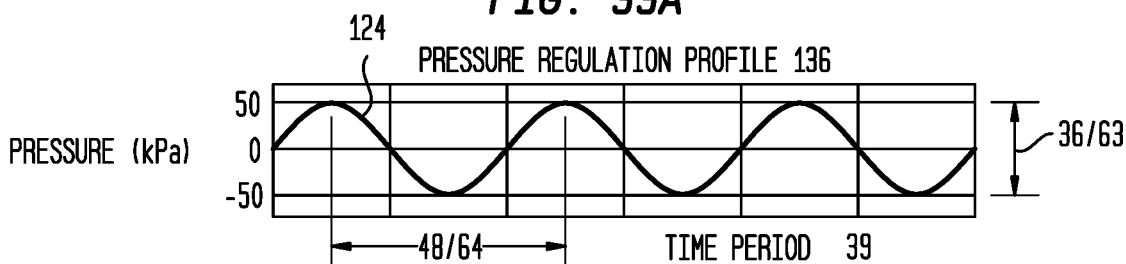
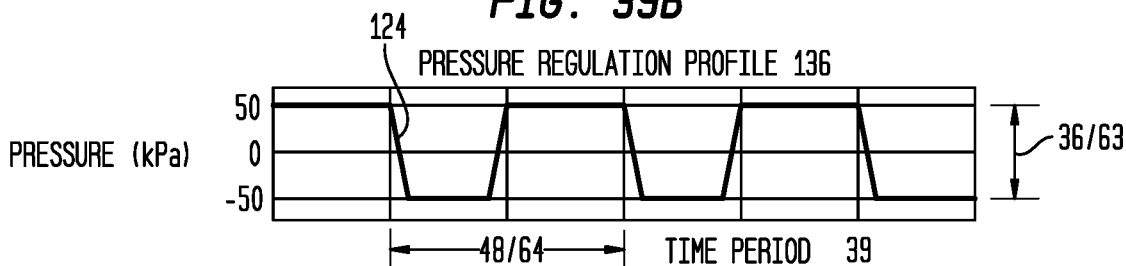
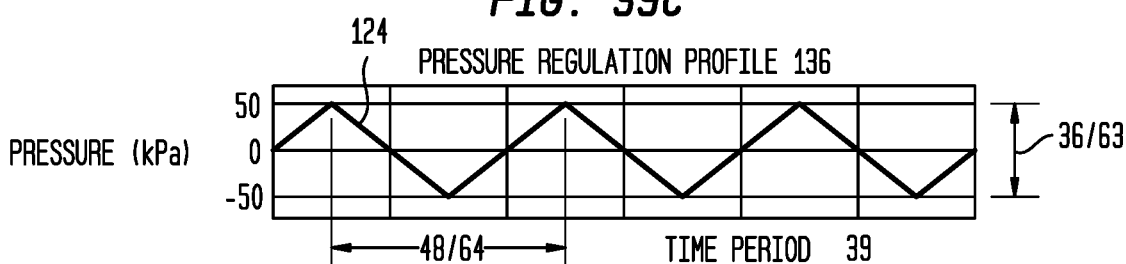
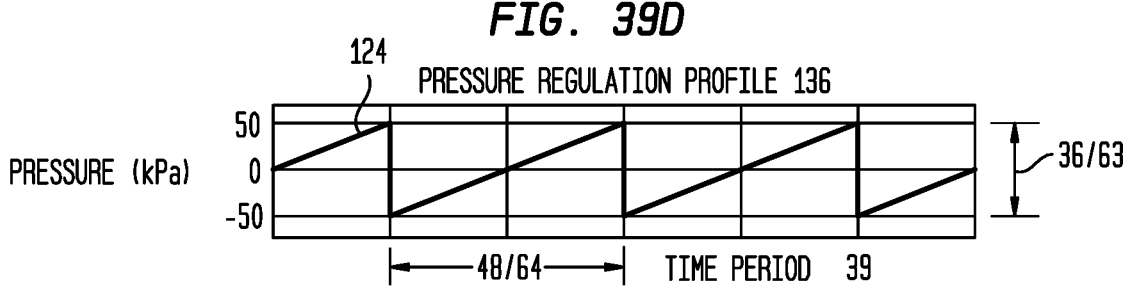
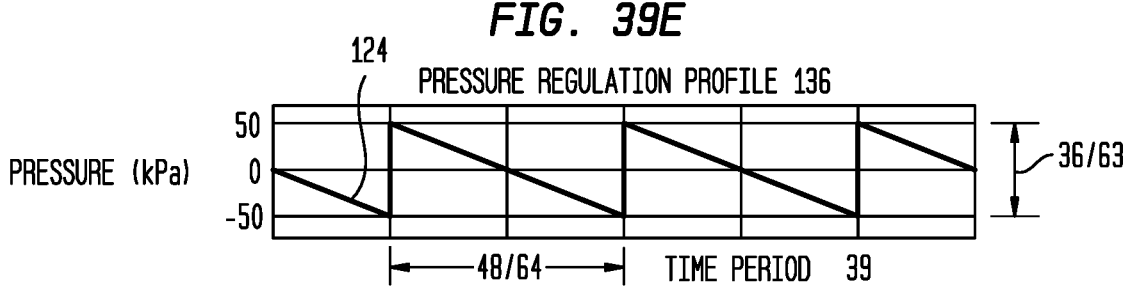

FIG. 40

| MODE | OPEN | CLOSED |
|---|---|---|
| INSUFFLATE L & R | V1-V2-V3L-V3R-V4-V5 | V6-IL-IR |
| INSUFFLATE L ONLY | V1-V3L-V4 | V2-V3R-V5-V6-IL-IR |
| INSUFFLATE R ONLY | V2-V3R-V5 | V1-V3L-V4-V6-IL-IR |
| INSUFFLATE L & IRRIGATE R | V1-V3L-V3R-V4-IR | V2-V5-V6-IL |
| INSUFFLATE R & IRRIGATE L | V2-V3R-V3L-V5-IL | V1-V4-V6-IR |
| IRRIGATE L & R | V3L-V3R-IL-IR-V6 | V1-V2-V4-V5 |
| IRRIGATE L ONLY | V3L-IL-V6 | V1-V2-V3R-V4-V5-IR |
| IRRIGATE R ONLY | V3R-IR-V6 | V1-V2-V3L-V4-V5-IL |
| EMERGENCY DEFLATION | V6 | V1-V2-V3L-V3R-V4-V5-IL-IR |

EXTERNAL EAR CANAL PRESSURE REGULATION SYSTEM

This United States Non-Provisional Patent Application is a continuation of U.S. Non-Provisional patent application Ser. No. 14/980,226, filed Dec. 28, 2015, now U.S. Pat. No. 11,096,828, issued on Aug. 24, 2021, which is a continuation of U.S. Non-Provisional patent application Ser. No. 14/936, 332, filed Nov. 9, 2015, now U.S. Pat. No. 10,278,868, issued on May 7, 2019, which is a continuation of U.S. Non-Provisional patent application Ser. No. 14/702,428, filed May 1, 2015, now U.S. Pat. No. 9,186,277, issued on Nov. 17, 2015, which is a continuation of U.S. Non-Provisional patent application Ser. No. 14/316,668, filed Jun. 26, 2014, now U.S. Pat. No. 9,039,639, issued on May 26, 2015, which is a continuation-in-part of U.S. Non-Provisional patent application Ser. No. 14/292,469, filed May 30, 2014, now U.S. Pat. No. 10,251,790, issued on Apr. 9, 2019, which claims the benefit of each of U.S. Provisional Patent Application No. 61/983,865, filed Apr. 24, 2014; U.S. Provisional Patent Application No. 61/863,317, filed Aug. 7, 2013, and U.S. Provisional Patent Application No. 61/841, 111, filed Jun. 28, 2013, each of which is hereby incorporated by reference herein.

I. BACKGROUND OF THE INVENTION

Pain or discomfort associated with a disorder, including neurologically-mediated disorders such as craniofacial pain syndromes or headache syndromes, may negatively impact the quality of life of the sufferer. In addition to the burden upon the individual, chronic neurological conditions may be a significant strain upon family members, employers, and the healthcare system.

Regarding migraine headaches, concomitant symptoms such as pain, nausea, aura, photophobia, dysesthesias, dizziness, vertigo, and dysequilibrium may represent a significant burden to the population. Epidemiological studies indicate that, in the United States, approximately 18% of women and 6% of men experience frequent migraine headaches and 2% of the general population suffer from chronic migraine headaches. Additionally, persons suffering with chronic migraine headaches or other headaches of similar severity and disability may be at a significantly greater risk for depression and attempted suicide. Thus, it is prudent for clinicians and researchers to continue searching for effective devices and methods to alleviate the symptoms associated with these disorders or to treat the disorders.

Standard pharmaceutical therapies for migraine headaches may generally be prescribed to prevent pain or to relieve pain. The various agents which fall under these two broad categories may exhibit a wide range of effectiveness and also incur varying degrees of side effects. From the perspective of economics, the expense of these medications may be a major source of financial burden on the consumer. Moreover, advanced interventions such as botulinum toxin injections, nerve blockades, neurosurgical alterations, and implanted electrical stimulators may significantly increase costs associated with treatment, while subjecting patients to potential changes in their anatomy and physiology, with no guarantee of complete or permanent symptomatic relief or disorder resolution.

There is a burgeoning field of understanding and applications within the neurosciences which seek to affect positive physiological changes in the nervous system through non-pharmaceutical and non-surgical applications. This field of 'functional neurology' views the human nervous system as a receptor driven system, which may be activated and stimulated in specific ways to produce adaptive, long-term changes through the process of neuroplasticity.

This approach to neurorehabilitation utilizes, but not necessarily exclusively includes, various forms and patterns of receptor activation or deactivation to promote positive neurophysiological adaptations within the central nervous system, including the brain, brainstem, and spinal cord, which may promote physiological function of associated tissues, organs, and systems.

There would be a substantial advantage in providing a device or methods which can generate one or more stimuli which can alleviate one or more symptoms associated with a disorder, such as craniofacial pain syndromes or headache syndromes, or treat one or more disorders.

II. SUMMARY OF THE INVENTION

A broad object of particular embodiments of the invention can be to provide an external ear canal pressure regulation device including a fluid flow generator capable of generating a fluid flow and an earpiece having an axial earpiece conduit which communicates between an earpiece first end and an earpiece second end, the axial earpiece conduit fluidicly coupled to the fluid flow generator, the earpiece having a complaint earpiece external surface configured to sealably engage an external ear canal of an ear as a barrier between an external ear canal pressure and an ambient pressure.

Another broad object of particular embodiments of the invention can be to provide an external ear canal pressure regulation device having the fluid flow generator capable of generating a pressure differential between the external ear canal and the ambient pressure.

Another broad object of particular embodiments of the invention can be to provide an external ear canal pressure regulation device having the fluid flow generator capable of generating a pressure differential amplitude oscillation which reciprocally drives the fluid flow between a fluid flow first direction and a fluid flow second direction in the axial earpiece conduit.

Another broad object of particular embodiments of the invention can be to provide an external ear canal pressure regulation device including a fluid flow temperature regulator fluidicly coupled between the fluid flow generator and the axial earpiece conduit, the fluid flow temperature regulator operable to regulate a fluid flow temperature of the fluid flow.

Another broad object of particular embodiments of the invention can be to provide an external ear canal pressure regulation device including a fluid flow generator capable of generating a fluid flow and a plurality of earpieces, each having an axial earpiece conduit which communicates between an earpiece first end and an earpiece second end, each axial earpiece conduit fluidicly coupled to the fluid flow generator, each earpiece having a complaint earpiece external surface configured to sealably engage an external ear canal of an ear as a barrier between an external ear canal pressure and an ambient pressure.

Another broad object of particular embodiments of the invention can be to provide an external ear canal pressure regulation device including a plurality of fluid flow generators capable of generating a corresponding plurality of fluid flows and a plurality of earpieces, each having an axial earpiece conduit which communicates between an earpiece first end and an earpiece second end, each axial earpiece conduit fluidicly coupled to a fluid flow generator, each earpiece having a complaint earpiece external surface configured to sealably engage an external ear canal of an ear as a barrier between an external ear canal pressure and an ambient pressure.

Another broad object of particular embodiments of the invention can be to provide an external ear canal pressure regulation device including a memory element and a processor in communication with the memory element, the memory element containing a computer code executable to regulate operation of one or more fluid flow generators.

Another broad object of particular embodiments of the invention can be to provide an external ear canal pressure regulation device having computer code executable to provide a transceiver controller which communicates with a transceiver capable of wireless connection with a controller device discrete from the external ear canal pressure regulation device.

Naturally, further objects of the invention are disclosed throughout other areas of the specification, drawings, and claims. In some embodiments, the device can depict on a display surface a graphical user interface, including a symptom ranking element, depicted prior to and subsequent to administration of one of a plurality of treatment profiles, which by user interaction allows entry of a symptom rank value.

III. BRIEF DESCRIPTION OF THE DRAWINGS

FIG. 6 is a perspective view of a particular embodiment of an external ear canal pressure regulation device.

FIG. 19 is a perspective view of a particular embodiment of an earpiece of an external ear canal pressure regulation device.

FIG. 20 is an exploded view of the particular embodiment of the earpiece of the external ear canal pressure regulation device shown in FIG. 18.

FIG. 32 is a first side view of a particular embodiment of an external ear canal pressure regulation device.

FIG. 33 is a second side view of a particular embodiment of an external ear canal pressure regulation device.

FIG. 37A is a positive pressure regulation profile which can be generated by a particular embodiment of an external ear canal pressure regulation device.

FIG. 37B is a positive pressure regulation profile which can be generated by a particular embodiment of an external ear canal pressure regulation device.

FIG. 37C is a positive pressure regulation profile which can be generated by a particular embodiment of an external ear canal pressure regulation device.

FIG. 37D is a positive pressure regulation profile which can be generated by a particular embodiment of an external ear canal pressure regulation device.

FIG. 37E is a positive pressure regulation profile which can be generated by a particular embodiment of an external ear canal pressure regulation device.

FIG. 37F is a positive pressure regulation profile which can be generated by a particular embodiment of an external ear canal pressure regulation device.

FIG. 37G is a positive pressure regulation profile which can be generated by a particular embodiment of an external ear canal pressure regulation device.

FIG. 39A is a pressure regulation profile which can be generated by a particular embodiment of an external ear canal pressure regulation device.

FIG. 39B is a pressure regulation profile which can be generated by a particular embodiment of an external ear canal pressure regulation device.

FIG. 39C is a pressure regulation profile which can be generated by a particular embodiment of an external ear canal pressure regulation device.

FIG. 39D is a pressure regulation profile which can be generated by a particular embodiment of an external ear canal pressure regulation device.

FIG. 39E is a pressure regulation profile which can be generated by a particular embodiment of an external ear canal pressure regulation device.

FIG. 40 is a valve position schedule for the particular embodiment of the invention shown in FIG. 28.

IV. DETAILED DESCRIPTION OF THE INVENTION

Figure 1:
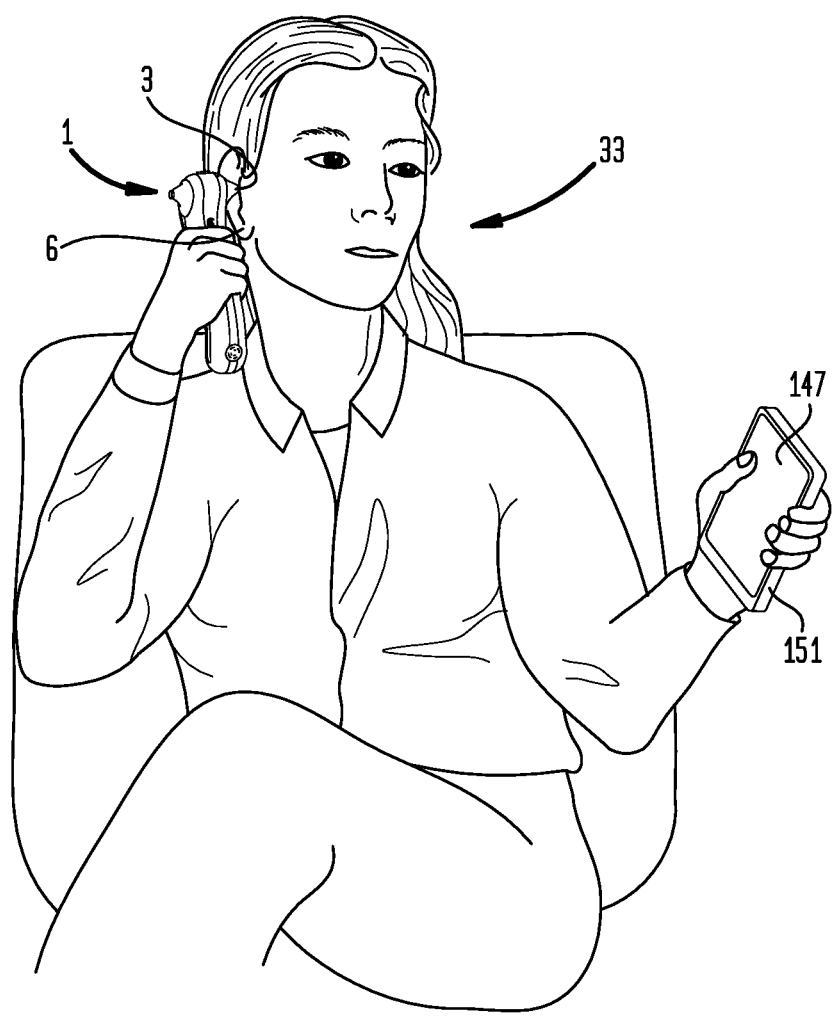
FIG. 1 is an illustration of a method of using a particular embodiment of the external ear canal pressure regulation device.

Now referring primarily to FIG. 1, FIG. 4, FIG. 5A, and FIG. 8, which illustrate a particular method of using an external ear canal pressure regulation device (1) including a first fluid flow generator (2) and a first earpiece (3) having a first axial earpiece conduit (4) fluidicly coupled to the first fluid flow generator (2). A particular method of use can include sealably engaging a first external ear canal (5) of a first ear (6) with a first earpiece external surface (7) of the first earpiece (3), generating a first fluid flow (8) between the first fluid flow generator (2) and the first axial earpiece conduit (4), and regulating a first pressure differential (9) between a first external ear canal pressure (10) of a first ear (6) and an ambient pressure (11). The first pressure differential (9) can be effective to alleviate one or more disorder symptoms or to treat one or more disorders.

Now referring primarily to FIG. 2, FIG. 5A, FIG. 5B, and FIG. 8, which illustrate a particular method of using an external ear canal pressure regulation device (1) including a first fluid flow generator (2), a first earpiece (3), and a second earpiece (12), each of the first and second earpieces (3)(12) having corresponding first and second axial earpiece conduits (4)(13) fluidicly coupled to the first fluid flow generator (2). The method of use can include sealably engaging a first external ear canal (5) of a first ear (6) with a first earpiece external surface (7) of the first earpiece (3), sealably engaging a second external ear canal (14) of a second ear (15) with a second earpiece external surface (16) of the second earpiece (12), generating a first fluid flow (8) between the first fluid flow generator (2) and the first and second axial earpiece conduits (4)(13), regulating a first pressure differential (9) between a first external ear canal pressure (10) of the first ear (6) and an ambient pressure (11), and regulating a second pressure differential (17) between a second external ear canal pressure (18) of the second ear (15) and an ambient pressure (11) effective to alleviate one or more disorder symptoms or treat one or more disorders.

Now referring primarily to FIG. 3, FIG. 5A, FIG. 5B, and FIG. 28, which illustrate a particular method of using an external ear canal pressure regulation device (1) including a first fluid flow generator (2), a first earpiece (3) having a first axial earpiece conduit (4) fluidicly coupled to the first fluid flow generator (2), a second fluid flow generator (19), and a second earpiece (12) having a second axial earpiece conduit (13) fluidicly coupled to the second fluid flow generator (19). The method of use can include sealably engaging a first external ear canal (5) of a first ear (6) with a first earpiece external surface (7) of the first earpiece (3), sealably engaging a second external ear canal (14) of the second ear (15) with a second earpiece external surface (16) of the second earpiece (12), generating a first fluid flow (8) between the first fluid flow generator (2) and the first axial earpiece conduit (4), regulating a first pressure differential (9) between a first external ear canal pressure (10) of the first ear (6) and an ambient pressure (11), generating a second fluid flow (20) between the second fluid flow generator (19) and the second axial earpiece conduit (13), and regulating a second pressure differential (17) between a second external ear canal pressure (8) of the second ear (15) and the ambient pressure (11) effective to alleviate one or more disorder symptoms or treat one or more disorders.

The term "pressure differential" for the purposes of this invention means the difference in pressure between two locations.

The term "pressure differential amplitude" for the purposes of this invention means the numerical value of the difference in pressure between two locations. The pressure differential amplitude can be expressed as a number without a sign (positive or negative), regardless of whether the pressure is lesser or greater in the first location relative to the second location. As an illustrative example, a first or second external ear canal pressure (10)(18) of +50 kilopascals above the ambient pressure (11) and a first or second external ear canal pressure (10)(18) of −50 kilopascals below the ambient pressure (11) can both have a first or second pressure differential amplitude (9)(17) of 50 kilopascals.

The term "external ear canal pressure" for the purposes of this invention means forces exerted within the first or second external ear canal (5)(14) and, without limitation to the breadth of the foregoing, means forces exerted within the first or second external ear canal (5)(14) by a fluid volume (21), a pre-selected fluid volume (22) of a first or second fluid flow (8)(20) delivered to or generated in the first or second external ear canal (5)(14) by operation of the external ear canal pressure regulation device (1).

The term "pre-selected" for the purposes of this invention means a parameter which has been prior selected for delivery to, generation in, or administration to the first or second external ear canal (5)(14) by interaction with the external ear canal pressure regulation device (1) and subsequently delivered to, generated in, or administered to a first or second external ear canal (5)(14) by operation of the external ear canal pressure regulation device (1). For example, a pre-selected fluid volume (22) of 10 milliliters can be prior selected for delivery to the first or second external ear canal (5)(14) by interaction with the external ear canal pressure regulation device (1) and subsequently, a fluid volume (21) of 10 milliliters can be delivered to the first or second external ear canal (5)(14) by operation of the external ear canal pressure regulation device (1).

The term "ambient pressure" for the purposes of this invention means forces exerted external to the first or second external ear canal (5)(14) in the ambient environment and, without limitation to the breadth of the foregoing, means forces exerted on a first or second earpiece (3)(12) on the ambient side of the corresponding first or second barrier (102)(103) created by having the corresponding first or second earpiece external surface (7)(16) sealably engaged with the corresponding first or second external ear canal (5)(14), as herein described.

The term "sealably engaged" for the purposes of this invention means a seal between an earpiece external surface and an external ear canal capable of maintaining a pressure differential, a pressure differential amplitude, or pre-selected pressure differential amplitude over a time period or a pre-selected time period, or pressure regulation profile effective to alleviate one or more disorder symptoms or treat one or more disorders.

The term "symptom" for the purposes of this invention means any discomfort or combination of discomforts associated with a disorder. Without limiting the breadth of the foregoing, symptoms can include: dizziness; vertigo; nausea; imbalance; paresthesia; dysesthesia; sensitivity to light; sensitivity to odor; sensitivity to sound; anxiety; sleeplessness; irritability; fatigue; loss of appetite; blurred vision; gut disturbances; acute pain or chronic pain of varying characteristics including but not limited to throbbing, tearing, sharp, dull, deep, lancinating, burning, aching, stabbing, intense, lightning-like, sense of swelling, or tingling; or the like; or combinations thereof.

The term "disorder" for the purposes of this invention means a physical or mental condition which may not be normal or healthy. Without limiting the breadth of the foregoing, a disorder can include: neuropathic craniofacial pain syndromes such as neuralgias, for example trigeminal neuralgia; temporomandibular joint syndrome; headache syndromes such as migraine headaches, chronic daily headaches, cluster headaches, muscle tension headaches, post-traumatic headaches, or chronic paroxysmal hemicranias; endolymphatic hydrops; vertigo; tinnitus; syndromes resulting from brain injury; syndromes resulting from impaired neurologic function, including cognitive disorders such as attention deficit disorder, emotional disorders such as anxiety disorders, or seizure disorders; phantom limb; middle ear disorders; inner ear disorders; or the like, or combinations thereof.

Now referring primarily to FIG. 8, FIG. 9A, FIG. 9B, FIG. 28, FIG. 29A, and FIG. 29B, particular embodiments of the external ear canal pressure regulation device (1) can include a first fluid flow generator (2), which can have any of a numerous and wide variety of configurations capable of generating a first fluid flow (8) between the first fluid flow generator (2) and a first axial earpiece conduit (4) of a first earpiece (3). As to particular embodiments, the first fluid flow generator (2) can include a volumetrically adjustable element (23) capable of operation between a greater volume and a lesser volume. As an illustrative example, operating the volumetrically adjustable element (23) from a greater volume to a lesser volume can generate a first fluid flow (8) away from the first fluid flow generator (2) whereas operating the volumetrically adjustable element (23) from a lesser volume to a greater volume can generate a first fluid flow (8) toward the first fluid flow generator (2).

As to particular embodiments, the first fluid flow generator (2) can include a positive displacement pump (24), which can be configured as a rotary positive displacement pump, such as a gear pump, a screw pump, or a rotary vane pump; a reciprocating positive displacement pump, such as a plunger pump, a diaphragm pump, or a piston pump; or any pump configuration capable of moving a fluid volume (21) or generating a first fluid flow (8) between the first fluid flow generator (2) and the first axial earpiece conduit (4). As an illustrative example, a positive displacement pump (24) which may be useful in particular embodiments of the external ear canal pressure regulation device (1) may be the SP 100 EC or the SP 100 EC-LC, which can be obtained from Schwarzer Precision GmbH+ Co., Am Lichtbogen 7, 45141 Essen, Germany. As an illustrative example, an axial earpiece conduit (4)(13) which may be useful in particular embodiments of the external ear canal pressure regulation device (1) to fluidicly couple to a positive displace pump (24) may be multi-lumen micro-extruded tubing, such multi-lumen micro-extruded tubing which can be obtained from Microspec Corporation, 327 Jaffrey Road, Peterborough, NH, 03458, USA.

Figure 8:
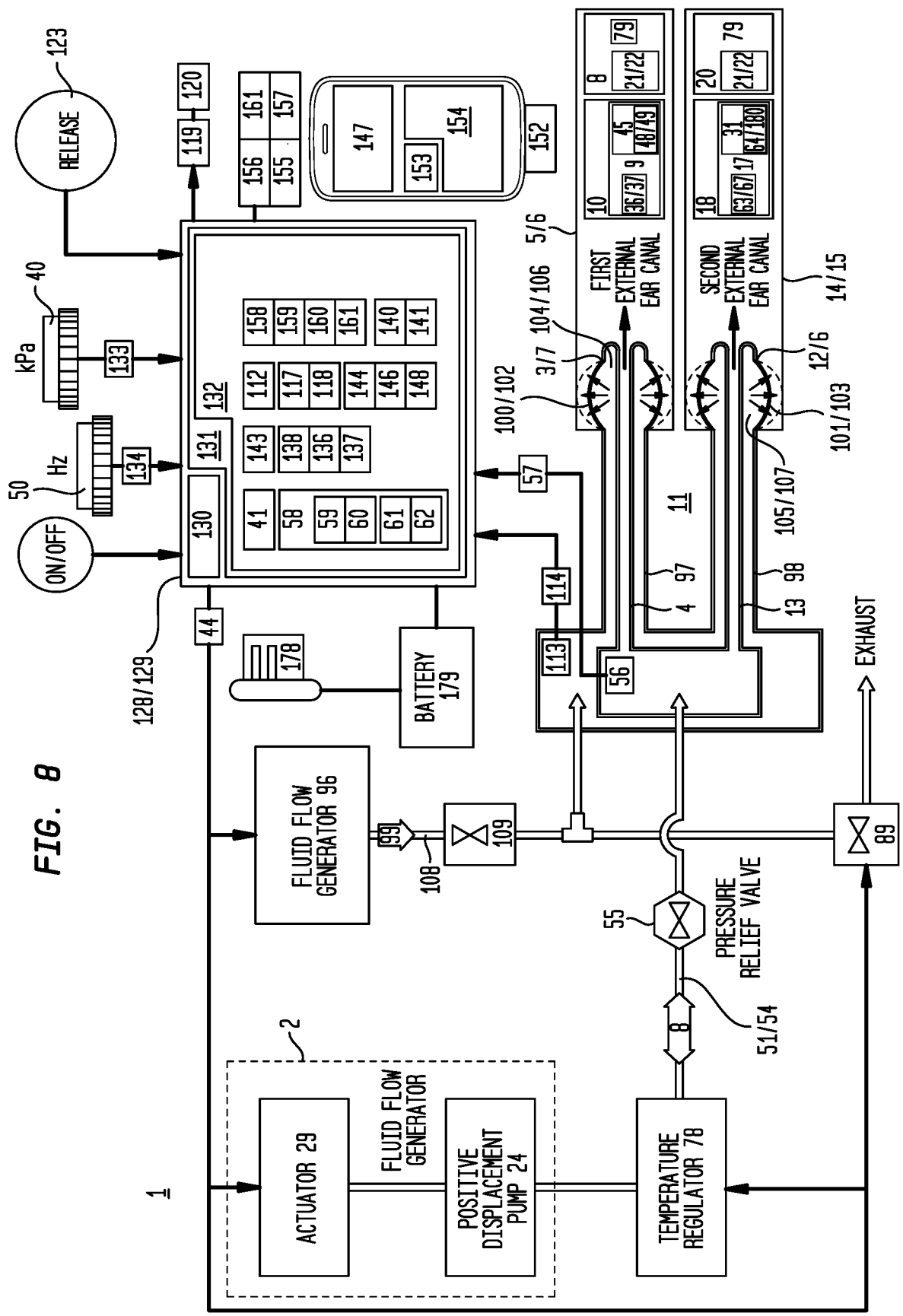
FIG. 8 is a schematic block diagram of the particular embodiment of an external ear canal pressure regulation device shown in FIG. 7 operable to achieve a pressure differential between an external ear canal pressure and an ambient pressure.

Now referring primarily to FIG. 8, FIG. 9A, and FIG. 9B, the first fluid flow generator (2) can be configured as a piston pump (25) in which a piston (26) reciprocally operates in a barrel (27) to adjust a barrel internal volume (28) between a greater volume and a lesser volume. As an illustrative example, the piston (26) can operate to decrease a barrel internal volume (28), thereby generating a first fluid flow (8)

away from the first fluid flow generator (2) toward the first axial earpiece conduit (4). As to particular embodiments having the first earpiece external surface (7) sealably engaged with the first external ear canal (5) (as shown in the illustrative examples of FIG. 4 and FIG. 5A), the first fluid flow (8) can egress from the first axial earpiece conduit (4) toward the first external ear canal (5), which can generate a first external ear canal pressure (10) greater than the ambient pressure (11). Conversely, the piston (26) can operate to increase the barrel internal volume (28), thereby generating a first fluid flow (8) from the first axial earpiece conduit (4) toward the first fluid flow generator (2). As to particular embodiments having the first earpiece external surface (7) sealably engaged with the first external ear canal (5), the first fluid flow (8) can ingress to the first axial earpiece conduit (4) from the first external ear canal (5), which can generate a first external ear canal pressure (10) lesser than the ambient pressure (11).

Now referring primarily to FIG. 8 and FIG. 9B, as to particular embodiments, the piston (26) can be operatively coupled to an actuator (29), which can function to move the piston (26) within the barrel (27) to generate a first fluid flow (8) between the first fluid flow generator (2) and the first axial earpiece conduit (4). As to particular embodiments, the actuator (29) can be configured as a linear actuator (30), including a mechanical actuator, a hydraulic actuator, a pneumatic actuator, a piezoelectric actuator, an electro-mechanical actuator, a linear motor, a telescoping linear actuator, or any linear actuator configuration capable of generating linear motion. As an illustrative example, a linear actuator (30) which may be useful in particular embodiments of the external ear canal pressure regulation device (1) may be the miniature linear actuator AS-03, which can be obtained from Lunematic. As to particular embodiments, the linear actuator (30) can be configured as threaded shaft which upon rotation moves linearly. The linear actuator (30) can be disposed adjacent the barrel (27) of the first fluid flow generator (2). The linear motion of the threaded shaft can be coupled to the motion of the piston (26) of the first fluid flow generator (2) by a connector (32), whereby linear motion of the threaded shaft causes linear motion of the piston (26) within the barrel (27) to adjust the barrel internal volume (28), generating a first fluid flow (8) between the first fluid flow generator (2) and the first axial earpiece conduit (4).

As to other particular embodiments, the first fluid flow generator (2) can be configured as a diaphragm pump, which can include a diaphragm having a resiliently flexible wall bounding a chamber volume. The resiliently flexible wall in a deformed condition can decrease the chamber volume, thereby generating a first fluid flow (8) away from the first fluid flow generator (2) toward the first axial earpiece conduit (4). As to particular embodiments having the first earpiece external surface (7) sealably engaged with the first external ear canal (5), the first fluid flow (8) can egress from the first axial earpiece conduit (4) toward the first external ear canal (5), which can generate a first external ear canal pressure (10) greater than the ambient pressure (11). Conversely, the resiliently flexible wall can return toward a non-deformed condition from the deformed condition, increasing the chamber volume and thereby generating a first fluid flow (8) toward the first fluid flow generator (2) from the first axial earpiece conduit (4). As to particular embodiments having the first earpiece external surface (7) sealably engaged with the first external ear canal (5), the first fluid flow (8) can ingress to the first axial earpiece conduit (4) from the first external ear canal (5), which can generate a first external ear canal pressure (10) lesser than the ambient pressure (11).

As to particular embodiments, the diaphragm can be a piezoelectric diaphragm, having a resiliently flexible wall which vibrates upon the application of a sine wave voltage. The vibrations can generate a first fluid flow (8), with the first fluid flow (8) having flow rates of up to 0.8 liters per minute and typical amounts of pressure up to 1.5 kilopascals capable of being achieved by a 15 Vp-p 25 kHz signal. The piezoelectric diaphragm can be operated above the normal audible range by a 24-25 kHz signal.

Figure 4:
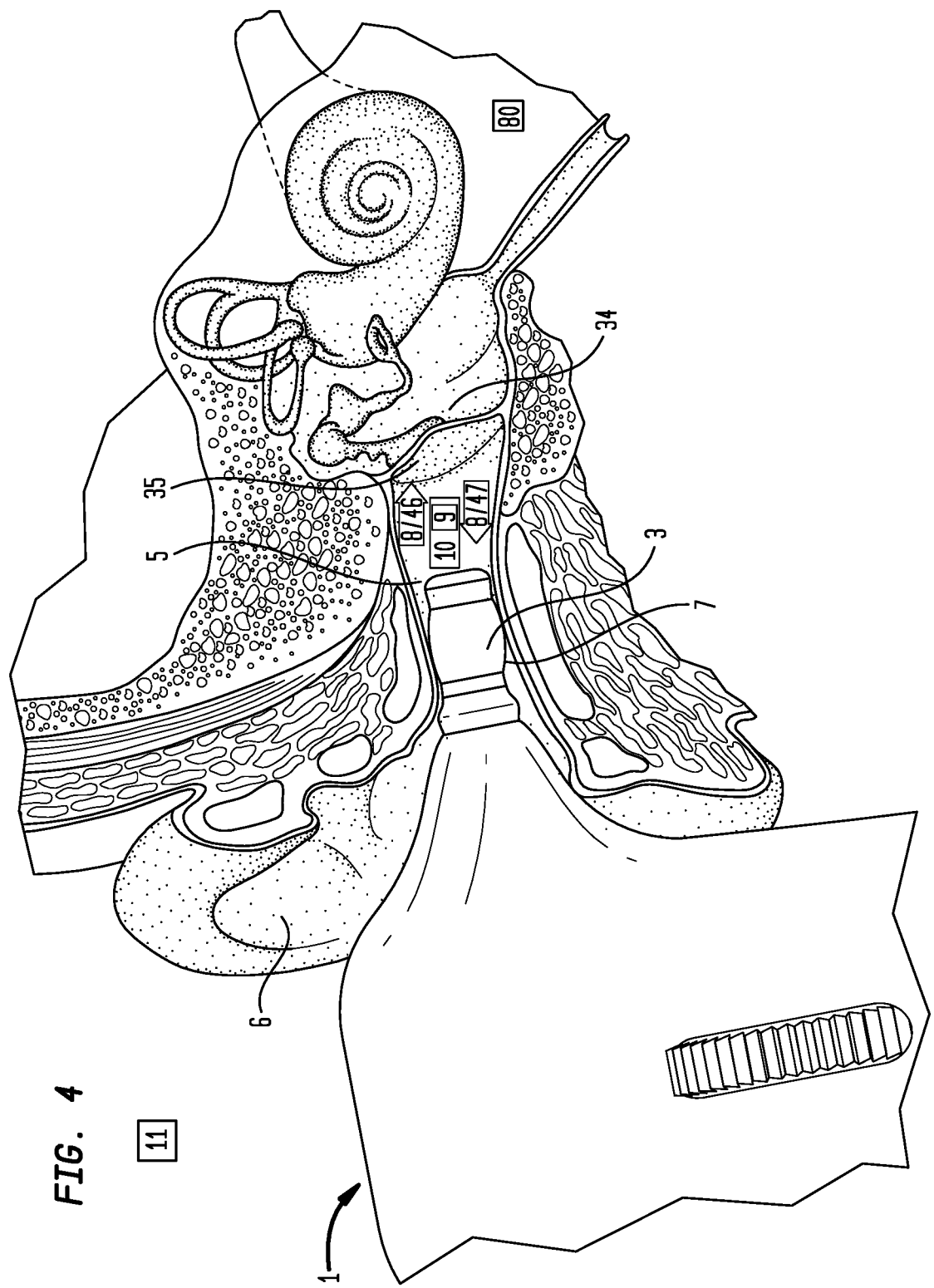
FIG. 4 is an illustration of a particular embodiment of an external ear canal pressure regulation device sealably engaged with the external ear canal.
Figure 5A:
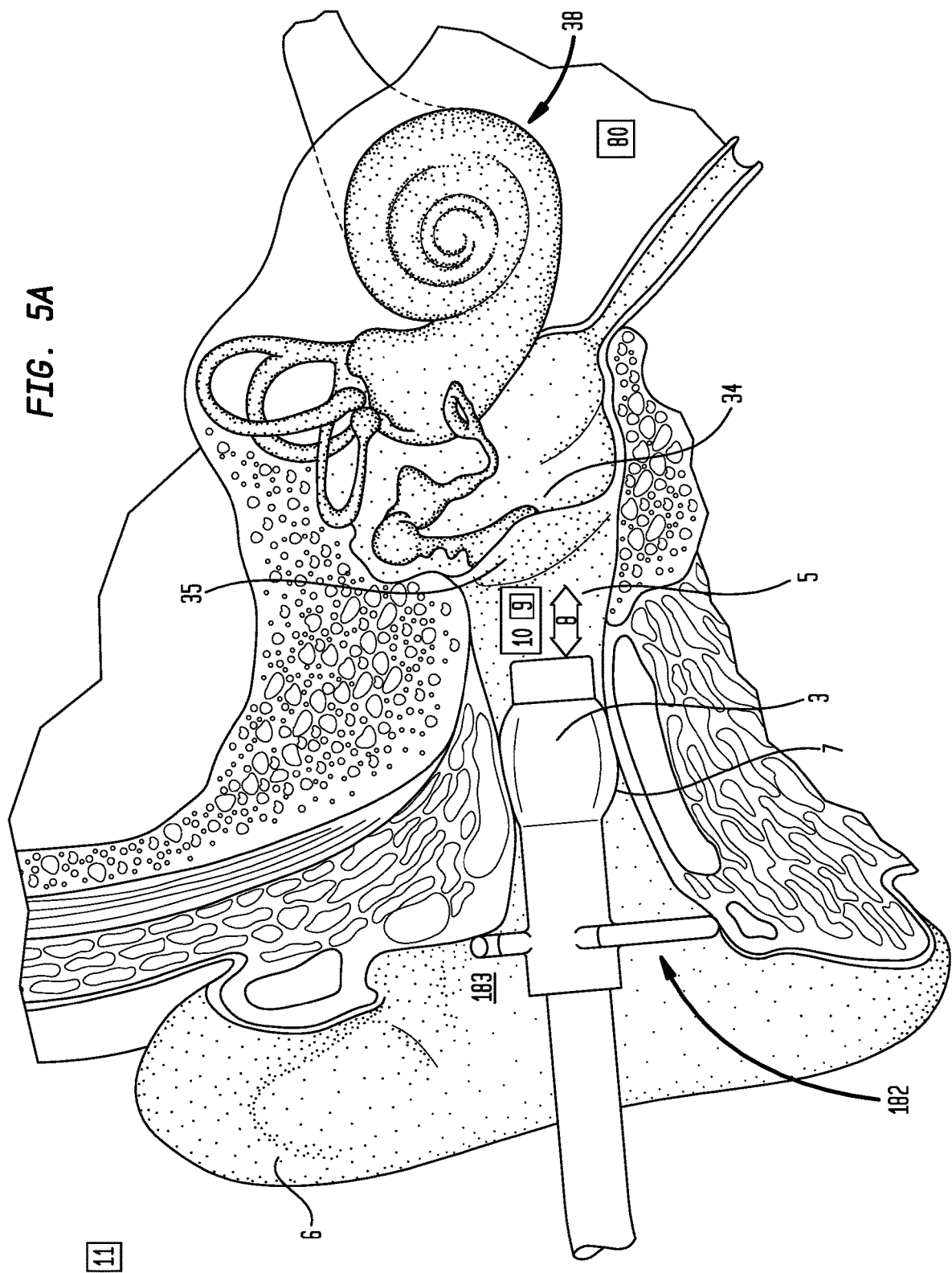
FIG. 5A is an illustration of a particular embodiment of an external ear canal pressure regulation device sealably engaged with a first external ear canal.
Figure 5B:
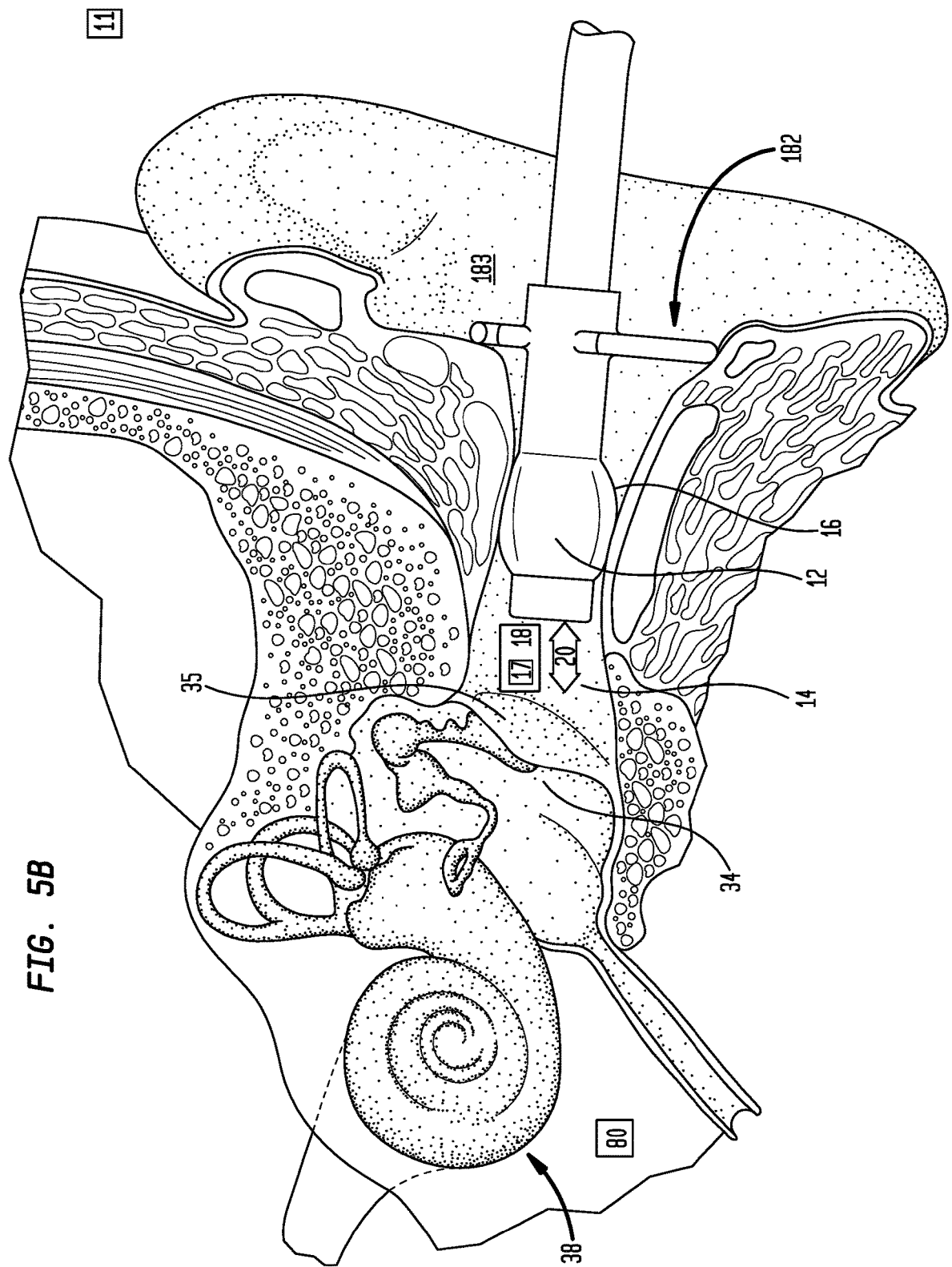
FIG. 5B is an illustration of a particular embodiment of an external ear canal pressure regulation device sealably engaged with a second external ear canal.
Figure 7:
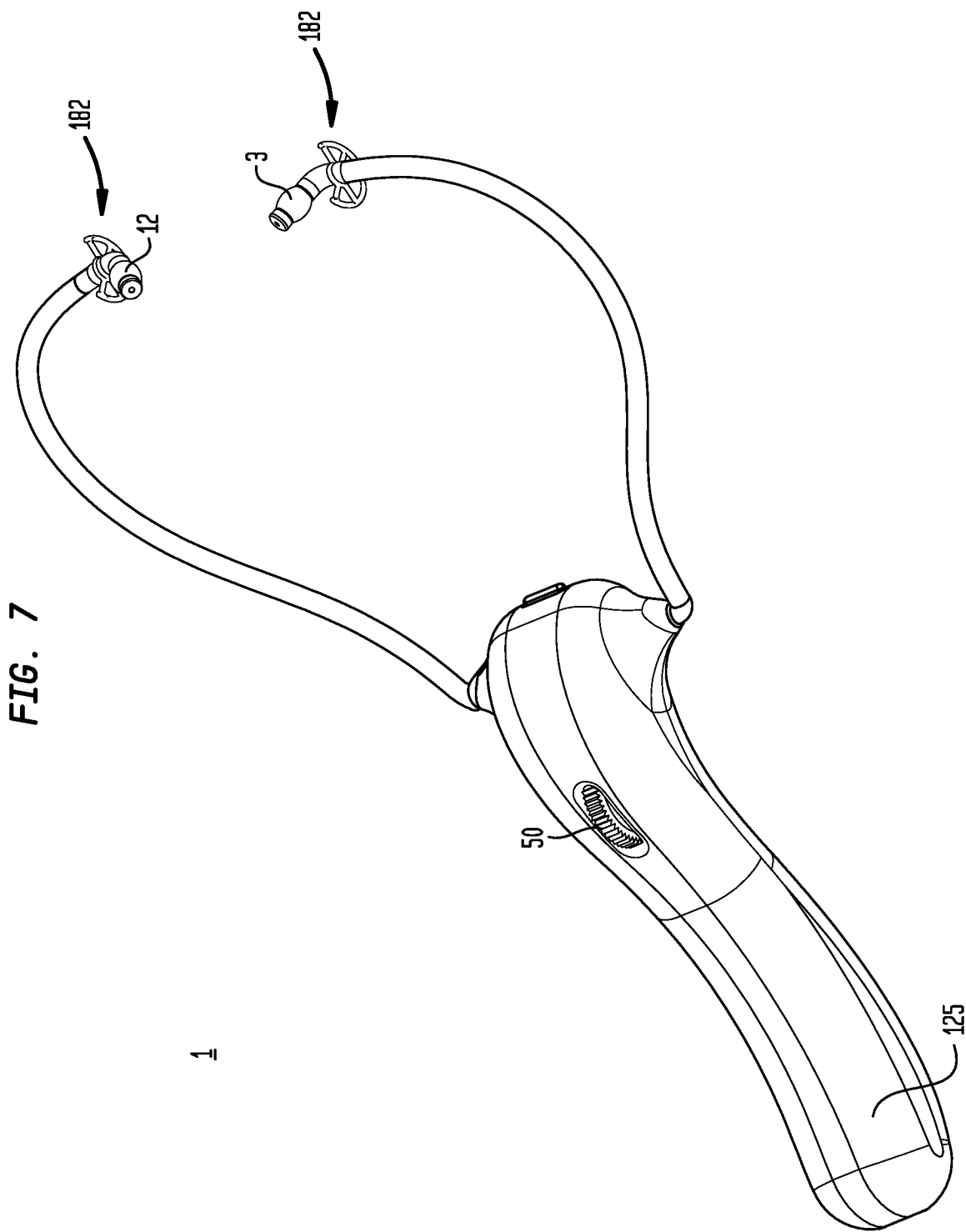
FIG. 7 is a perspective view of a particular embodiment of an external ear canal pressure regulation device.

Now referring primarily to FIG. 4 and FIG. 5A, the first fluid flow generator (2) can be configured to generate a first fluid flow (8) between the first fluid flow generator (2) and the first axial earpiece conduit (4) having fluid volume (21) typically in a range of between 0 milliliters to about 20 milliliters; however, embodiments can have a lesser or greater fluid volume (21) depending upon the application. As to particular embodiments, the fluid volume (21), or a pre-selected fluid volume (22), can selected from one or more of the group including or consisting of: between 0 milliliters to about 2 milliliters, between about 1 milliliter to about 3 milliliters, between about 2 milliliters to about 4 milliliters, between about 3 milliliters to about 5 milliliters, between about 4 milliliters to about 6 milliliters, between about 5 milliliters to about 7 milliliters, between about 6 milliliters to about 8 milliliters, between about 7 milliliters to about 9 milliliters, between about 8 milliliters to about 10 milliliters, between about 9 milliliters to about 11 milliliters, between about 10 milliliters to about 12 milliliters, between about 11 milliliters to about 13 milliliters, between about 12 milliliters to about 14 milliliters, between about 13 milliliters to about 15 milliliters, between about 14 milliliters to about 16 milliliters, between about 15 milliliters to about 17 milliliters, between about 16 milliliters to about 18 milliliters, between about 17 milliliters to about 19 milliliters, and between about 18 milliliters to about 20 milliliters.

One or a plurality fluid volumes (21) (or pre-selected fluid volumes (22)) can be generated with the external ear canal pressure regulation device (1) depending upon the method of use, which can be further influenced by factors such as user (33) anatomy, physiology, or biochemistry of an auditory meatus (34); disorder symptom targeted for alleviation; disorder targeted for treatment; observable effect(s) of using one or a plurality of fluid volumes (21) (or pre-selected fluid volumes (22)) in a particular method of using the external ear canal pressure regulation device (1); or the like; or combinations thereof; whereby the one or the plurality of fluid volumes (21) (or pre-selected fluid volumes (22)) can administered effective to alleviate one or more disorder symptoms or treat one or more disorders, but not so much as to cause discomfort to the user (33) or injury to the auditory meatus (34) or a tympanic membrane (35).

Again referring primarily to FIG. 4 and FIG. 5A, the first fluid flow generator (2) can be capable of generating a first pressure differential (9) between the first external ear canal pressure (10) and the ambient pressure (11). As to particular embodiments, the external ear canal pressure regulation device (1) can be operated to achieve a first external ear canal pressure (10) which can be lesser or greater than the ambient pressure (11). The effective range of the first external ear canal pressure (10) can be from just above or below the ambient pressure (11) increasing to a first external ear canal pressure (10), above or below the ambient pressure (11), just short of causing discomfort to the user (33) or injury to the auditory meatus (34) or the tympanic membrane (35). While authorities vary on the first external ear canal pressure (10) that may result in discomfort to a user (33) or injury to the auditory meatus (34) or the tympanic membrane (35), typically embodiments of the external ear canal pressure regulation device (1) would not be configured to operate in excess of about −50 kilopascals below the ambient pressure (11) or about +50 kilopascals above the ambient pressure (11).

Accordingly, the first fluid flow generator (2) can be capable of generating a first pressure differential (9) having a first pressure differential amplitude (36) in a range of between 0 kilopascals to about 50 kilopascals; however, embodiments can generate a lesser or greater first pressure differential amplitude (36) depending upon the application. As to particular embodiments, the first pressure differential amplitude (36), or a first pre-selected pressure differential amplitude (37), can be selected from one or more of the group including of consisting of: between 0 kilopascals to about 5 kilopascals, between about 2.5 kilopascals to about 7.5 kilopascals, between about 5 kilopascals to about 10 kilopascals, between about 7.5 kilopascals to about 12.5 kilopascals, between about 10 kilopascals to about 15 kilopascals, between about 12.5 kilopascals to about 17.5 kilopascals, between about 15 kilopascals to about 20 kilopascals, between about 17.5 kilopascals to about 22.5 kilopascals, between about 20 kilopascals to about 25 kilopascals, between about 22.5 kilopascals to about 27.5 kilopascals, between about 25 kilopascals to about 30 kilopascals, between about 27.5 kilopascals to about 32.5 kilopascals, between about 30 kilopascals to about 35 kilopascals, between about 32.5 kilopascals to about 37.5 kilopascals, between about 35 kilopascals to about 40 kilopascals, between about 37.5 kilopascals to about 42.5 kilopascals, between about 40 kilopascals to about 45 kilopascals, between about 42.5 kilopascals to about 47.5 kilopascals, and between about 45 kilopascals to about 50 kilopascals.

One or a plurality of first pressure differential amplitudes (36) (or first pre-selected pressure differential amplitudes (37)) can be generated with the external ear canal pressure regulation device (1) depending upon the method of use, which can be further influenced by factors such as user (33) anatomy, physiology, or biochemistry of the auditory meatus (34); disorder symptom targeted for alleviation; disorder targeted for treatment; observable effect(s) of using one or more first pressure differential amplitudes (36) (or first pre-selected pressure differential amplitudes (37)) in a particular method of using the external ear external canal pressure regulation device (1); or the like; or combinations thereof; whereby the one or the plurality of first pressure differential amplitudes (36) (or first pre-selected pressure differential amplitudes (37)) can be administered effective to alleviate one or more disorder symptoms or treat one or more disorders, but not so much as to cause discomfort to the user (33) or injury to the auditory meatus (34) or a tympanic membrane (35).

As to particular embodiments, the first fluid pressure differential (9) generated by the first fluid flow generator (2) can be capable of moving a tympanic membrane (35), which lies across the first external ear canal (5) to separate the first external ear canal (5) from a middle ear (38), effective to alleviate one or more disorder symptoms or treat one or more disorders. The tympanic membrane (35) comprises three layers, including an intermediate layer (lamina propria) which is disposed between an external epidermal layer and an internal mucosal layer. The intermediate layer includes modified mechanioreceptive vaterpacinian corpuscles ("mechanoreceptors"), which can be sensitive to deformation or stretch of the tympanic membrane (35). As such, these mechanoreceptors can function as baroreceptors and transmit afferent signals to the central nervous system associated with inward ("toward the middle ear") or outward ("away from the middle ear") movement of the tympanic membrane (35).

The mechanoreceptors can transmit the afferent signals to the auriculotemporal nerve via A-β pseudounipolar fibers, which subsequently merges with the mandibular nerve. The mandibular nerve converges with the maxillary nerve and the ophthalmic nerve to form the trigeminal ganglion, where the cell bodies of the primary afferent pressure-conveying fibers reside. The afferent fibers are conveyed through the sensory root of the trigeminal nerve to the ventrolateral aspect of the midbelly of the pons. In this way, the trigeminal nerve can transmit sensory signals including nociceptive signals ("pain signals") from the cranium and face to the central nervous system. The afferent fibers then enter the brainstem and synapse on various parts of the trigeminal nuclear system, including the deep lamina of the Trigeminal Nucleus Caudalis, where the afferent fibers can induce GAB Aergic interneurons to hyperpolarize nociceptive fibers and interneurons in the superficial laminae to block nociceptive transmission.

The first or second pressure differentials (9)(17) between the corresponding first or second external ear canal pressures (10)(18) and the ambient pressure (11) generated by the first fluid flow generator (2) can induce an anti-nociceptive barrage of mechanoreceptor-derived neural impulses such that the various related nuclei of the brainstem pain matrix can become attenuated and resume normal, steady-state activity. Also, parasympathetically-induced intracranial vasodilation can cease, restoring resting vascular flow and tone within the cranial vasculature, a portion of which can be associated with the trigeminal nerve and trigeminal nerve fibers as part of the trigeminal system. In addition to modulating vascular dynamics, biochemical alterations can be induced, such as a down-regulation of inflammatory cytokines or other pain-promoting compounds within or around the cranial vascular beds, whereby the vascular normalization can lead to further quiescence of trigeminal nociceptive afferentation which can culminate in the alleviation of one or more disorder symptoms or treatment of one or more disorders Now referring primarily to FIG. 4 and FIG. 5A, as to particular embodiments of the external ear canal pressure regulation device (1), the first fluid flow (8) in the first external ear canal (5) of the first ear (6) can generate a first external ear canal pressure (10) greater than ambient pressure (11) which causes a corresponding movement of the tympanic membrane (35) toward the middle ear (38), thus increasing the concavity of the tympanic membrane (35). Similarly, the first fluid flow (8) in the first external ear canal (5) of the first ear (6) can generate a first external ear canal pressure (10) lesser than the ambient pressure (11) which causes corresponding movement of the tympanic membrane (35) away from the middle ear (38), thus decreasing the concavity of the tympanic membrane (35). As to particular embodiments or methods, the first or second pressure differentials (9)(17) generated by the first fluid flow generator (2) can move the tympanic membrane (35) toward or away from the middle ear (38) one or a plurality of times within a time period (39).

Movement of the tympanic membrane (35) can stimulate the mechanoreceptors, which can alleviate one or more disorder symptoms or treat one or more disorders. As an illustrative example, tympanic membrane (35) movement can generate a nerve signal which can decrease transmission of a nociceptive signal to the central nervous system, which can result in analgesic stimulation of the central nervous system. As an additional illustrative example, movement of the tympanic membrane (35) can counteract central nervous system habituation.

Now referring primarily to FIG. 8 and FIG. 9B, the external ear canal pressure regulation device (1) can further include a first pressure differential amplitude selection element (40) and a first fluid flow generator controller (41) responsive to operation of the first pressure differential amplitude selection element (40) to regulate operation of the first fluid flow generator (2) to achieve a first pre-selected pressure differential amplitude (37). As an illustrative example, the first pressure differential amplitude selection element (40) can be configured as a variable resistor (42), such as a rheostatically-controlled element (43), which can regulate an electric current by adjusting the resistance of a circuit (current being inversely proportional to resistance for a particular voltage). As such, the rheostatically-controlled element (43) can be used to adjust an electric current to control operation of the first fluid flow generator (2)(whether directly by varying current to the fluid flow generator (2) or indirectly by analyzing variation in current within the circuit to correspondingly generate a fluid flow generator drive signal (44)) to achieve the pre-selected pressure differential amplitude (37). As to particular embodiments, the rheostatically-controlled element (43) can be operated to increase the resistance of the circuit coupled to the first fluid flow generator (2), which can decrease the first pre-selected pressure differential amplitude (37). Conversely, the rheostatically-controlled element (43) can be operated to decrease the resistance of the circuit coupled to the first fluid flow generator (2), which can increase the first pre-selected pressure differential amplitude (37). As to particular embodiments, the rheostatically-controlled element (43) can include a linear rheostat having a linear conductive coil or rotary rheostat having a conductive coil configured as a torus to reduce volume.

Now referring primarily to FIG. 4, the first fluid flow generator (2) can be capable of generating a first pressure differential amplitude oscillation (45), which can reciprocally drive the first fluid flow (8) between a first fluid flow first direction (46) and a first fluid flow second direction (47) in the first axial earpiece conduit (4). As to particular embodiments, the first pressure differential amplitude oscillation (45) can have a first pressure differential amplitude oscillation frequency (48) in a range of between 0 Hertz to about 10 Hertz; however, embodiments can generate a lesser or greater a first pressure differential amplitude oscillation frequency (48) depending upon the application. As to particular embodiments, the first pressure differential amplitude oscillation frequency (48), or a first pre-selected pressure differential amplitude oscillation frequency (49), can be selected from one or more of the group including of consisting of: between 0 Hertz to about 1 Hertz, between about 0.5 Hertz to about 1.5 Hertz, between about 1 Hertz to about 2 Hertz, between about 1.5 Hertz to about 2.5 Hertz, between about 2 Hertz to about 3 Hertz, between about 2.5 Hertz to about 3.5 Hertz, between about 3 Hertz to about 4 Hertz, between about 3.5 Hertz to about 4.5 Hertz, between about 4 Hertz to about 5 Hertz, between about 4.5 Hertz to about 5.5 Hertz, between about 5 Hertz to about 6 Hertz, between about 5.5 Hertz to about 6.5 Hertz, between about 6 Hertz to about 7 Hertz, between about 6.5 Hertz to about 7.5 Hertz, between about 7 Hertz to about 8 Hertz, between about 7.5 Hertz to about 8.5 Hertz, between about 8 Hertz to about 9 Hertz, between about 8.5 Hertz to about 9.5 Hertz, and between about 9 Hertz to about 10 Hertz.

One or a plurality of first pressure differential amplitude oscillation frequencies (48) (or first pre-selected pressure differential amplitude oscillation frequencies (49)) can be generated with the external ear canal pressure regulation device (1) depending upon the method of use, which can be further influenced by factors such as user (33) anatomy, physiology, or biochemistry of the auditory meatus (34); disorder symptom targeted for alleviation; disorder targeted for treatment; observable effect(s) of using one or more first pressure differential amplitude oscillation frequencies (48) (or first pre-selected pressure differential amplitude oscillation frequencies (49)) in a particular method of using the external ear canal pressure regulation device (1); or the like; or combinations thereof; whereby the one or the plurality of first pressure differential amplitude oscillation frequencies (48) (or first pre-selected pressure differential amplitude oscillation frequencies (49)) can be administered effective to alleviate one or more disorder symptoms or treat one or more disorders, but not so much as to cause discomfort to the user (33) or injury to the auditory meatus (34) or a tympanic membrane (35).

Again referring primarily to FIG. 8 and FIG. 9B, the external ear canal pressure regulation device (1) can further include a first pressure differential amplitude oscillation frequency selection element (50). The first fluid flow generator controller (41) can be responsive to operation of the first pressure differential amplitude oscillation frequency selection element (50) to regulate operation of the first fluid flow generator (2) to achieve the first pre-selected pressure differential amplitude oscillation frequency (49). As an illustrative example, the first pressure differential amplitude oscillation frequency selection element (50) can be configured as a variable resistor (42), such as rheostatically-controlled element (43) which can have a similar configuration to the rheostatically-controlled element (43) as described above for the first pressure differential amplitude selection element (40). The variation in current in the circuit can be analyzed to generate a correspondingly varied fluid flow generator drive signal (44) to alter the first pressure differential amplitude oscillation frequency (48) of the first fluid flow (8). Accordingly, as one illustrative example, the rheostatically-controlled element (43) can be operated to increase the resistance of the circuit coupled to the first fluid flow generator (2), which can decrease the first pre-selected pressure differential amplitude oscillation frequency (49). Conversely, the rheostatically-controlled element (43) can be operated to decrease the resistance of the circuit coupled to the first fluid flow generator (2), which can increase the first pre-selected pressure differential amplitude oscillation frequency (49).

Now referring primarily to FIG. 8, FIG. 9B, FIG. 28, FIG. 29A, and FIG. 29B, the external ear canal pressure regulation device (1) can further include a fluid flow manifold (51) interruptible by operation of one or more valves (52) to correspondingly alter the configuration of a manifold fluid flow path (54) within the fluid flow manifold (51) to regulate the first fluid flow (8) (or the second fluid flow (20)) within the fluid flow manifold (51). As an illustrative example, a valve (52) which may be useful in particular embodiments of the external ear canal pressure regulation device (1) may be a solenoid valve such as Lee's High Density Interface (LHD Series) Solenoid Valves, which can be obtained from The Lee Company, 2 Pettipaug Road, Westbrook, CT, 06498, USA.

While the figures schematically illustrate particular configurations of the fluid flow manifold (51) which correspondingly define particular configurations of the manifold fluid flow path (54), these embodiments need not be so limited in regard to the configuration of the fluid flow manifold (51) or the manifold fluid flow path (54) and embodiments can include any of a wide variety of numerous configurations which can fluidicly couple the first fluid flow generator (2) with the first axial earpiece conduit (4) (or the second fluid flow generator (19) with the second axial earpiece conduit (13)), whether as a plurality of discrete conduits, a one-piece manifold, or defined by a housing (125) whether formed, molded, three-dimensionally printed, or otherwise fabricated as a one-piece construct or assembled from a plurality of pieces into which one or more valves (52) can be disposed, assembled, or otherwise coupled to generate a fluid flow manifold (51) interruptible by operation of one or more valves (52).

A valve (52) can have any type of valve configuration capable of operating between a closed condition and an open condition to unidirectionally regulate the first fluid flow (8) or the second fluid flow (20). A valve (52) can operate between the closed condition, which can be substantially leak-tight to backward flow and substantially leak-tight to forward first fluid flow (8) or second fluid flow (20) on opposed sides of the valve (52), and the open condition, which can have a forward flow in the range of about 0.2 milliliters per second to about 10 milliliters per second, with respect to the first fluid flow (8) or the second fluid flow (20). As to particular embodiments, the pressure differential between opposed sides of the valve (52) or the forward first fluid flow (8) or second fluid flow (20) in the open condition of the valve (52) can be adjusted by the configuration of the valve (52), the unrestricted cross-sectional area of the manifold fluid flow path (54), or the like, or combinations thereof. Additionally, while examples of the external ear canal pressure regulation device (1) disclosed can generate a first pressure differential amplitude (36) of up to about 50 kilopascals in the first external ear canal (5) or a second pressure differential amplitude (63) of up to about 50 kilopascals in the second external ear canal (14), these examples are not intended to teach or suggest that all embodiments of the external ear canal pressure regulation device (1) necessarily achieve this amount of first or second pressure differential amplitudes (36)(63). Rather, certain embodiments of the external ear canal pressure regulation device (1) can be configured to achieve a lesser or greater first or second pressure differential amplitude (36)(63) effective to alleviate one or more disorder symptoms or treat one or more disorders.

Again referring primarily to FIG. 8, FIG. 9B, FIG. 28, and FIG. 29A, the external ear canal pressure regulation device (1) can further include a first pressure relief valve (55) fluidicly coupled to the first axial earpiece conduit (4). The first pressure relief valve (55) in the open condition allows the first external ear canal pressure (10) to return toward the ambient pressure (11), whether from a first external ear canal pressure (10) greater than the ambient pressure (11) or a first external ear canal pressure (10) lesser than the ambient pressure (11). By operating to relieve the first pressure differential (9) when the first pressure differential amplitude (36) exceeds a first pre-selected pressure differential amplitude (37), there can be a reduced risk of discomfort to a user (33) or injury to the auditory meatus (34) or the tympanic membrane (35) when using the external ear canal pressure regulation device (1).

Figure 28:
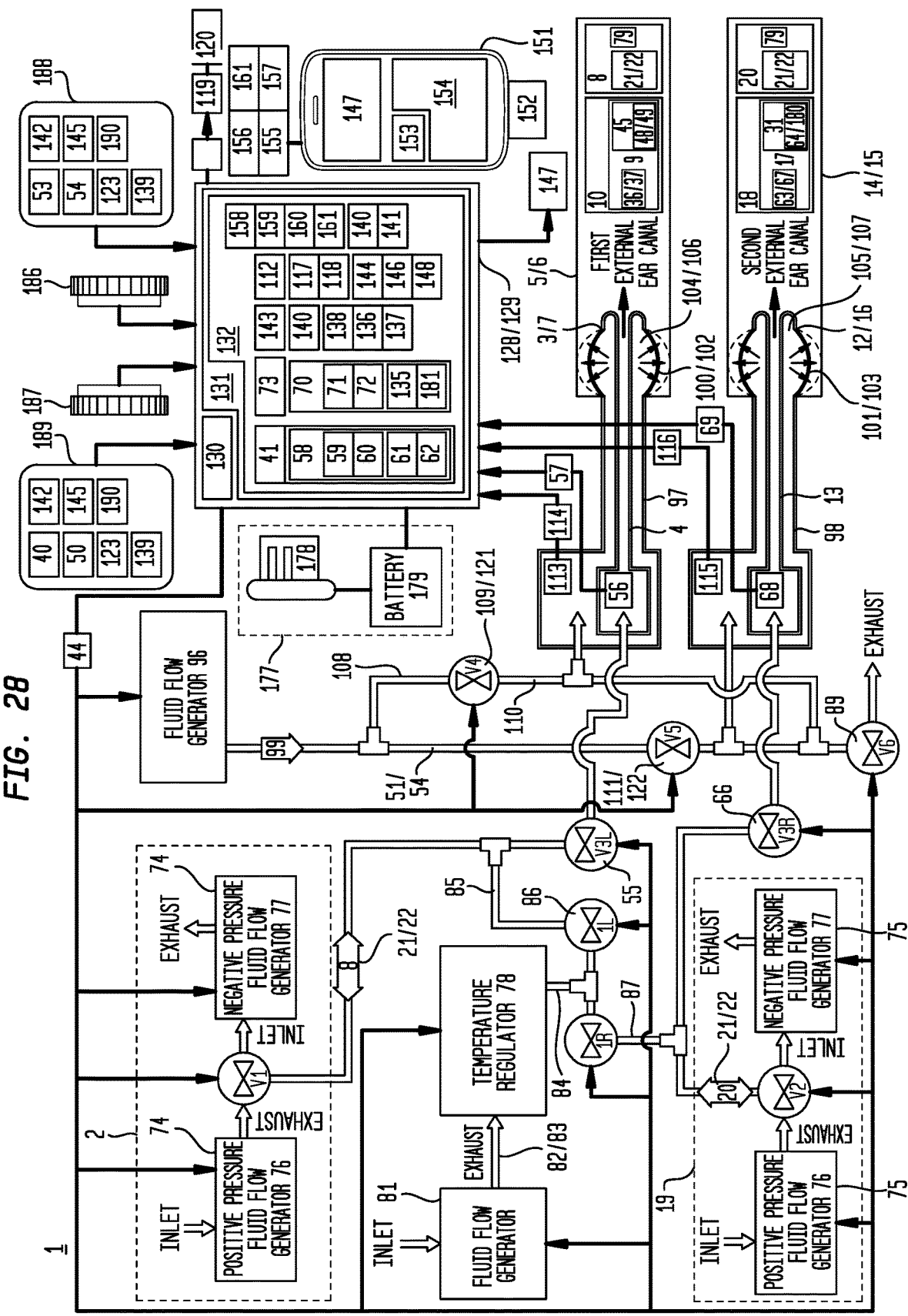
FIG. 28 is a schematic block diagram of the particular embodiment of an external ear canal pressure regulation device shown in FIG. 27 operable to achieve a pressure differential between an external ear canal pressure and an ambient pressure.

Now referring primarily to FIG. 8 and FIG. 28, the external ear canal pressure regulation device (1) can further include a first pressure sensor (56) which can generate a first pressure sensor signal (57) which can vary based upon change in the first pressure differential amplitude (36). As to particular embodiments, a pressure sensor (56) which may be useful in particular embodiments of the external ear canal pressure regulation device (1) may be an EPB small pressure probe sensor, which can be obtained from Measurement Specialties, 45738 Northport Loop West, Fremont, CA, 94538, USA.

The first pressure sensor signal (57) can be transmitted to a first pressure sensor signal analyzer (58) including a first pressure differential amplitude comparator (59) which functions to compare the first pre-selected pressure differential amplitude (37) to the first pressure differential amplitude (36) actually generated in the first external ear canal (5). As an illustrative example, a user (33) can select a first pre-selected pressure differential amplitude (37) of about 25 kilopascals using the first pressure differential amplitude selection element (40), as described above. The first pressure differential amplitude comparator (59) can function to compare the first pre-selected pressure differential amplitude (37) of about 25 kilopascals to the first pressure differential amplitude (36) actually generated in the first external ear canal (5). When operation of the first fluid flow generator (2) results in a first pressure differential amplitude (36) in the first external ear canal (5) of about 25 kilopascals within a margin of error, operation of the first fluid flow generator (2) can be curtailed for so long as the first pre-selected pressure differential amplitude (37) can be maintained for the selected time period (39).

As to particular embodiments, the first pressure sensor signal analyzer (58) can further function to generate a first pressure differential amplitude compensation signal (60). For example, when operation of the first fluid flow generator (2) results in a first pressure differential amplitude (36) which varies from the first pre-selected pressure differential amplitude (37), the first pressure sensor signal analyzer (58) can generate a first pressure differential amplitude compensation signal (60) to which the first fluid flow generator controller (41) can be responsive to achieve the first pre-selected pressure differential amplitude (37). As an illustrative example, a user (33) can select a first pre-selected pressure differential amplitude (37) of about 25 kilopascals using the first pressure differential amplitude selection element (40) as described above. Operation of the first fluid flow generator (2) can result in a first pressure differential amplitude (36) of about 20 kilopascals within the first external ear canal (5) due, for example, to improper sealed engagement of the first earpiece external surface (7) with the first external ear canal (5). The first pressure differential amplitude comparator (59) can function to compare the first pre-selected pressure differential amplitude (37) of about 25 kilopascals to the sensed first pressure differential amplitude (36) of about 20 kilopascals. When operation of the first fluid flow generator (2) results in a first pressure differential amplitude (36) which varies from the first pre-selected pressure differential amplitude (37), this instance of 5 kilopascals, the first pressure sensor signal analyzer (58) can generate a first pressure differential amplitude compensation signal (60) which correspondingly drives the first fluid flow generator (2) at a rate which increases the sensed first pressure differential amplitude (36) by about 5 kilopascals to achieve the first pre-selected pressure differential amplitude (37) of about 25 kilopascals.

Again referring primarily to FIG. 8 and FIG. 28, the first pressure sensor signal analyzer (58) can further include a first pressure differential amplitude oscillation frequency comparator (61) which can function to compare the first pre-selected pressure differential amplitude oscillation frequency (49) to the first pressure differential amplitude oscillation frequency (48) sensed by the first pressure sensor (56) in the first external ear canal (5). As an illustrative example, a user (33) can select a first pre-selected pressure differential amplitude oscillation frequency (49) of about 5 Hertz using the first pressure differential amplitude oscillation frequency selection element (50), as described above. The first fluid flow generator controller (2) can be responsive to operation of the first pressure differential amplitude oscillation frequency selection element (50) to regulate operation of the first fluid flow generator (2) to generate a first fluid flow (8) having a first pressure differential amplitude oscillation frequency (48) of about 5 Hertz. The first pressure differential amplitude oscillation frequency comparator (61) can function to compare the first pre-selected pressure differential amplitude oscillation frequency (49) of about 5 Hertz to the first pressure differential amplitude oscillation frequency (48) of about 5 Hertz generated in the first external ear canal (5). When operation of the first fluid flow generator (2) results in a first pressure differential amplitude oscillation frequency (48) corresponding to the first pre-selected pressure differential amplitude oscillation frequency (49) within a margin of error, operation of the first fluid flow generator (2) can be continued without compensation for so long as the sensed first pressure differential amplitude oscillation frequency (48) corresponds to the first pre-selected pressure differential amplitude oscillation frequency (49).

As to particular embodiments, the first pressure sensor signal analyzer (58) can further function to generate a first pressure differential amplitude oscillation frequency compensation signal (62). For example, if operation of the first fluid flow generator (2) results in a first pressure differential amplitude oscillation frequency (48) within the first external ear canal (5) which varies from the first pre-selected pressure differential amplitude oscillation frequency (49), the first pressure sensor signal analyzer (58) can generate a first pressure differential amplitude oscillation frequency compensation signal (62) to control the first fluid flow generator (2) to achieve the first pre-selected pressure differential amplitude oscillation frequency (49).

As an illustrative example, a user (33) can establish a first pre-selected pressure differential amplitude oscillation frequency (49) of about 5 Hertz using the first pressure differential amplitude oscillation frequency selection element (50), as described above. Operation of the first fluid flow generator (2) can result in a first pressure differential amplitude oscillation frequency (48) of about 2.5 Hertz within the first external ear canal (5), due, for example, to improper sealed engagement the first earpiece external surface (7) with the first external ear canal (5). The first pressure differential amplitude oscillation frequency comparator (61) can function to compare the first pre-selected pressure differential amplitude oscillation frequency (49) of about 5 Hertz to the sensed first pressure differential amplitude oscillation frequency (48) of about 2.5 Hertz. If operation of the first fluid flow generator (2) results in a first pressure differential amplitude oscillation frequency (48) which varies from the first pre-selected pressure differential amplitude oscillation frequency (49), in this instance 2.5 Hertz, the first pressure sensor signal analyzer (58) generates a first pressure differential amplitude oscillation frequency compensation signal (62) which drives the first fluid flow generator (2) to increase the first pressure differential amplitude oscillation frequency (48) to achieve the first pre-selected pressure differential amplitude oscillation frequency (49) of about 5 Hertz. When operation of the first fluid flow generator (2) results in a first pressure differential amplitude oscillation frequency (48) which corresponds to the first pre-selected pressure differential amplitude oscillation frequency (49) within a margin of error, operation of the first fluid flow generator (2) can be continued without further generation of a first pressure differential amplitude oscillation frequency compensation signal (62).

Now referring primarily to FIG. 2, FIG. 3, FIG. 5B, FIG. 7, FIG. 8, and FIG. 27 through FIG. 29B, the external ear canal pressure regulation device (1) can further include a second earpiece (12) having a second earpiece external surface (16) configured to sealably engage a second external ear canal (14) of a second ear (15) as a barrier between a second external ear canal pressure (18) and the ambient pressure (11). The second earpiece (12) can include a second axial earpiece conduit (13). The second earpiece (12) can be configured as above described for the first earpiece (3).

Figure 9:
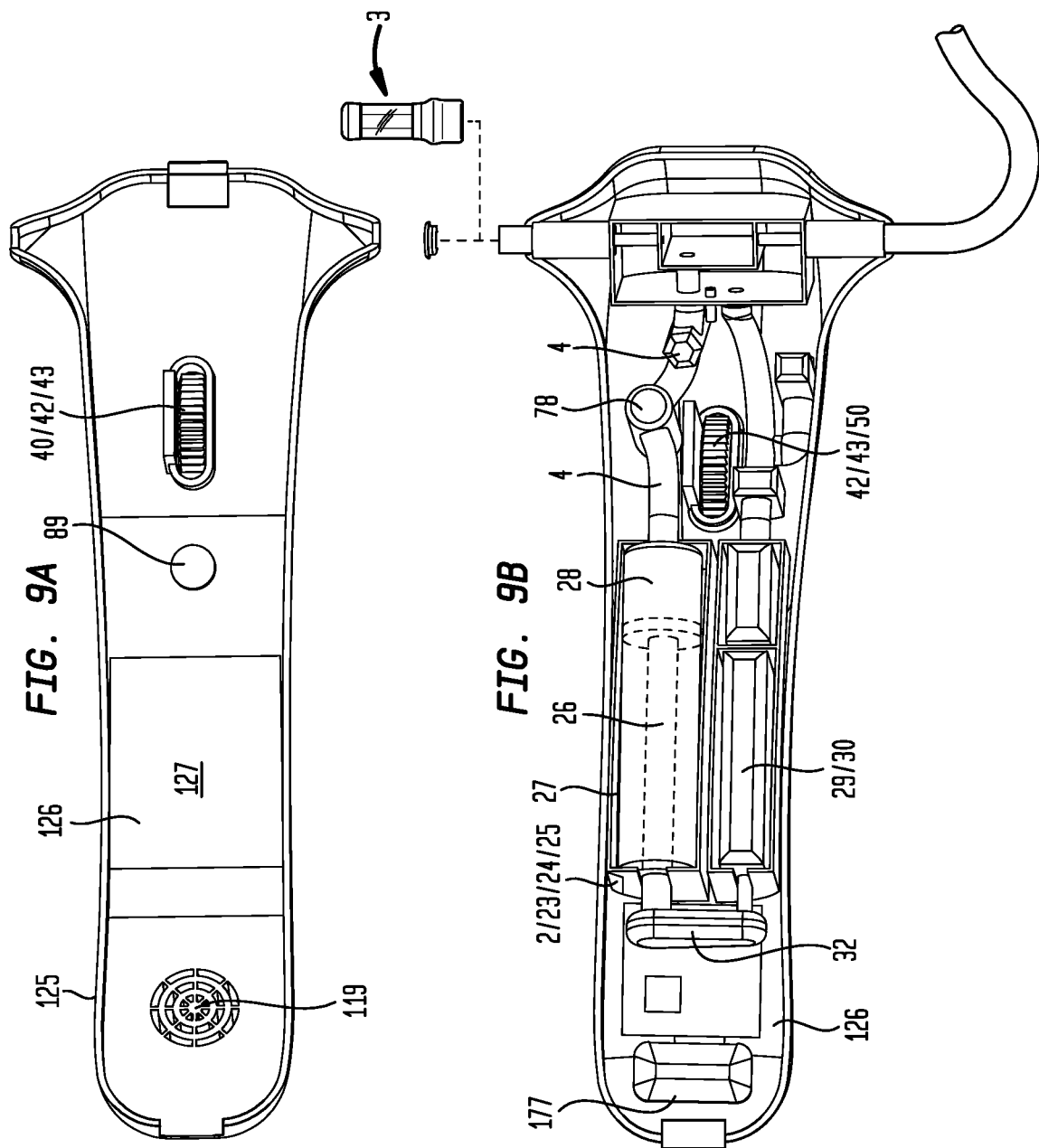
FIG. 9A is a first interior plan view of a particular embodiment of an external ear canal pressure regulation device.
FIG. 9B is a second interior plan view of the particular embodiment of the external ear canal pressure regulation device shown in FIG. 9A.
Figure 10:
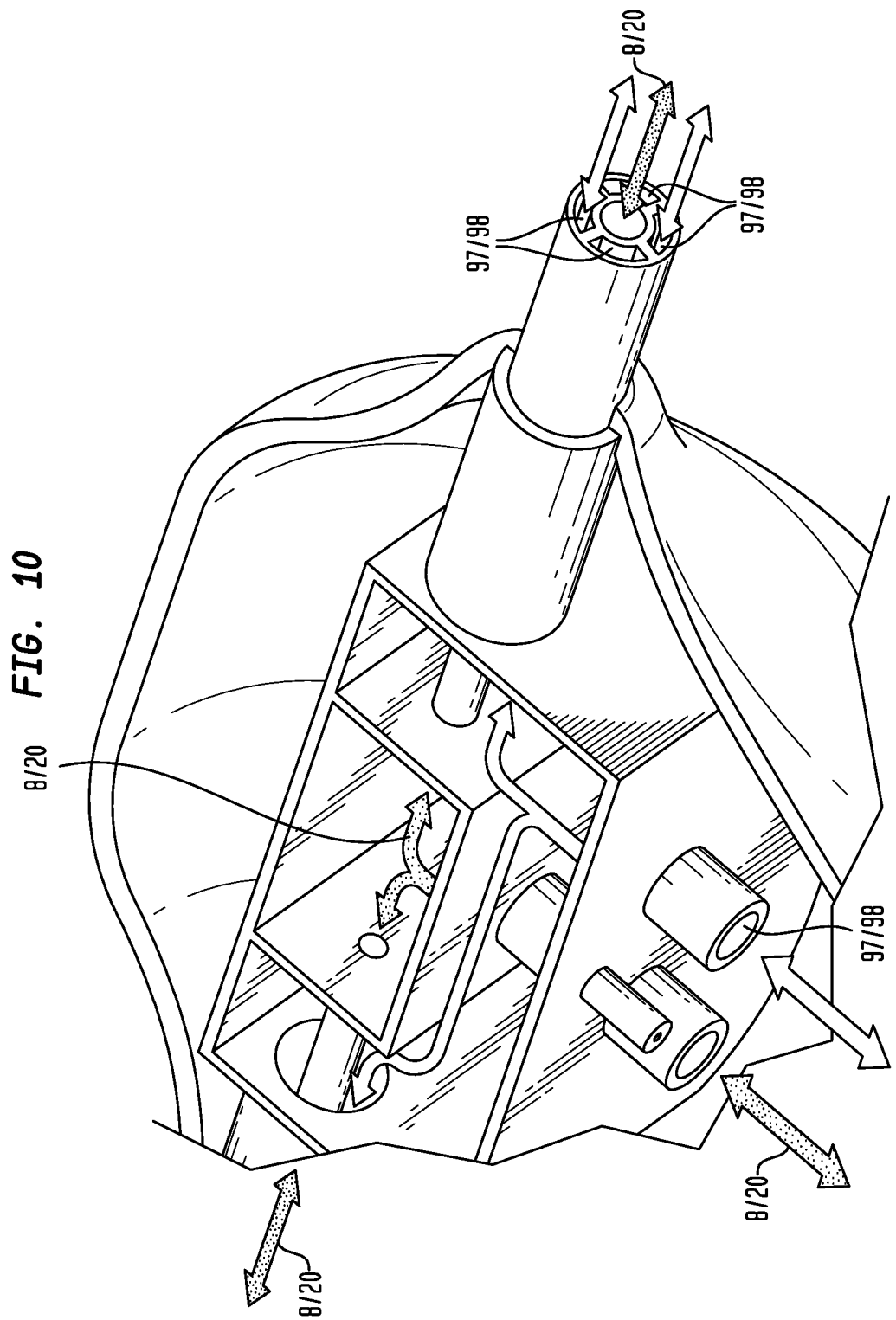
FIG. 10 is an enlarged perspective interior view of the particular embodiment of the external ear canal pressure regulation device shown in FIG. 9B.
Figure 11:
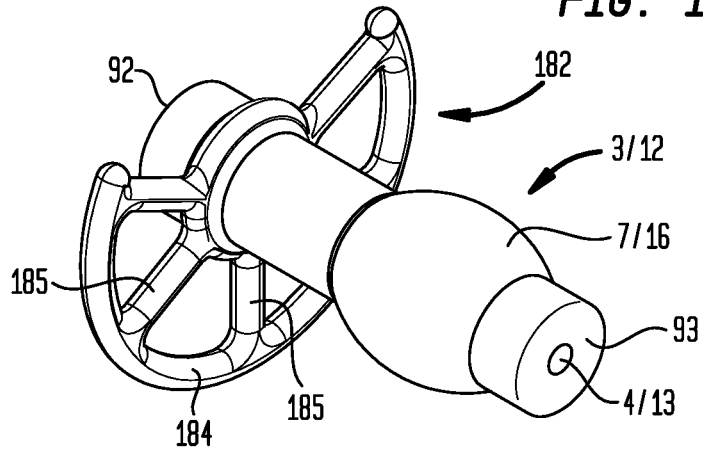
FIG. 11 is a perspective view of a particular embodiment of an earpiece of an external ear canal pressure regulation device.
Figure 12:
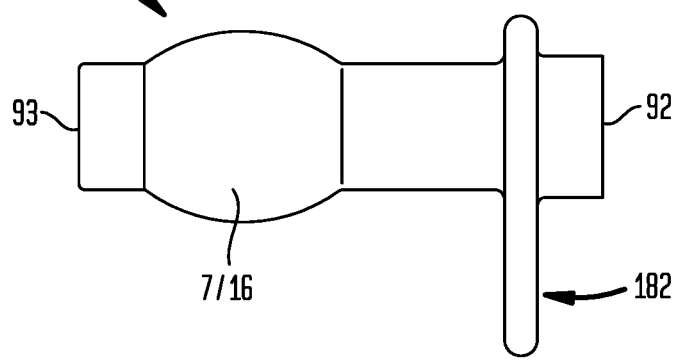
FIG. 12 is a first side view of a particular embodiment of an earpiece of an external ear canal pressure regulation device.
Figure 13:
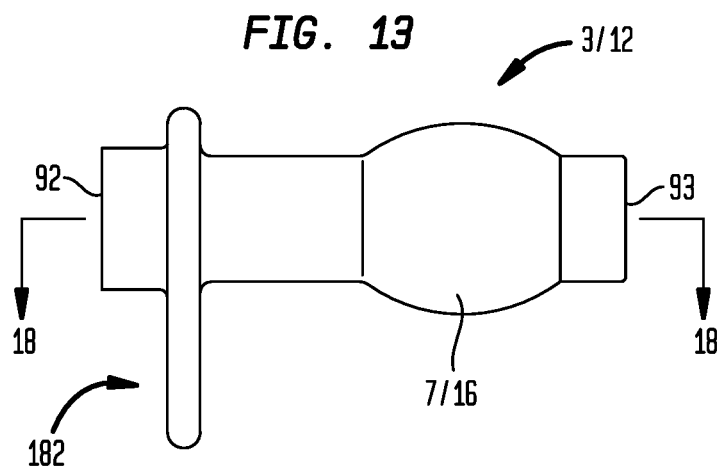
FIG. 13 is a second side view of a particular embodiment of an earpiece of an external ear canal pressure regulation device.
Figure 14:
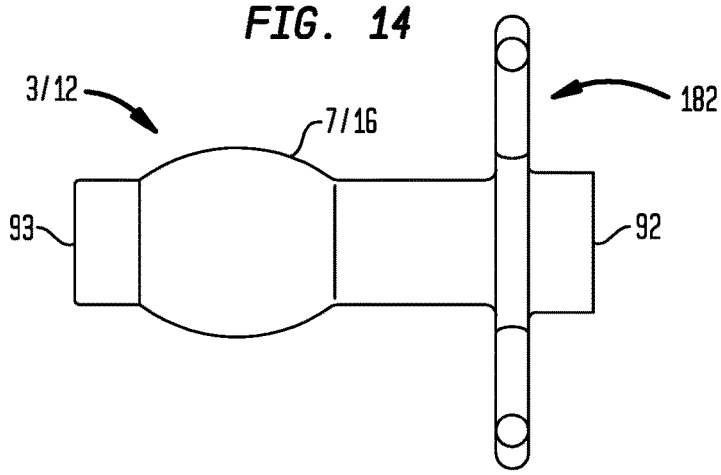
FIG. 14 is a top view of a particular embodiment of an earpiece of an external ear canal pressure regulation device.
Figure 15:
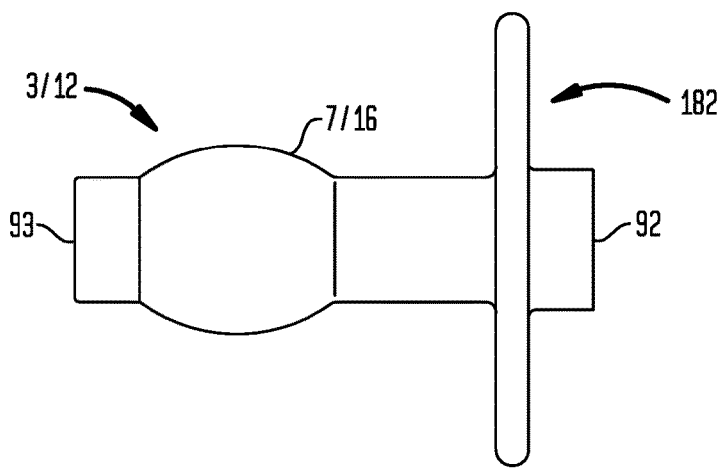
FIG. 15 is a bottom view of a particular embodiment of an earpiece of an external ear canal pressure regulation device.
Figure 16:
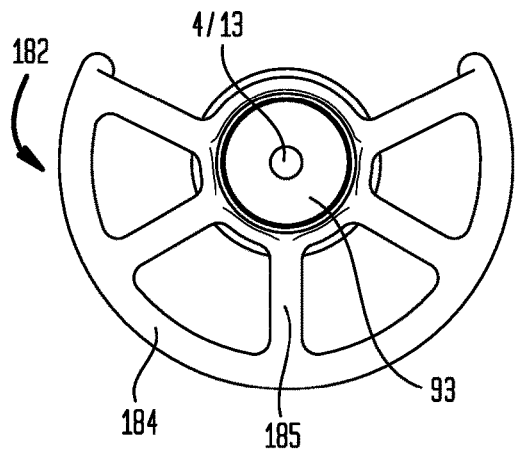
FIG. 16 is a first end view of a particular embodiment of an earpiece of an external ear canal pressure regulation device.
Figure 17:
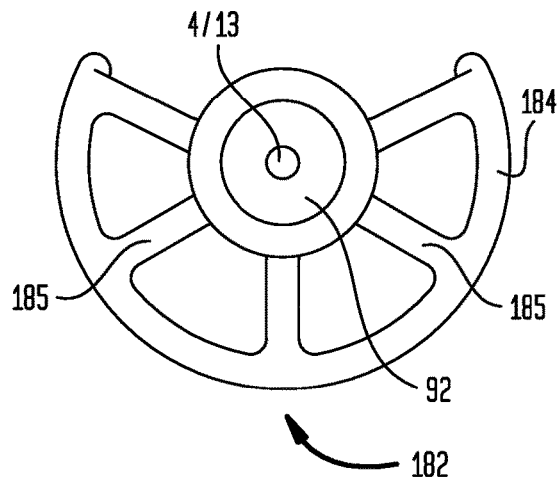
FIG. 17 is a second end view of a particular embodiment of an earpiece of an external ear canal pressure regulation device.
Figure 18:
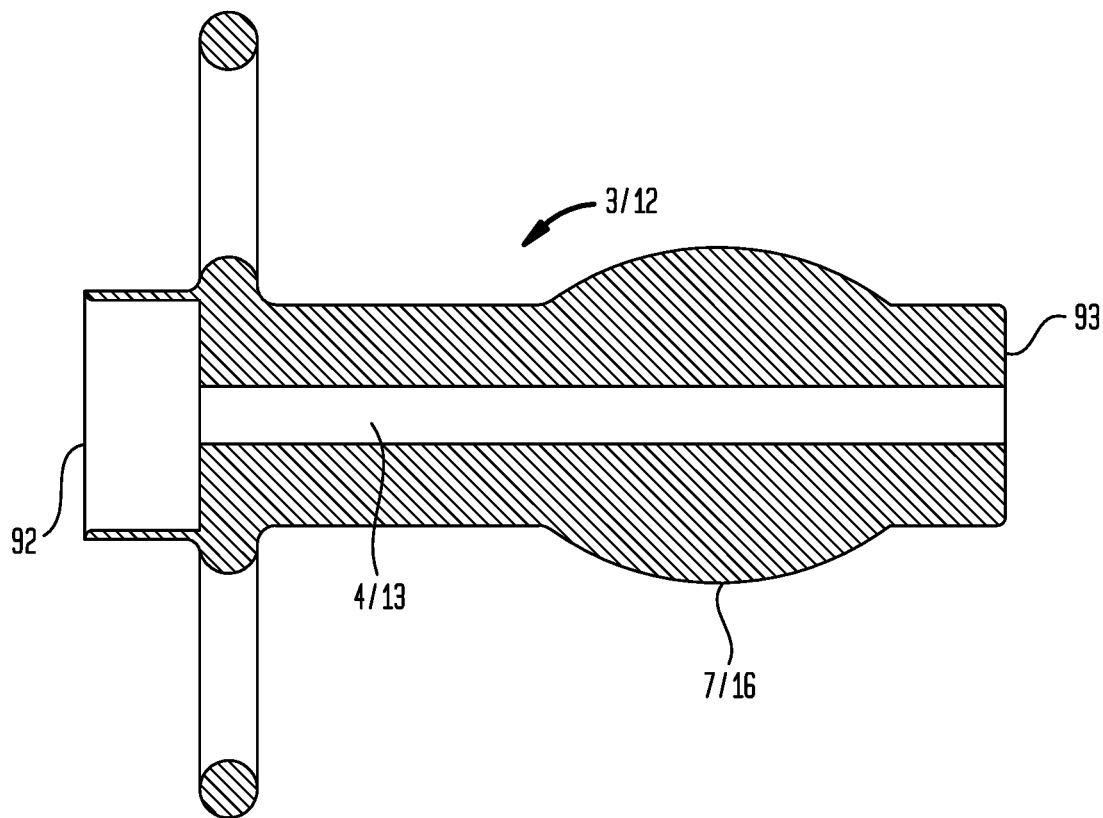
FIG. 18 is a cross section view 18-18 shown in FIG. 13 of a particular earpiece of an external ear canal pressure regulation device.
Figure 21:
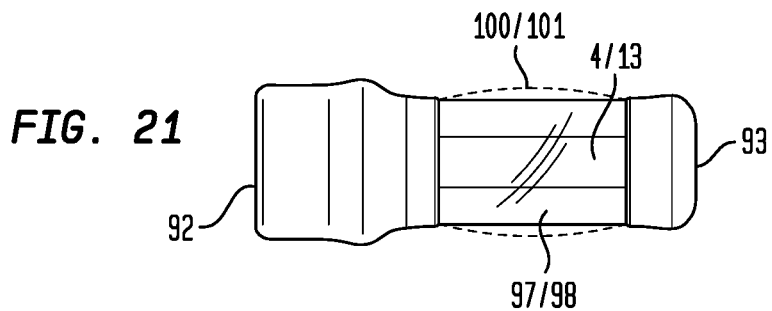
FIG. 21 is a first side view of a particular embodiment of an earpiece of an external ear canal pressure regulation device.
Figure 22:
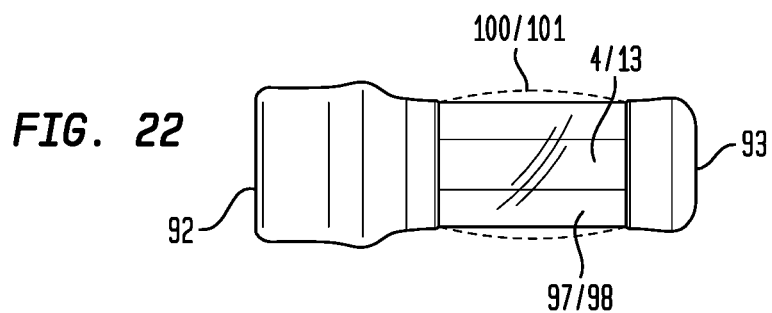
FIG. 22 is a second side view of a particular embodiment of an earpiece of an external ear canal pressure regulation device.
Figure 23:
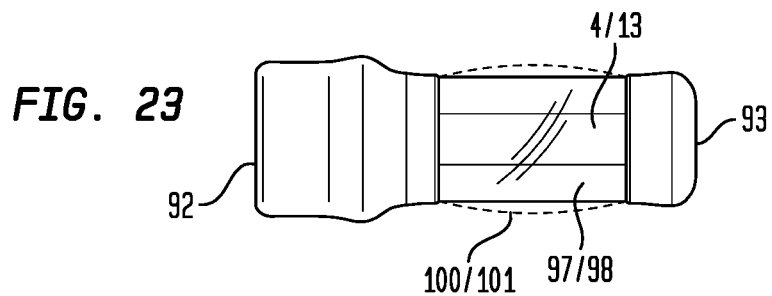
FIG. 23 is a top view of a particular embodiment of an earpiece of an external ear canal pressure regulation device.
Figure 24:
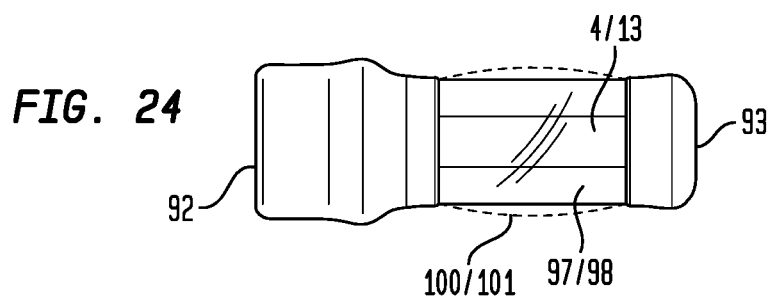
FIG. 24 is a bottom view of a particular embodiment of an earpiece of an external ear canal pressure regulation device.
Figure 25:
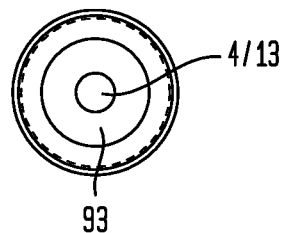
FIG. 25 is a first end view of a particular embodiment of an earpiece of an external ear canal pressure regulation device.
Figure 26:
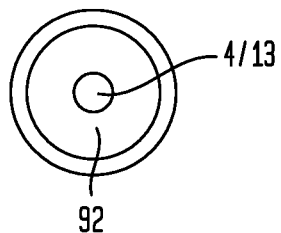
FIG. 26 is a second end view of a particular embodiment of an earpiece of an external ear canal pressure regulation device.
Figure 27:
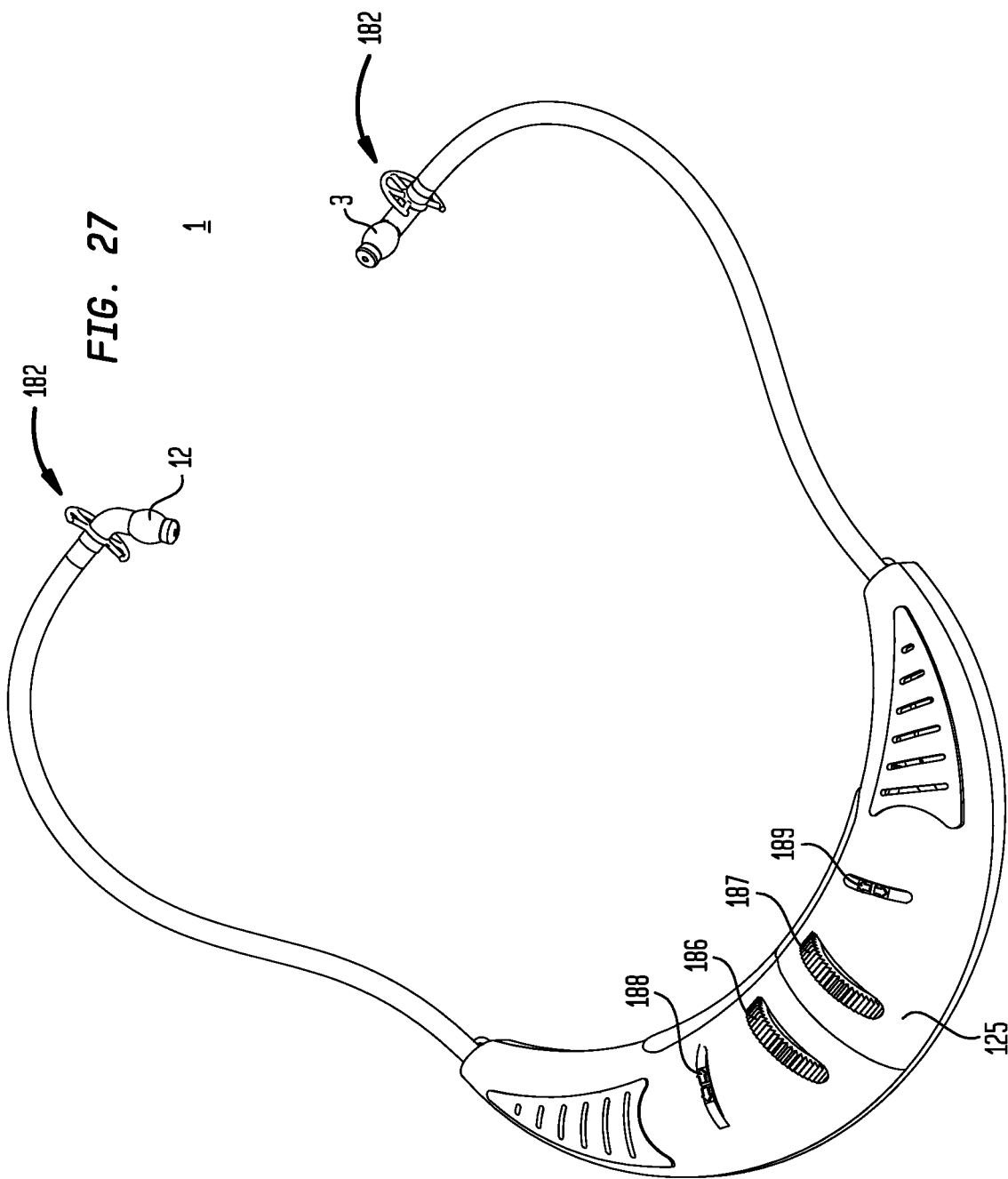
FIG. 27 is a perspective view of a particular embodiment of an external ear canal pressure regulation device.

Now referring primarily to FIG. 8 through FIG. 10, the second axial earpiece conduit (13) can be fluidicly coupled in common to the first fluid flow generator (2). Accordingly, the first fluid flow generator (2) can be capable of generating a second pressure differential (17) between the second external ear canal pressure (18) and the ambient pressure (11) which can have a second pressure differential amplitude (63) and a second pressure differential oscillation frequency (64) which can be substantially similar to the first pressure differential amplitude (36) and the first pressure differential oscillation frequency (48), as above described. Accordingly, operation of the first fluid flow generator (2) can generate a first fluid flow (8) between the first fluid flow generator (2) and the first axial earpiece conduit (4) and between the first fluid flow generator (2) and the second axial earpiece conduit (13). As to particular embodiments, the first earpiece external surface (7) can be sealably engaged with the first external ear canal (5) and the second earpiece external surface (16) can be sealably engaged with the second external ear canal (14). The first fluid flow generator (2) can operate to generate a first fluid flow (8) which egresses from the first axial earpiece conduit (4) toward the first external ear canal (5) and from the second axial earpiece conduit (13) toward the second external ear canal (14), thereby generating a first pressure differential (9) having a first external ear canal pressure (10) greater than the ambient pressure (11) and a second pressure differential (17) having a second external ear canal pressure (18) greater than the ambient pressure (11). Similarly, the first fluid flow generator (2) can be operable to generate a first fluid flow (8) which ingresses to the first axial earpiece conduit (4) from the first external ear canal (5) and ingresses to the second axial earpiece conduit (13) from the second external ear canal (14), thereby generating a first pressure differential (9) having a first external ear canal pressure (10) lesser than the ambient pressure (11) and a second pressure differential (17) having a second external ear canal pressure (18) lesser than the ambient pressure (11).

As to particular embodiments having a first and second axial earpiece conduit (4)(13) fluidicly coupled in common to the first fluid flow generator (2), the first fluid flow generator (2) can be capable of generating a second pressure differential amplitude oscillation frequency (64) substantially similar to the first pressure differential amplitude oscillation frequency (48), as above described.

Now referring primarily to FIG. 27 through FIG. 35, as to particular embodiments, the external ear canal pressure regulation device (1) can include independent first and second fluid flow generators (2)(19) capable of generating discrete first and second fluid flows (8)(20). The second fluid flow generator (19) can be configured and fluidicly coupled to a second axial earpiece conduit (13) of a second earpiece (12) in substantially similar configuration as above described for first fluid flow generator (1) fluidicly coupled to the first axial earpiece conduit (4). Accordingly, the second fluid flow generator (19) can be capable of generating a corresponding discrete second fluid flow (20) independently regulated to generate a second pressure differential (17) having a second pressure differential amplitude (63) and having a second pressure differential amplitude oscillation frequency (64), all of which can have substantially similar ranges as for the first fluid flow (8), above described. Additionally, the second fluid flow generator (19) can be operatively regulated by a second pressure differential amplitude selection element (53) and a second pressure differential amplitude oscillation frequency selection element (54), both of which can be of substantially similar configuration to the corresponding first pressure differential amplitude selection element (40) and first pressure differential amplitude oscillation frequency selection element (50) which operatively regulate the first fluid flow generator (2), as described above.

As to particular embodiments having a second fluid flow generator (19), the external ear canal pressure regulation device (1) can further include a second pressure relief valve (66), which can be of substantially similar configuration to the first pressure relief valve (55), above described. The second pressure relief valve (66) can be fluidicly coupled to the second axial earpiece conduit (13) to relieve the second pressure differential (17) in excess of a second pre-selected pressure differential amplitude (67) of between 0 kilopascals to about 50 kilopascals.

As to particular embodiments having a second fluid flow generator (19), the external ear canal pressure regulation device (1) can further include a second pressure sensor (68), which can be of substantially similar configuration to the first pressure sensor (56), above described. The second pressure sensor (68) can generate a second pressure sensor signal (69) which can vary based upon change in the second external ear canal pressure differential amplitude (63). A second pressure sensor signal analyzer (70), which can be of substantially similar configuration to the first pressure sensor signal analyzer (58), as above described, can include a second pressure differential comparator (71) which functions to compare the second pre-selected pressure differential amplitude (67) to the sensed second pressure differential amplitude (63). The second pressure sensor signal analyzer (70) can generate a second pressure differential amplitude compensation signal (72), whereby a second fluid flow generator controller (73) can be responsive to the second pressure differential compensation signal (72) to control the second fluid flow generator (19) to achieve the second pre-selected pressure differential amplitude (63).

As to particular embodiments, the first fluid flow generator controller (41) and the second fluid flow generator controller (73) can be responsive to signals generated by a plurality of selection elements to control the corresponding first fluid flow generator (2) and the second fluid flow generator (19). As shown in the illustrative examples of FIG. 27 and FIG. 28, an external ear canal pressure regulation device (1) having a first fluid flow generator (2) and a second fluid flow generator (19) can be configured such that the first fluid flow generator controller (41) can be responsive to signals generated by a first selection element (187) and a second selection element (189) and the second fluid flow generator controller (73) can be responsive to signals generated by a third selection element (186) and a fourth selection element (188).

As to particular embodiments, the second pressure sensor signal analyzer (70) can further include a second pressure differential amplitude oscillation frequency comparator (135) which can function to compare a second pre-selected pressure differential amplitude oscillation frequency (180) to the second pressure differential amplitude oscillation frequency (64). The second pressure sensor signal analyzer (70) can generate a second pressure differential amplitude oscillation frequency compensation signal (181), whereby the second fluid flow generator controller (73) can be responsive to the second pressure differential amplitude oscillation frequency compensation signal (181) to control the second fluid flow generator (19) to achieve the second pre-selected pressure differential amplitude oscillation frequency (180).

Now referring primarily to FIG. 28, the external ear canal pressure regulation device (1) including a first fluid flow generator (2), a first earpiece (3) having a first axial earpiece conduit (4) fluidicly coupled to the first fluid flow generator (2) and a second earpiece (12) having a second axial earpiece conduit (13) fluidicly coupled to the second fluid flow generator (19) can be operable to generate a first pressure differential (9) in a first external ear canal (5) and a second pressure differential (17) in a second external ear canal (14) by generating corresponding discrete first and second fluid flows (8)(20), the first fluid flow (8) between the first fluid flow generator (2) and the first axial earpiece conduit (4) and the second fluid flow (20) between the second fluid flow generator (19) and the second axial earpiece conduit (13).

Now referring primarily to FIG. 28 and FIG. 40, as to particular embodiments of the external ear canal pressure regulation device (1) having the configuration shown in FIG. 27 through FIG. 35, to generate a first pressure differential (9) and a second pressure differential (17), valves V1, V2, V3L, V3R, V4, and V5 can be in the open condition and valves V6, 1L, and 1R can be in the closed condition. As to other particular embodiments, to only generate a first pressure differential (9) in the first external ear canal (5), valves V1, V3L, and V4 can be in the open condition and valves V2, V3R, V5, V6, 1L, and 1R can be in the closed condition. As to other particular embodiments, to only generate a second ear canal pressure differential (17) in the second external ear canal (14), valves V2, V3R, and V5 can be in the open condition and valves V1, V3L, V4, V6, 1L, and 1R can be in the closed condition.

As to particular embodiments having a first fluid flow generator (2) and a second fluid flow generator (19), each of the first and second fluid flow generators (2)(19) can include a corresponding first and second pair of fluid flow generators (74)(75) correspondingly fluidicly coupled to the first and second axial earpiece conduits (4)(13). Each of the first and second pair of fluid flow generators (74)(75) can include one positive pressure fluid flow generator (76) and one negative pressure fluid flow generator (77). The positive pressure fluid flow generators (76) can generate first and second fluid flows (8)(20) which egress from the corresponding first and second axial earpiece conduits (4)(13) toward the corresponding first and second external ear canals (5)(14). Accordingly, the first and second fluid flows (8)(20) can flow into the corresponding first and second external ear canals (5)(14), generating corresponding first and second pressure differentials (9)(17) whereby the corresponding first and second external ear canal pressures (10)(18) can be greater than the ambient pressure (11). The negative pressure fluid flow generators (77) can generate first and second fluid flows (8)(20) which ingress to the corresponding first and second axial earpiece conduits (4)(13) from the corresponding first and second external ear canals (5)(14). Accordingly, the first and second fluid flows (8)(19) can flow away from the corresponding first and second external ear canals (5)(14), generating corresponding first and second pressure differentials (9)(17) whereby the corresponding first and second external ear canal pressures (10)(18) can be lesser than the ambient pressure (11).

Now referring primarily to FIG. 8 and FIG. 9B, as to particular embodiments, a fluid flow temperature regulator (78) can be fluidicly coupled to the first fluid flow generator (2). The fluid flow temperature regulator (78) can be operated to generate a first fluid flow (8) or a second fluid flow (19) having a fluid flow temperature (79) greater than a body temperature (80). The first fluid flow (8) having a fluid flow temperature (79) greater than a body temperature (80) can flow through the first axial earpiece conduit (4) or the second axial earpiece conduit (13), egressing from the first axial earpiece conduit (4) or the second axial earpiece conduit (13) toward the corresponding first or second external ear canal (5)(14). Accordingly, the first fluid flow (8) having a fluid flow temperature (79) greater than a body temperature (80) can flow into the first external ear canal (5) or the second external ear canal (14).

Figure 29A:
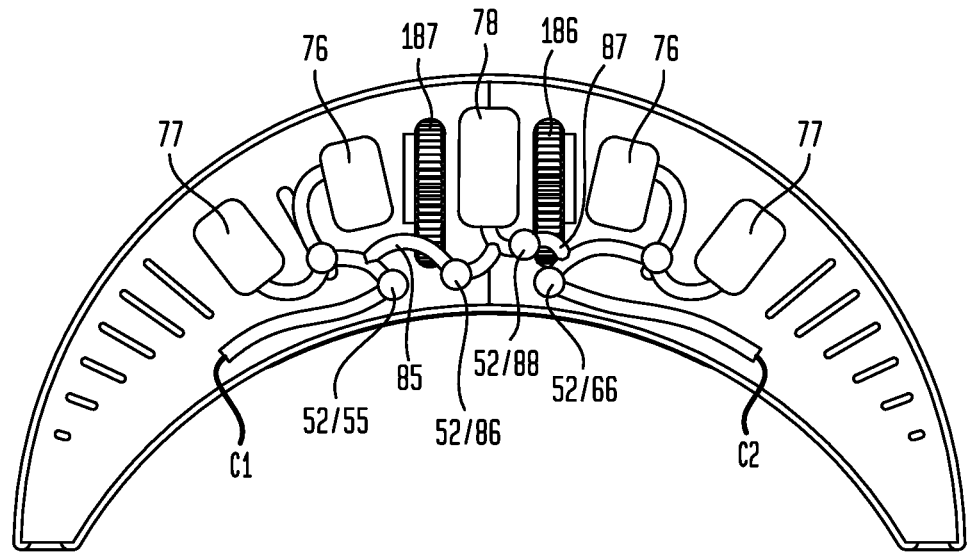
FIG. 29A is a first interior plan view of a particular embodiment of an external ear canal pressure regulation device.

Now referring primarily to FIG. 28 and FIG. 29A, the external ear canal pressure regulation device (1) can further include a fluid flow temperature regulator (78) fluidicly coupled to the first fluid flow (8) and the second fluid flow (20). The fluid flow temperature regulator (78) can be operable to regulate a fluid flow temperature (79) of the first fluid flow (8) or the second fluid flow (19), adjusting the fluid flow temperature (79) of the first fluid flow (8) or adjusting the fluid flow temperature (79) of the second fluid flow (20) to lesser or greater than a body temperature (80). Typically, the fluid flow temperature (79) can be in a range of between 10 degrees Celsius to about 50 degrees Celsius; however, embodiments can have a lesser or greater fluid flow temperature (79) depending upon the application.

Now referring primarily to FIG. 28 and FIG. 40, as to particular embodiments of the external ear canal pressure regulation device (1) having the configuration shown in FIG. 27 through FIG. 35, to generate a first pressure differential (9) in the first external ear canal (5) and regulate a fluid flow temperature (79) of the second fluid flow (20) in the second external ear canal (14), valves V1, V3L, V3R, V4, and 1R can be in the open condition and valves V2, V5, V6, and 1L can be in the closed condition. As to other particular embodiments, to generate a second pressure differential (17) in the second external ear canal (14) and regulate a first fluid flow temperature (79) of the first fluid flow (8) in the first external ear canal (5), valves V2, V3R, V3L, V5, and 1L can be in the open condition and valves V1, V4, V6, and 1R can be in the closed condition.

Now referring primarily to FIG. 28, the external ear canal pressure regulation device (1) can further include a third fluid flow generator (81) capable of generating a third fluid flow (82) having a third fluid flow rate (83) in a range of between 0 to about 10 liters per minute. As to particular embodiments, the third fluid flow generator (81) can be similar to the first and second fluid flow generators (2)(19) described above. As to particular embodiments, the fluid flow temperature regulator (78) can be fluidicly coupled to the third fluid flow generator (81), which can operate to regulate a third fluid flow temperature (84) of the third fluid flow (82). The third fluid flow generator (81) can be fluidicly coupled to the first and second axial earpiece conduits (4)(13), allowing the third fluid flow generator (81) to generate a third fluid flow (82) having a third fluid flow temperature (84) which can be delivered to the first and second external ear canals (5)(14) by the corresponding first and second axial earpiece conduits (4)(13).

Typically, the third fluid flow temperature (84) can be in a range of between 10 degrees Celsius to about 50 degrees Celsius; however, embodiments can have a lesser or greater third fluid flow temperature (84) depending upon the application. As to particular embodiments, the third fluid flow temperature (84) (or a third pre-selected fluid flow temperature) can be selected from one or more of the group including or consisting of: between about 10 degrees Celsius to about 20 degrees Celsius, between about 15 degrees Celsius to about 25 degrees Celsius, between about 20 degrees Celsius to about 30 degrees Celsius, between about 25 degrees Celsius to about 35 degrees Celsius, between about 30 degrees Celsius to about 40 degrees Celsius, between about 35 degrees Celsius to about 45 degrees Celsius, and between about 40 degrees Celsius to about 50 degrees Celsius.

One or a plurality of third fluid flow temperatures (84) (or third pre-selected fluid flow temperatures) can be generated with the external ear canal pressure regulation device (1) depending upon the method of use, which can be further influenced by factors such as user (33) anatomy, physiology, or biochemistry of the auditory meatus (34); disorder symptom targeted for alleviation; disorder targeted for treatment; observable effect(s) of using one or a plurality of third fluid flow temperatures (84) (or third pre-selected fluid flow temperatures) in a particular method of using the external ear canal pressure regulation device (1); or the like; or combinations thereof; whereby the one or the plurality of third fluid flow temperatures (84) (or third pre-selected fluid flow temperatures) can be effective to alleviate one or more disorder symptoms or treat one or more disorders, but not so much as to cause discomfort to the user (33) or injury to the auditory meatus (34) or the tympanic membrane (35).

Typically, the third fluid flow rate (83) can be in a range of between 0 liters per minute to about 10 liters per minute; however, embodiments can have a lesser or greater third fluid flow rate (83) depending upon the application. As to particular embodiments, the third fluid flow rate (83) (or a third pre-selected fluid flow rate) can be selected from one or more of the group including or consisting of: between about 0 liters per minute to about 2 liters per minute, between about 1 liter per minute to about 3 liters per minute, between about 2 liters per minute to about 4 liters per minute, between about 3 liters per minute to about 5 liters per minute, between about 4 liters per minute to about 6 liters per minute, between about 5 liters per minute to about 7 liters per minute, between about 6 liters per minute to about 8 liters per minute, between about 7 liters per minute to about 9 liters per minute, and between about 8 liters per minute to about 10 liters per minute.

One or a plurality of third fluid flow rates (83) (or third pre-selected fluid flow rates) can be generated with the external ear canal pressure regulation device (1) depending upon the method of use, which can be further influenced by factors such as user (33) anatomy, physiology, or biochemistry of the auditory meatus (34); disorder symptom targeted for alleviation; disorder targeted for treatment; observable effect(s) of using one or a plurality of third fluid flow rates (83) (or third pre-selected fluid flow rates) in a particular method of using the external ear canal pressure regulation device (1); or the like; or combinations thereof; whereby the one or the plurality of third fluid flow rates (83) can be in an amount effective to alleviate one or more disorder symptoms or treat one or more disorders, but not so much as to cause discomfort to the user (33) or injury to the auditory meatus (34) or the tympanic membrane (35).

Now referring primarily to FIG. 28 and FIG. 29A, particular embodiments of the external ear canal pressure regulation device (1) having a third fluid flow generator (81) can further include a first valved conduit (85) having a first valved conduit valve (86) which operably interrupts the third fluid flow (82) to the first axial earpiece conduit (4). In the open condition, the first valved conduit valve (86) allows the third fluid flow (82) to flow from the third fluid flow generator (81) toward the first axial earpiece conduit (4) and, accordingly, toward the first external ear canal (5). In the closed condition, the first valved conduit valve (86) precludes the third fluid flow (82) from flowing from the third fluid flow generator (81) toward the first axial earpiece conduit (4).

Again referring primarily to FIG. 28 and FIG. 29A, particular embodiments of the external ear canal pressure regulation device (1) having a third fluid flow generator (81) can further include a second valved conduit (87) having a second valved conduit valve (88) which operably interrupts the third fluid flow (82) to the second axial earpiece conduit (13). In the open condition, the second valved conduit valve (88) allows the third fluid flow (82) to flow from the third fluid flow generator (81) toward the second axial earpiece conduit (13) and, accordingly, toward the second external ear canal (14). In the closed condition, the second valved conduit valve (88) precludes the third fluid flow (82) from flowing from the third fluid flow generator (81) toward the second axial earpiece conduit (13).

Now referring primarily to FIG. 28 and FIG. 40, as to particular embodiments of the external ear canal pressure regulation device (1) having the configuration shown in FIG. 27 through FIG. 35, to generate a third fluid flow (82) having a third flow temperature (84) and a third fluid flow rate (83) in the first external ear canal (5) and the second external ear canal (14), valves V3L, V3R, 1L, 1R, and V6 can be in the open condition and valves V1, V2, V4, and V5 can be in the closed condition. As to other particular embodiments, to only generate a third fluid flow (82) having a third flow temperature (84) and a third fluid flow rate (82) in the first external ear canal (5), valves V3L, 1L, and V6 can be in the open condition and valves V1, V2, V3R, V4, V5, and 1R can be in the closed condition. As to other particular embodiments, to only generate a third fluid flow (82) having a third flow temperature (84) and a third fluid flow rate (83) in the second external ear canal (14), valves V3R, IR, and V6 can be in the open condition and valves V1, V2, V3L, V4, V5, and 1L can be in the closed condition.

Now referring primarily to FIG. 8, FIG. 9A, FIG. 28, and FIG. 29B, particular embodiments of the external ear canal pressure regulation device (1) can further include a manifold exhaust valve (89), which in the open condition, can allow the first fluid flow (8) or the second fluid flow (20) to egress from the fluid flow manifold (51) to the ambient pressure (11), thereby relieving the first or the second pressure differentials (9)(17).

Now referring primarily to FIG. 28 and FIG. 40, as to particular embodiments of the external ear canal pressure regulation device (1) having the configuration shown in FIG. 27 through FIG. 35, to exhaust the fluid flow manifold (51), valve V6 can be in the open condition and valves V1, V2, V3L, V3R, V4, V5, 1L, and 1R can be in the closed condition.

Now referring generally to FIG. 1 through FIG. 8 and FIG. 11 through FIG. 28, embodiments of the external ear canal pressure regulation device (1) can include a first or a second earpiece (3)(12) having compliant corresponding first or second earpiece external surface (7)(16) configured to correspondingly sealably engage a first or second external ear canal (5)(14), thus acting as a corresponding first or second barrier (102)(103) between the corresponding first or second external ear canal pressure (10)(18) and the ambient pressure (11). Embodiments of the first or second earpiece (3)(12) can be configured to sufficiently sealably engage with the first or second external ear canal (5)(14) to resist axial or lateral displacement in view of normal anatomical variations of the first or second external ear canal (5)(14) over a normal range of operating temperatures of between about 20° C. (about 68° F.) to about 50° C. (about 122° F.) and allow generation and maintenance of a normal range of operating pressures of between about −50 kilopascals below the ambient pressure (11) to about +50 kilopascals above the ambient pressure (11).

Now referring primarily to FIG. 11 through FIG. 18, as to particular embodiments, the first or second earpieces (3)(12) of the external ear canal pressure regulation device (1) can be formed from a compliant material which can correspondingly compressibly deform upon engagement with the corresponding first or second external ear canals (5)(14), thereby allowing the first or second earpieces (3)(12) to sealably conform to the corresponding first or second external ear canals (5)(14). As to these particular embodiments, the first or second earpieces (3)(12) can be formed, molded, three-dimensionally printed, or otherwise fabricated from any of a numerous and wide variety of materials capable of sealable engagement with the corresponding first or second external ear canals (5)(14), including or consisting of: a silicone, a foam (including polyurethane foam), a polyvinylsiloxane, a low durometer elastomer, or the like, or combinations thereof.

As to particular embodiments, the first or second earpieces (3)(12) can be generally uniform, formed from one material, for example a lesser durometer elastomer. As to other particular embodiments, the first or second earpieces (3)(12) can be formed from a plurality of layers, for example an inner core layer having a greater durometer surrounded by an outer layer having a lesser durometer or an inner core layer having a lesser durometer surrounded by an outer layer having a greater durometer.

As to particular embodiments, a portion of the first or second earpiece external surfaces (7)(16) can inwardly taper from an earpiece first end (92) approaching an earpiece second end (93). As an illustrative example of particular embodiments of this configuration, the first or second earpiece external surfaces (7)(16) can be configured in the general form of a truncated cone inwardly tapering approaching the earpiece second end (93). As to particular embodiments, the first or second earpiece external surfaces (7)(16) can further include a plurality of circumferential ribs disposed in spaced apart relation between the earpiece first end (92) and the earpiece second end (93).

The first or second earpiece external surfaces (7)(16) can remain sealably engaged with the corresponding first or second external ear canals (5)(14) by frictional forces between the first or second earpiece external surfaces (7)(16) and the corresponding first or second external ear canals (5)(14). As to particular embodiments, the first or second earpiece external surfaces (7)(16) can remain engaged with the corresponding first or second external ear canals (5)(14) by forcible urging against the external ear canal pressure regulation device (1) during normal operation. As to other particular embodiments, a retention element (182) can be coupled to the earpiece (3)(12) or the external ear canal pressure regulation device (1), which can be worn within the ear (6)(15), about the ear (6), about the head (95), or about the neck (183) to assist with retention of the earpiece (3)(14) within the external ear canal (5)(14).

Now referring primarily to FIG. 11 through FIG. 18, a retention element (182) can be provided as a resiliently flexible member (182) coupled about the earpiece (3)(14). As to particular embodiments, the resiliently flexible member (182) can be configured to be disposed within a concha area (183) of the ear (6)(15), which upon forcible urging into the concha area (183), can assist in retaining the earpiece (3)(14) within the external ear canal (5)(14). As to particular embodiments, the resiliently flexible member (182) can be configured as an arcuate annular member (184) having a plurality of radially disposed spokes (185).

Now referring primarily to FIG. 8, FIG. 9B, FIG. 10, FIG. 19 through FIG. 26, FIG. 28, and FIG. 29B, as to particular embodiments, the external ear canal pressure regulation device (1) can further include a fourth fluid flow generator (96) capable of generating a fourth fluid flow (99). The fourth fluid flow generator (96) can be configured substantially in the same manner as the first fluid flow generator (2) or the second fluid flow generator (19), as described above. A first coaxial earpiece conduit (97) can be disposed about the first axial earpiece conduit (4) and a second coaxial earpiece conduit (98) can be disposed about the second axial earpiece conduit (13) (as to those embodiments which include a second axial earpiece conduit (13)). The first and second coaxial earpiece conduits (4)(13) can be fluidicly coupled to the fourth fluid flow generator (96). A first elastomer sleeve (100) and a second elastomer sleeve (101) can be correspondingly disposed about the first and second axial earpiece conduits (4)(13) to provide the corresponding first and second earpiece external surfaces (7)(16) configured to correspondingly sealably engage the first and second external ear canals (5)(14) to provide the corresponding first and second barriers (102)(103) between the corresponding first and second external ear canal pressures (10)(18) and the ambient pressure (11). The first and second elastomer sleeves (100)(101) can be fluidicly coupled to the first and second coaxial earpiece conduits (97)(98). The fourth fluid flow (99) in the first and second coaxial earpiece conduits (97)(98) can generate corresponding first and second coaxial earpiece conduit pressure differentials (104)(105) between corresponding first and second coaxial earpiece conduit pressures (106)(107) and the ambient pressure (11). The first and second coaxial earpiece conduit pressure differentials (106)(107) can be capable of correspondingly expanding the first and second elastomer sleeves (100)(101) to correspondingly sealably engage the first and second external ear canals (5)(14).

Figure 29B:
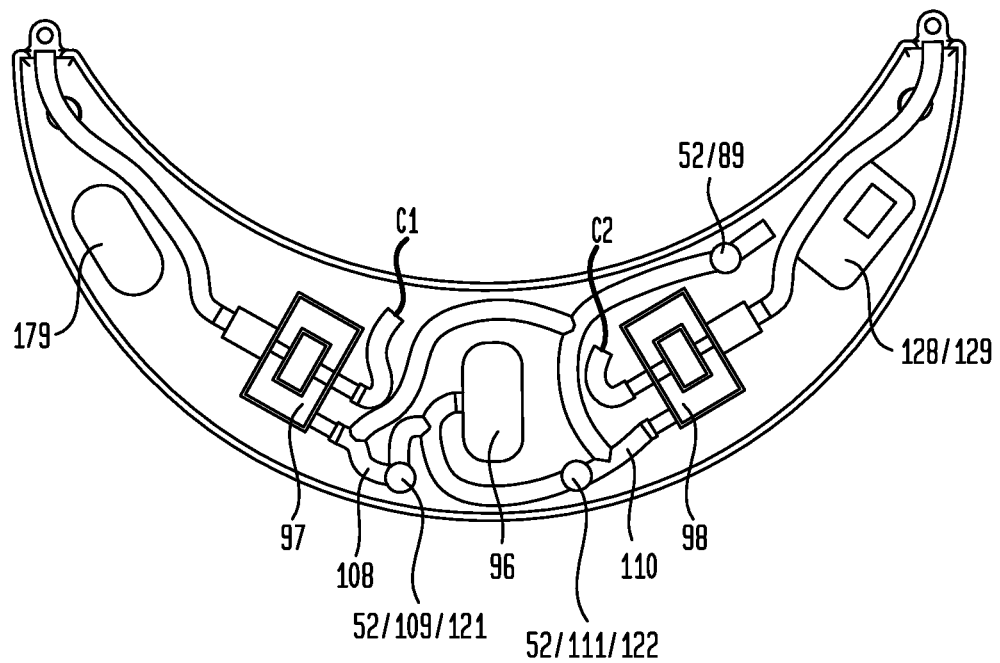
FIG. 29B is a second interior plan view of the particular embodiment of the external ear canal pressure regulation device shown in FIG. 29A.
Figure 30:
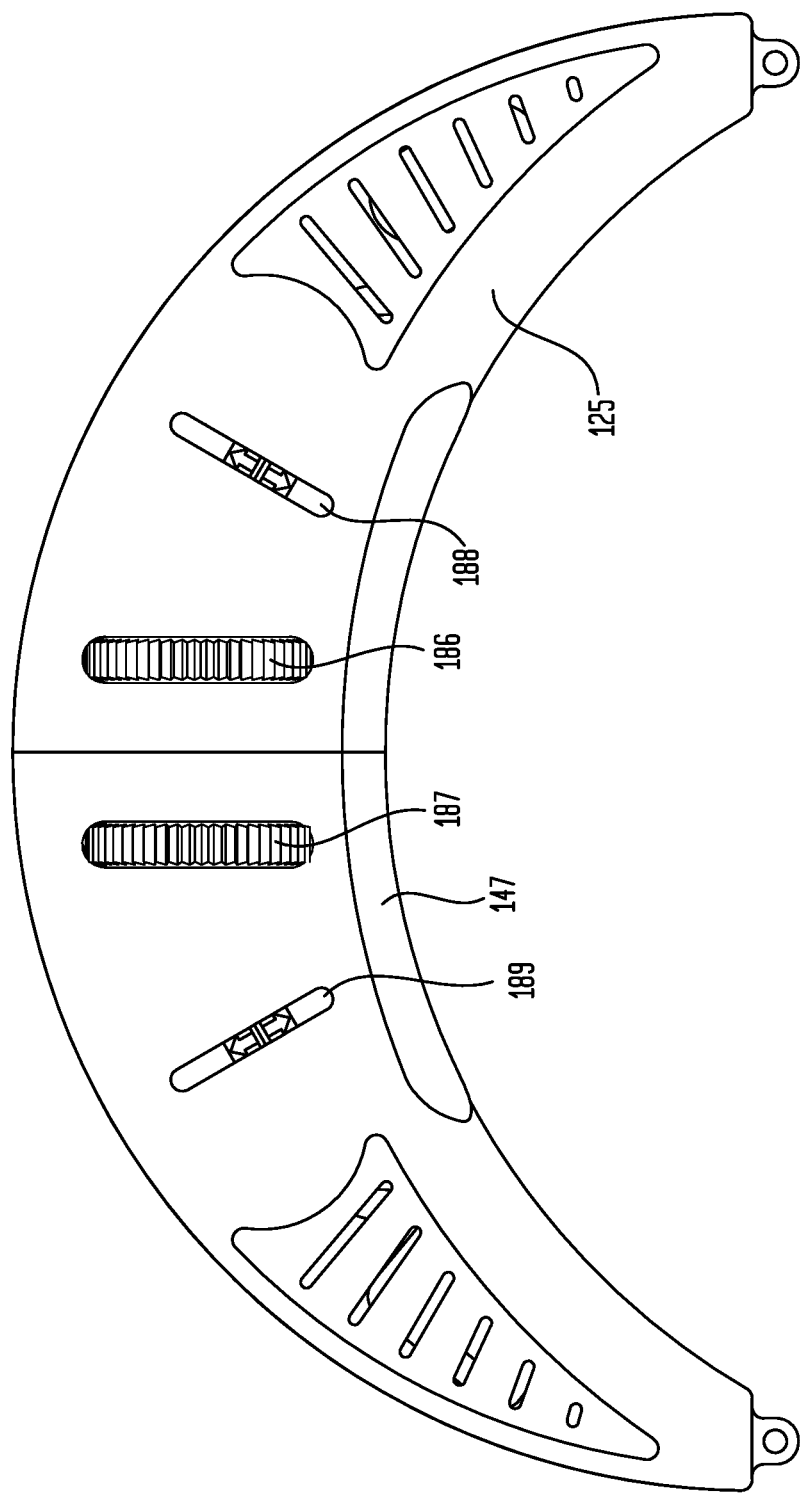
FIG. 30 is a top view of a particular embodiment of an external ear canal pressure regulation device.
Figure 31:
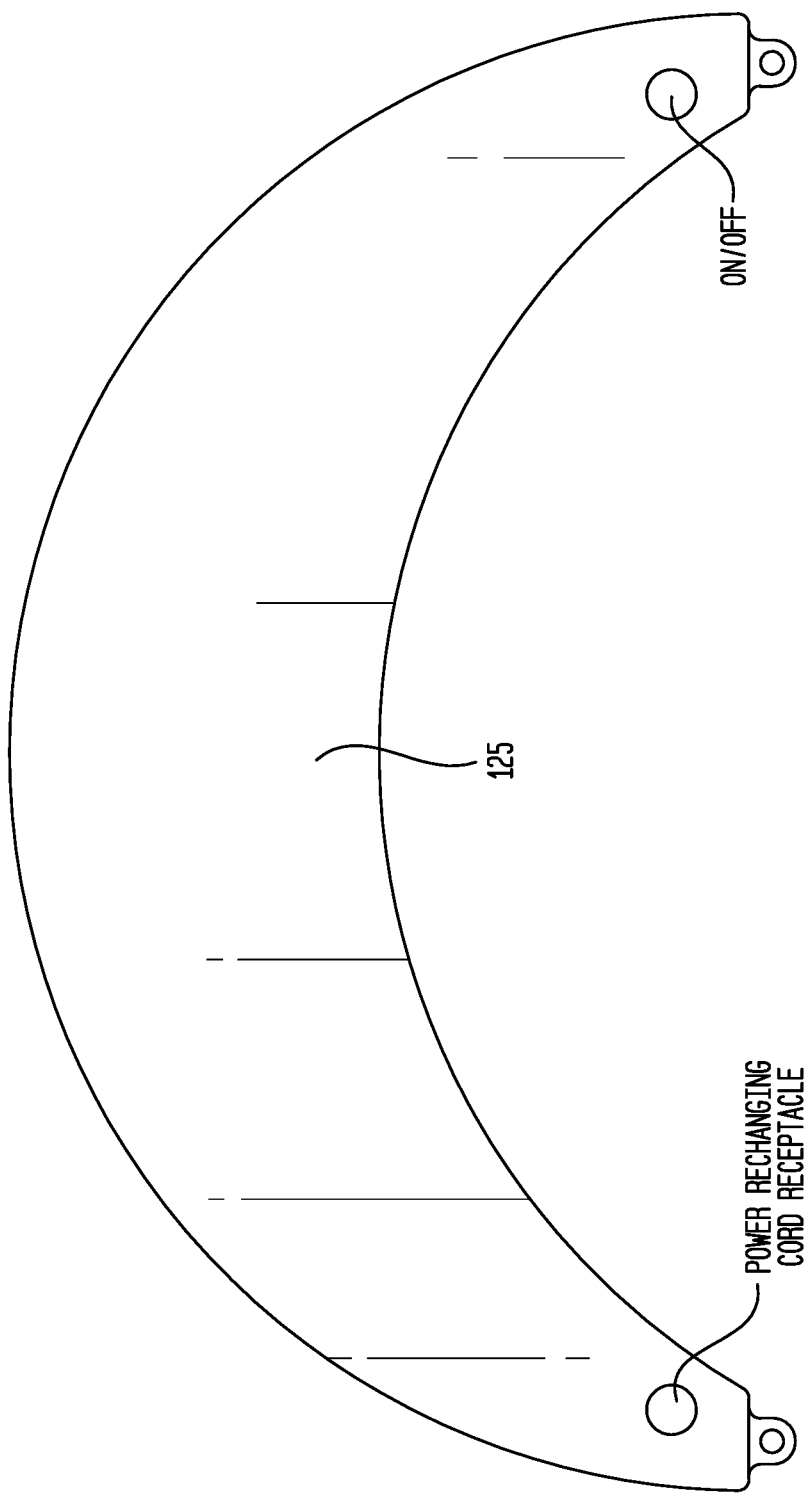
FIG. 31 is a bottom view of a particular embodiment of an external ear canal pressure regulation device.
Figure 34:
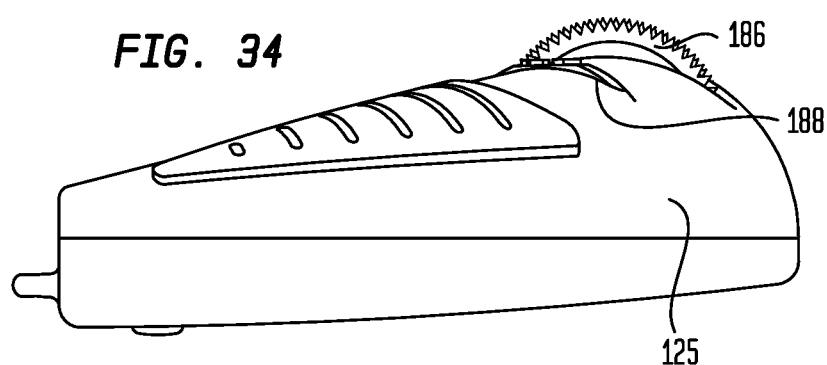
FIG. 34 is a first end view of a particular embodiment of an external ear canal pressure regulation device.
Figure 35:
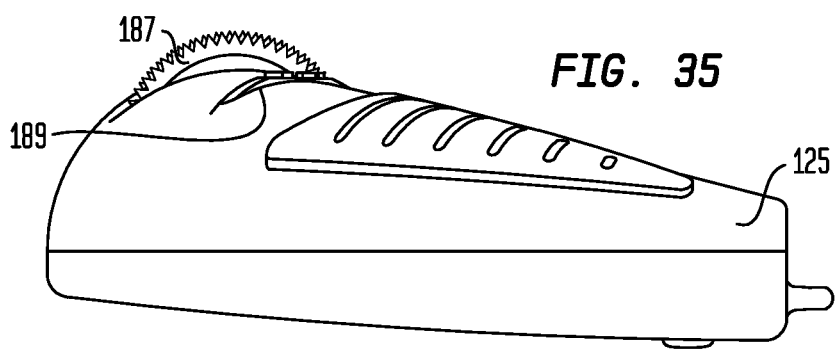
FIG. 35 is a second end view of a particular embodiment of an external ear canal pressure regulation device.

Now referring primarily to FIG. 28 and FIG. 29B, particular embodiments of the external ear canal pressure regulation device (1) having a fourth fluid flow generator (96) can further include a third valved conduit (108) having a third valved conduit valve (109) which operably interrupts the fourth fluid flow (99) to the first coaxial earpiece conduit (97). In the open condition, the third valved conduit valve (109) allows the fourth fluid flow (99) to flow from the fourth fluid flow generator (96) toward the first coaxial earpiece conduit (97) and, accordingly, toward the first elastomer sleeve (100). In the closed condition, the third valved conduit valve (109) precludes the fourth fluid flow (99) from flowing from the fourth fluid flow generator (96) toward the first elastomer sleeve (100).

Again referring primarily to FIG. 28 and FIG. 29B, particular embodiments of the external ear canal pressure regulation device (1) having a fourth fluid flow generator (96) can further include a fourth valved conduit (110) having a fourth valved conduit valve (111) which operably interrupts the fourth fluid flow (99) to the second coaxial earpiece conduit (98). In the open condition, the fourth valved conduit valve (111) allows the fourth fluid flow (99) to flow from the fourth fluid flow generator (96) toward the second coaxial earpiece conduit (98) and, accordingly, toward the second elastomer sleeve (101). In the closed condition, the fourth valved conduit valve (111) precludes the fourth fluid flow (99) from flowing from the fourth fluid flow generator (96) toward the second elastomer sleeve (101).

Now referring primarily to FIG. 28, the external ear canal pressure regulation device (1) can further include a fourth fluid flow generator controller (112) which can control operation of the fourth fluid flow generator (96) to generate the first and second coaxial earpiece conduit pressure differentials (104)(105) between the corresponding first and second coaxial earpiece conduit pressures (106)(107) and the ambient pressure (11) to expand the corresponding first and second elastomer sleeves (100)(101) to sealably engage the corresponding first and second external ear canals (5)(14), thereby providing the corresponding first and second barriers (102)(103) between the corresponding first and second external ear canal pressures (10)(18) and the ambient pressure (11).

Again referring primarily to FIG. 28, the external ear canal pressure regulation device (1) can further include a third pressure sensor (113) fluidicly coupled to the first coaxial earpiece conduit (97). The third pressure sensor (113) can generate a third pressure sensor signal (114) which varies based upon change in the first coaxial earpiece conduit pressure differential (104) between the first coaxial earpiece conduit pressure (106) and the ambient pressure (11).

Again referring primarily to FIG. 28, the external ear canal pressure regulation device (1) can further include a fourth pressure sensor (115) fluidicly coupled to the second coaxial earpiece conduit (98). The fourth pressure sensor (115) can generate a fourth pressure sensor signal (116) which varies based upon change in the second coaxial earpiece conduit pressure differential (105) between the second coaxial earpiece conduit pressure (107) and the ambient pressure (11).

Now referring primarily to FIG. 28, the external ear canal pressure regulation device (1) can further include a coaxial earpiece conduit pressure sensor signal analyzer (117) which functions to identify stable first and second coaxial earpiece conduit pressure differentials (104)(105) between the corresponding first and second coaxial earpiece conduit pressures (106)(107) and the ambient pressure (11). The coaxial earpiece conduit pressure sensor signal analyzer (117) can generate a seal signal (118) upon occurrence of the stable first and second coaxial earpiece conduit pressure differentials (104)(105).

Now referring primarily to FIG. 6, FIG. 8, FIG. 9A, and FIG. 28, particular embodiments of the external ear canal pressure regulation device (1) can further include an elastomer sleeve seal indicator (119) responsive to the seal signal (118). The elastomer sleeve seal indicator (119) can generate a sensorial perceivable indicia (120) upon receiving the seal signal (118). The sensorial perceivable indicia (120) can include one or more of a sound indicia, a light indicia, a tactile indicia, or the like, or combinations thereof.

Now referring primarily to FIG. 28 and FIG. 29B, the external ear canal pressure regulation device (1) can further include third and fourth pressure relief valves (121)(122) correspondingly fluidicly coupled to the first and second coaxial earpiece conduits (97)(98). In the open condition, the third and fourth pressure relief valves (121)(122) can correspondingly relieve the first and second coaxial earpiece conduit pressure differentials (104)(105) between the corresponding first and second coaxial earpiece conduit pressures (106)(107) and the ambient pressure (11).

Now referring primarily to FIG. 8, the external ear canal pressure regulation device (1) can further include a pressure release selection element (123). The fourth fluid flow generator controller (112) can be responsive to operation of the pressure release selection element (123) to curtail operation of the fourth fluid flow generator (96) and operate the third and fourth pressure relief valves (121)(122) to correspondingly return the first and second coaxial earpiece conduit pressure differentials (104)(105) between the corresponding first and second coaxial earpiece conduit pressures (106) (107) and the ambient pressure (11) toward the ambient pressure (11) to contract the corresponding first and second elastomer sleeves (100)(101).

Now referring primarily to FIG. 37A through FIG. 39E, which provide graphs of pressure regulation profiles (136) which can be administered by embodiments of the external ear canal pressure regulation device (1) effective to alleviate one or more disorder symptoms or treat one or more disorders. Each graph shows a pressure differential (9)(17) between the external ear canal pressure (10)(18) and the ambient pressure (11) achieved over a time period (39). As to particular embodiments, a fluid flow generator (2)(19) can be operated to generate a fluid flow (8)(20) which egresses from an axial earpiece conduit (4)(13) toward an external ear canal (5)(14) over a time period (39), resulting in a positive external ear canal pressure (10)(18) relative to the ambient pressure (11) (as shown in the examples of FIG. 37A through FIG. 37G). As to other particular embodiments, a fluid flow generator (2)(19) can be operated to generate a fluid flow (8)(20) which ingresses to an axial earpiece conduit (4)(13) from an external ear canal (5)(14) toward the fluid flow generator (2)(19) over a time period (39), resulting in a negative external ear canal pressure (10)(18) relative to the ambient pressure (11) (as shown in the examples of FIG. 38A through FIG. 38G).

Figure 38A:
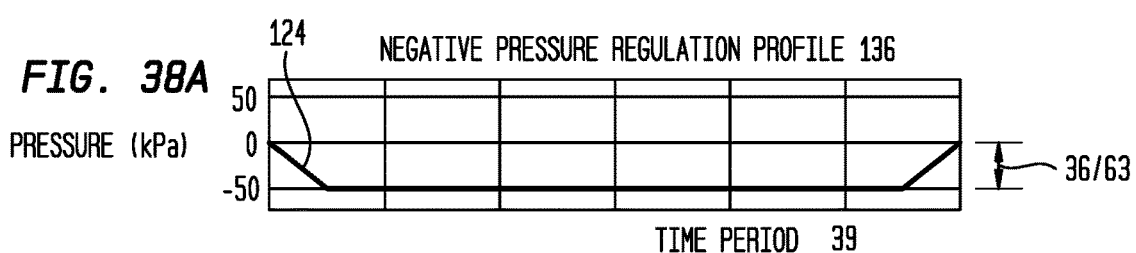
FIG. 38A is a negative pressure regulation profile which can be generated by a particular embodiment of an external ear canal pressure regulation device.

Now referring primarily to FIG. 37A and FIG. 38A, the fluid flow generator (2)(19) can be operated to maintain a constant external ear canal pressure (10)(18) over a time period (39). As to particular embodiments, a constant external ear canal pressure (10)(18) can be maintained as a fluid volume (21) within the external ear canal (5)(14) over the time period (39) without (or substantially without) a fluid flow (8)(20). As an illustrative example, the external ear canal pressure regulation device (1) having an earpiece external surface (7)(16) sealably engaged within an external ear canal (5)(14), as described above, can be operated by control of the fluid flow generator (2)(19) to generate a fluid flow (2)(19) having a fluid volume (21) or a pre-selected fluid volume (22) between the fluid flow generator (2)(19) and the external ear canal (5)(14) through the axial earpiece conduit (4)(13) of the earpiece (3)(12) to achieve a pressure differential (9)(17) between the external ear canal pressure (10)(18) and the ambient pressure (11). Once the desired fluid volume (21) or pre-selected fluid volume (22) establishes a pressure differential (9)(17), the pressure differential (9)(17) can be maintained for a time period (39) without or substantially without additional fluid flow (8)(20) due to sealable engagement of the earpiece external surface (7)(16) with the external ear canal (5)(14). As to other embodiments, once the desired pressure differential (9)(17) has been achieved, the pressure differential (9)(17) can be maintained for a time period (39) by additional fluid flow (8)(20) to or from the external ear canal (5)(14) to offset leakage about engagement of the earpiece external surface (7)(16) with the external ear canal (5)(14). As to other embodiments, the external ear canal pressure (10)(18) can be maintained for a time period (39) by continuous fluid flow (8)(20) to the external ear canal (5)(14).

Regardless of the method, the external ear canal pressure (10)(18) can be maintained constant over a time period (39) in a range of between about +50 kilopascals above the ambient pressure (11) to about −50 kilopascals below the ambient pressure (11) to alleviate one or more disorders symptom or treat one or more disorders. A positive external ear canal pressure (10)(18) relative to the ambient pressure (11) can be achieved by maintaining the external ear canal pressure (10)(18) in a range of between about 0 kilopascals to about +50 kilopascals above the ambient pressure (11). Alternatively, a negative external ear canal pressure (10)(18) relative to the ambient pressure (11) can be achieved by maintaining the external ear canal pressure (10)(18) in a range of between about −50 kilopascals to about 0 kilopascals below the ambient pressure (11).

Now referring primarily to FIG. 37B through FIG. 37G, FIG. 38B through FIG. 38G, and FIG. 39A through FIG. 39E, the fluid flow generator (2)(19) can be configured to generate a fluid flow (8)(20) having a pressure differential wave (124) defining for each instant in the time period (39) a pre-selected pressure differential amplitude (37)(67) and a pre-selected pressure differential amplitude oscillation frequency (49)(180). As to particular embodiments, the fluid flow generator (2)(19) can be operated to generate a fluid flow (8)(20) which egresses from the axial earpiece conduit (4)(13) toward the external ear canal (5)(14) over a time period (39) having a pressure differential wave (124) including a pre-selected pressure differential amplitude (37)(67) and a pre-selected pressure differential amplitude oscillation frequency (49)(180) which results in a positive external ear canal pressure (10)(18) relative to the ambient pressure (11) (as shown in the examples of FIG. 37B through FIG. 37G).

As to other particular embodiments, the fluid flow generator (2)(19) can be operated to generate a fluid flow (8)(20) which ingresses to the axial earpiece conduit (4)(13) from the external ear canal (5)(14) toward the fluid flow generator (2)(19) over a time period (29) having a pressure differential wave (124) including a pre-selected pressure differential amplitude (37)(67) and a pre-selected pressure differential amplitude oscillation frequency (49)(180) which results in a negative external ear canal pressure (10)(18) relative to the ambient pressure (11) (as shown in the examples of FIG. 38B through FIG. 38G).

As to other particular embodiments, a fluid flow generator (2)(19) can be operated to generate a fluid flow (8)(20) which can alternate between egress from the axial earpiece conduit (4)(13) toward the external ear canal (5)(14) and ingress to the axial earpiece conduit (4)(13) from the external ear canal (5)(14) toward the fluid flow generator (2)(19) over a time period (39) having a pressure differential wave (124) including a pre-selected pressure differential amplitude (37)(67) and a pre-selected pressure differential amplitude oscillation frequency (49)(180) which results in generating an external ear canal pressure (10)(18) which alternates between positive and a negative external ear canal pressure (10)(18) relative to the ambient pressure (11) (as shown in the examples of FIG. 39A through FIG. 39E).

As to other particular embodiments, the pressure differential wave (124) can oscillate with a pre-selected pressure differential amplitude oscillation frequency (49)(180) within a pre-selected pressure differential amplitude (37)(67) in a range of between 0 kilopascals to about +50 kilopascals above the ambient pressure (11) (as shown in the examples of FIG. 37B through FIG. 37G).

As to yet other particular embodiments, the pressure differential wave (124) can oscillate with a pre-selected pressure differential amplitude oscillation frequency (49)(180) in a range of between about −50 kilopascals to 0 kilopascals below the ambient pressure (11)(as shown in the examples of FIG. 38B through FIG. 38G).

Figure 38B:
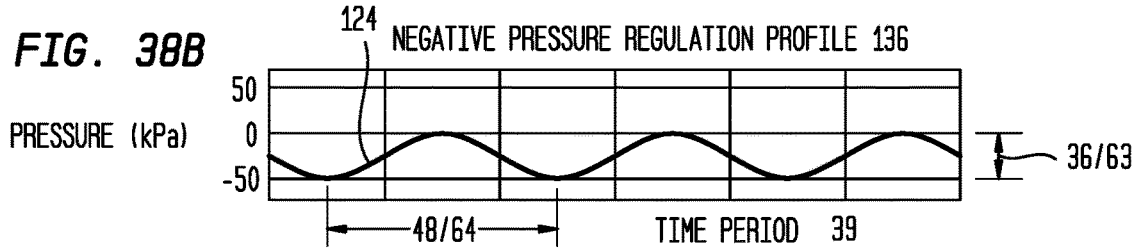
FIG. 38B is a negative pressure regulation profile which can be generated by a particular embodiment of an external ear canal pressure regulation device.
Figure 38C:
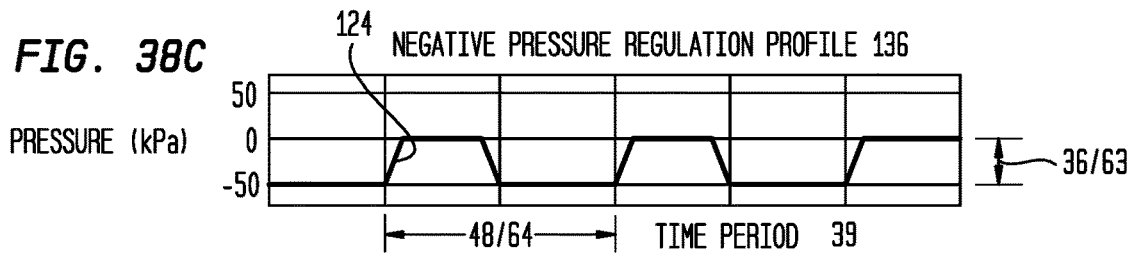
FIG. 38C is a negative pressure regulation profile which can be generated by a particular embodiment of an external ear canal pressure regulation device.
Figure 38D:
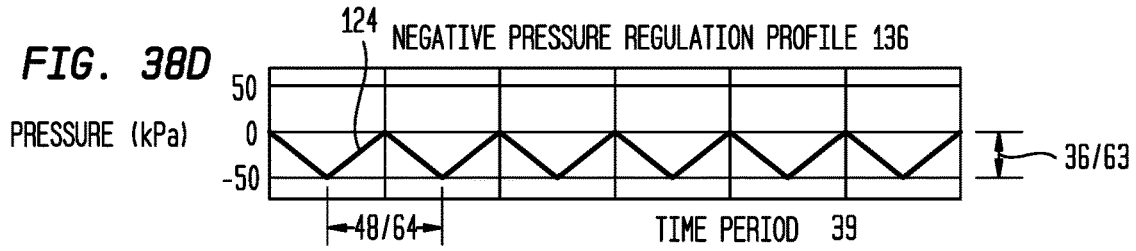
FIG. 38D is a negative pressure regulation profile which can be generated by a particular embodiment of an external ear canal pressure regulation device.
Figure 38E:
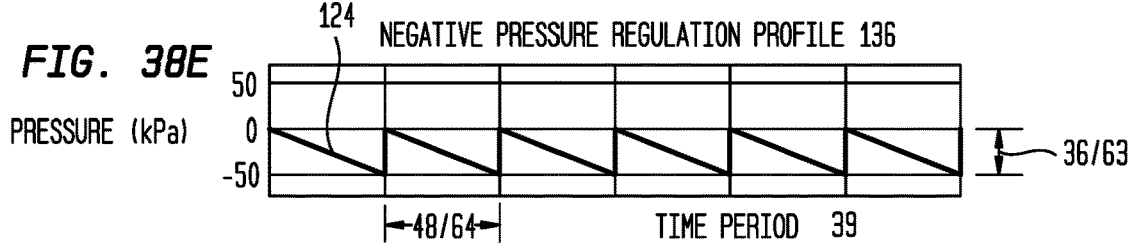
FIG. 38E is a negative pressure regulation profile which can be generated by a particular embodiment of an external ear canal pressure regulation device.
Figure 38F:
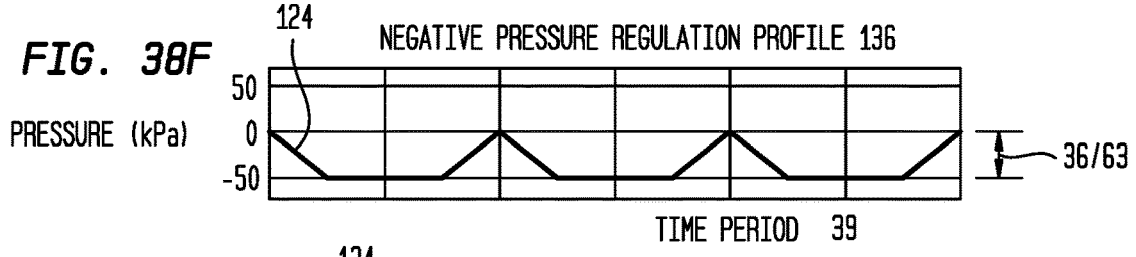
FIG. 38F is a negative pressure regulation profile which can be generated by a particular embodiment of an external ear canal pressure regulation device.
Figure 38G:
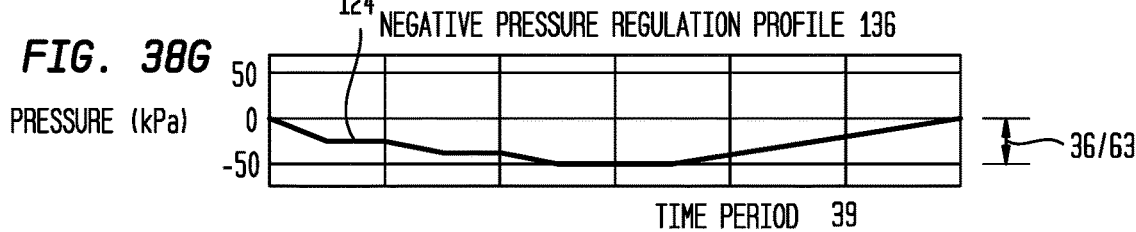
FIG. 38G is a negative pressure regulation profile which can be generated by a particular embodiment of an external ear canal pressure regulation device.

Again referring primarily to FIG. 37B through FIG. 37G, FIG. 38B through FIG. 38G, and FIG. 39A through FIG. 39E, the pressure differential wave (124) can have a numerous and wide variety of waveforms, depending upon the application, corresponding to the numerous and wide variety of disorder symptoms which can be alleviated or disorders which can be treated by operation of the external ear canal pressure regulation device (1). As illustrative examples, the pressure differential wave (124) can be sine wave having smooth repetitive periodic oscillations (as shown in the example of FIG. 37B, FIG. 38B, and FIG. 39A), a square wave in which the pressure differential wave (124) alternates at a steady frequency between fixed minimum and maximum values, a rectangular wave, a trapezoidal wave or a truncated wave in which the apex of the pressure differential wave (124) has a constant pre-selected pressure differential amplitude (37)(67) over a time period (39) (as shown in the example of FIG. 37C, FIG. 37F, FIG. 38C, FIG. 38F, and FIG. 39B), a triangle wave having linear leading and trailing edges (as shown in the example of FIG. 37D, FIG. 38D, and FIG. 39C), a sawtooth wave in which the leading edge has a pre-selected pressure differential amplitude (37)(67) which changes over a greater time period (39) as compared to the trailing edge (as shown in the example of FIG. 37E and FIG. 39D), a reverse sawtooth wave in which the leading edge changes pre-selected pressure differential amplitude (37)(67) over a lesser time period (39) as compared to the trailing edge (as shown in the example of FIG. 37E and FIG. 39E), or combinations thereof (as shown in the example of FIG. 37G and FIG. 38G).

Now referring primarily to FIG. 6, FIG. 7, FIG. 9A, FIG. 9B, and FIG. 29A through FIG. 35, as to particular embodiments, the external ear canal pressure regulation device (1) can further include a housing (125) having a housing internal surface (126) defining a hollow internal space (127) in which components of the external ear canal pressure regulation device (1) can be housed.

While the fluid flow generators (2)(19) of the external ear canal pressure regulation device (1) above described typically deliver a fluid flow (8)(20) of air to the external ear canal (5)(14) to achieve the pressure differential (9)(17) between the external ear canal pressure (10)(18) and the ambient pressure (11), this is not intended to be limiting with respect to the wide variety of fluids which can be delivered to the external ear canal (5)(14) by embodiments of the external ear canal pressure regulation device (1). As illustrative examples, the wide variety of fluids can include: a purified gas, such as oxygen, nitrogen, argon, or the like; a mixture of partial pressures of gases; a liquid, such as water, oil, alcohol, or the like; or combinations thereof.

Additionally, while the fluid flow (8)(20)(82)(99) (or other fluid flows) or the transfer of a fluid volume (21)(22) between components of the external ear canal pressure regulation device (1), between components of the external ear canal pressure regulation device (1) and the external ear canal (5)(14), or between components of the external ear canal pressure regulation device (1) and the ambient pressure (11) can be above described as typically between a first point and a second point for the purpose of brevity, the fluid flow (8)(20)(82)(99) (or other fluid flows) or the transfer of a fluid volume (21)(22) includes all points within the manifold fluid flow path (54) between the first point and the second point.

Now referring primarily to FIG. 8 and FIG. 28, embodiment of the external ear canal pressure regulation device (1) can further include a controller (128). The controller (128), as to particular embodiments, can take the form of a single integrated circuit (129) containing a processor (130) in communication with a memory element (131). The memory element (131) can be in the form of a non-volatile computer storage medium that can be erased and reprogrammed and as to particular embodiments a random access memory for data storage. The memory element (131) can contain a computer code (132) executable to provide specified functions or combinations of steps for performing the specified functions to operate the various components of the external ear canal pressure regulation device (1) in accordance with embodiments of the invention above described.

The block diagrams and flowchart illustrations shown in FIG. 8 and FIG. 28 support combinations of elements for performing the specified functions, combinations of steps for performing the specified functions, and executable program elements for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions.

Now referring primarily to FIG. 8, the computer code (132) can include a first fluid flow generator controller (41) which can be executed to transform a pressure differential amplitude selection signal (133) received from the first fluid pressure differential amplitude selection element (40) to correspondingly control the first fluid flow generator (2) to produce the first fluid flow (8) which egresses from the first axial earpiece conduit (4). As to particular embodiments, the first fluid flow generator controller (41) increases or decreases the first fluid flow (8) based on variation in the pressure differential amplitude selection signal (133). As to other embodiments, the first fluid pressure differential amplitude selection element (40) can be used to select a pre-selected fluid volume (22) and the first fluid flow generator controller (41) can correspondingly control the first fluid flow generator (2) to deliver the pre-selected fluid volume (22), as above described.

As to particular embodiments of the external ear canal pressure regulation device (1), which include a first pressure sensor (56), the computer code (132) can further include a first pressure sensor signal analyzer (58) executable to provide a first pressure differential amplitude comparator (59) which functions to compare a first pre-selected pressure differential amplitude (37) selected by user interaction with the pressure differential amplitude selection element (40) to the first pressure differential amplitude (36) sensed in the first axial earpiece conduit (4). The first pressure sensor signal analyzer (58) can be further executed to provide a first pressure differential amplitude compensation signal (60) which varies based upon the difference between the first pre-selected pressure differential amplitude (37) and the sensed first pressure differential amplitude (36). The first fluid flow generator controller (41) can be responsive to the first pressure differential amplitude compensation signal (60) to control the first fluid flow generator (2) to achieve the first pre-selected pressure differential amplitude (37).

Again referring primarily to FIG. 8, the first fluid flow generator controller (41) can be further executed to transform a pressure differential amplitude oscillation frequency selection signal (134) received from the first pressure differential amplitude oscillation frequency selection element (50) to correspondingly control the first fluid flow generator (2) to produce a first pressure differential amplitude oscillation (45) which reciprocally drives the first fluid flow (8) between a first fluid flow first direction (46) and a first fluid flow second direction (47) in the first axial earpiece conduit (4).

As to particular embodiments, the first fluid flow generator controller (41) varies a first pressure differential amplitude oscillation frequency (48) based on variation in the pressure differential amplitude oscillation frequency selection signal (134). As to other embodiments, the first pressure differential amplitude oscillation frequency selection element (50) can be used select a first pre-selected pressure differential amplitude oscillation frequency (49) and the first fluid flow generator controller (41) can correspondingly control the first fluid flow generator (2) to deliver the first pre-selected pressure differential amplitude oscillation frequency (49) in the ranges as above described.

As to particular embodiments of the external ear canal pressure regulation device (1), which include the first pressure sensor (56), the first pressure sensor signal analyzer (58) can be further executable to provide a first pressure differential amplitude oscillation frequency comparator (61) which functions to compare a first pre-selected pressure differential amplitude frequency (49) selected by user interaction with the first pressure differential amplitude oscillation frequency selection element (50) to the first pressure differential amplitude oscillation frequency (48) sensed in the first axial earpiece conduit (4). The first pressure sensor signal analyzer (58) can be further executed to provide a first pressure differential amplitude oscillation frequency compensation signal (62) which varies based upon the difference between the first pre-selected pressure differential amplitude oscillation frequency (49) and the sensed first pressure differential amplitude oscillation frequency (48). The first fluid flow generator controller (41) can be responsive to the first pressure differential amplitude compensation signal (62) to control the first fluid flow generator (2) to achieve the first pre-selected pressure differential frequency (49).

With respect to particular embodiments of the first fluid flow generator (2) as shown by the illustrative examples of FIG. 8 and FIG. 9B, the first fluid flow generator controller (41) can indirectly control the function of first fluid flow generator (2) by controlling the movement of a linear actuator (30) coupled to a piston (26) movable within a barrel (27), as above described.

With respect to particular embodiments as shown the illustrative examples of FIG. 28, FIG. 29A, and FIG. 29B, the external ear canal pressure regulation device (1) can include a first fluid flow generator (2) which operates to deliver a first fluid flow (8) to the first axial earpiece conduit (4) and a second fluid flow generator (19) which operates to deliver a discrete second fluid flow (20) to the second axial earpiece conduit (13) sensed by a second pressure sensor (68), as above described. Correspondingly, the computer code (132) can further include a second fluid flow generator controller (73) and a second pressure sensor signal analyzer (70) including a second pressure differential amplitude comparator (71) and a second pressure differential amplitude oscillation frequency comparator (135), each of which can function to control operation of the second fluid flow generator (19), as above described for the first fluid flow generator (2), which allows independent control of a second pressure differential amplitude (63) and second pressure differential amplitude oscillation frequency (64) in the second axial earpiece conduit (13).

Again referring primarily to FIG. 28, FIG. 29A, and FIG. 29B, the first fluid flow generator (2) and the second fluid flow generator (19) can each include a positive fluid flow generator (76) and a negative fluid flow generator (77) each discretely controllable to achieve the a first and second pressure differential amplitudes (36)(63) and first and second pressure differential amplitude oscillation frequencies (48)(64). Accordingly, the first and second fluid flow generator controllers (41)(73) can be executed to discretely control each positive fluid flow generator (76) and each negative fluid flow generator (77) of the first and second fluid flow generators (2)(19) to achieve the first and second pressure differential amplitudes (36)(63) and first and second pressure differential amplitude oscillation frequencies (48)(64).

Now referring primarily to FIG. 28, FIG. 37A through FIG. 37G, FIG. 38A through FIG. 38G, and FIG. 39A through FIG. 39E, particular embodiments of the computer code (132) further include a timer module (137) responsive to a time period selection element (190) and a pressure regulation profile administration module (138) responsive to a pressure regulation profile selection element (139) which allows selection of one of a plurality of pressure regulation profiles (136) contained in the memory element (131), as above described and as shown in the Figures, or as otherwise programmed and contained in the memory element (131). The pressure regulation profile administration module (138) functions to coordinate operation of the first and second fluid flow generators (2)(19) to achieve the first or second pre-selected pressure differential amplitudes (37)(67) corresponding to each time point within a time period (39) of the selected one of the plurality of pressure regulation profiles (136).

Now referring primarily to FIG. 8 and FIG. 28, as to particular embodiments, the computer code (132) can further include a fluid flow temperature regulator controller (140) which functions to control the fluid temperature regulator (78) to adjust fluid flow temperature (79) of the first or second fluid flows (8)(20). As to the illustrative embodiment shown in FIG. 8, the fluid flow temperature regulator controller (140) actuates the fluid flow temperature regulator (78) to increase fluid flow temperature (78) of the first fluid flow (8) for a time period (39) upon actuation of the first fluid flow generator (2).

As to the illustrative embodiment shown in FIG. 28, the fluid flow temperature regulator controller (140) can be executed to transform a fluid flow temperature selection signal (141) received from a fluid flow temperature selection element (142) to correspondingly control the fluid flow temperature regulator (78) to adjust the fluid flow temperature (79) of a third fluid flow (82) within a range of about a range of 10° C. and 50° C., as above described. As to these embodiments, the computer code (132) can further include a third fluid flow controller (143) which functions to control the third fluid flow (82) from a third fluid flow generator (81) to a third fluid flow rate (83) of between 0 and about 10 liters per minute, as above described.

Now referring to primarily to FIG. 8 and FIG. 28, the computer code (132) can further include a fourth fluid flow generator controller (112) executable to control the fourth fluid flow generator (96), as above described, to expand a first elastomer sleeve (100) or a second elastomer sleeve (101) correspondingly fluidicly coupled to the first or second coaxial earpiece conduit (97)(98) to correspondingly sealably engage the first or second external ear canal (5)(14) to provide the corresponding first or second barrier (102)(103) between the corresponding first or second external ear canal pressure (10)(18) and the ambient pressure (11). As to these embodiments, the computer code (132) can further include a coaxial earpiece conduit pressure sensor signal analyzer (117) executable to identify stable first and second coaxial earpiece conduit pressure differentials (104)(105) between the corresponding first and second coaxial earpiece conduit pressures (106)(107) and the ambient pressure (11). The third pressure sensor signal analyzer (117) can generate a seal signal (118) upon occurrence of the stable first and second coaxial earpiece conduit pressure differentials (104) (105) to generate the sensorial perceivable indicia (120), as above described. As these embodiments, the computer code (132) can further include a seal release module (144) executable in response to operation of a seal release selection element (145) to operate the pressure relief valve (121) (122), as above described.

Now referring primarily to FIG. 40, the computer code (132) further includes a valve control module (146) executable to actuate one or more of the valves (52) depending on a selected method of administering fluid flow (8)(20)(82) (99) within embodiments of the external ear canal pressure regulation device (1), as above described.

Now referring primarily to FIGS. 28 and 32, particular embodiments further include a graphical display surface (147) and the computer program (132) can further include a graphical user interface module (148) which can be executed to depict a graphical user interface (149) on the graphical display surface (147). The graphical user interface (149) by user interaction can execute functions of the computer code (132) to operate the external ear canal pressure regulation device (1). While user interaction will typically be in the form of a touch by the user (33) on a control image (150) depicted the graphical display surface (147), this illustrative example is not intended to preclude any command by a user (33) by which a function of the computer code (132) can be activated, executed or performed whether through selection of one or a plurality of control image(s) (150), or by user voice command, keyboard stroke, mouse button, or otherwise.

Figure 2:
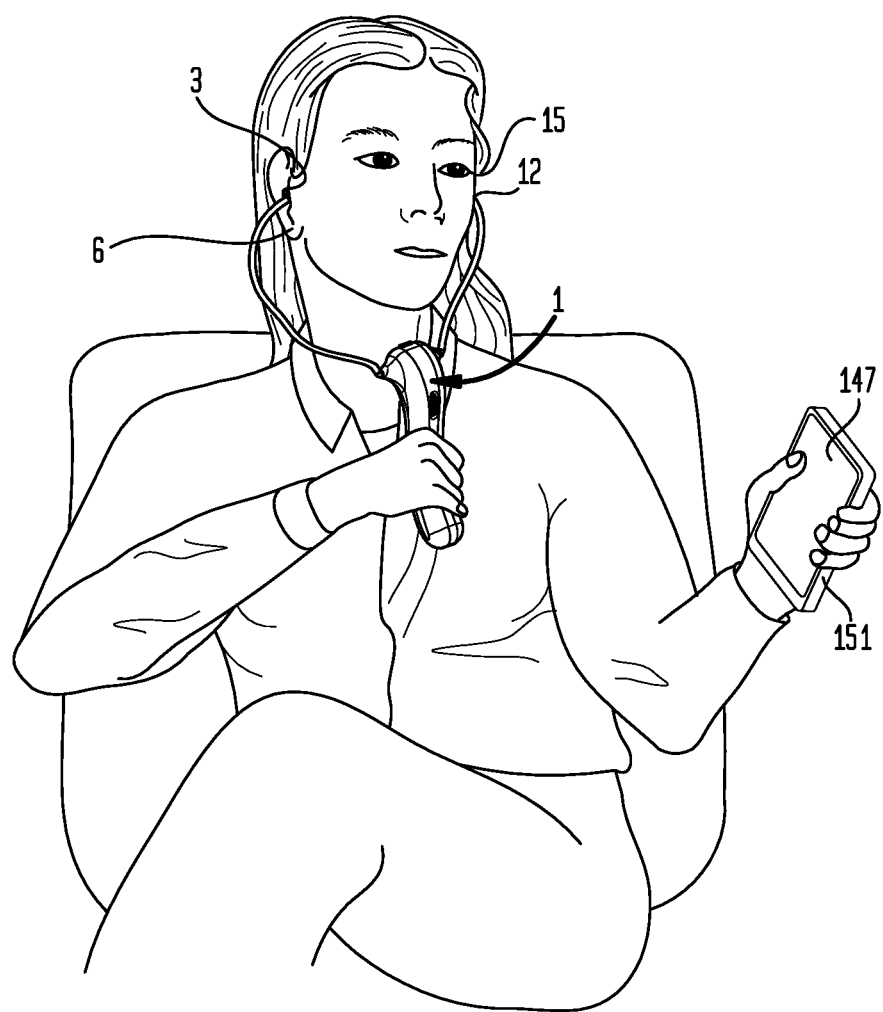
FIG. 2 is an illustration of a method of using a particular embodiment of the external ear canal pressure regulation device.
Figure 3:
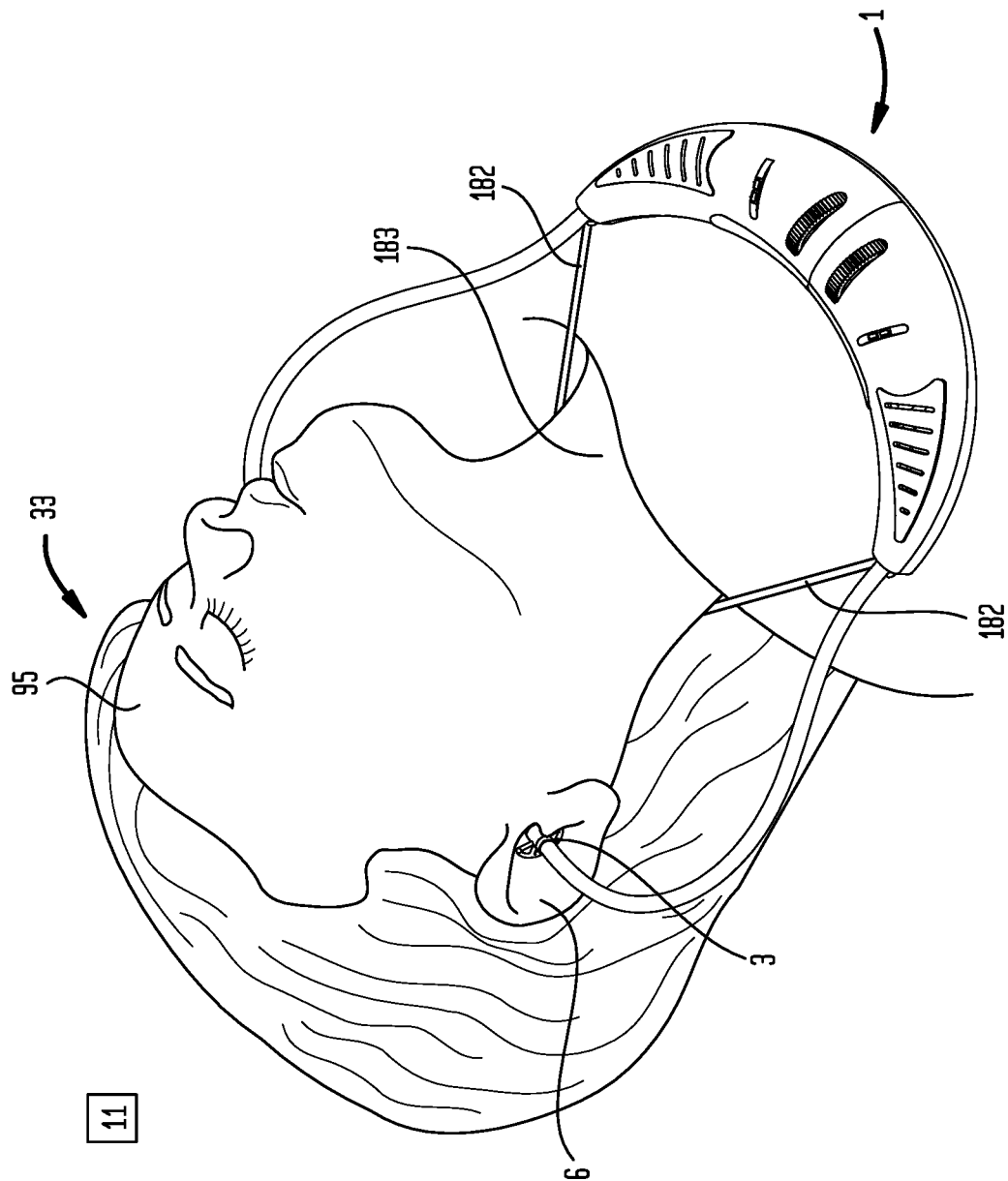
FIG. 3 is an illustration of a method of using a particular embodiment of the external ear canal pressure regulation device.

Now referring primarily to FIG. 1 and FIG. 2, particular embodiments can further include a computer device (151) discrete from the external ear canal pressure regulation device (1). The term "computer device (151)" means for the purpose of this invention any device adapted to receive the computer code (132) or receive a machine readable medium (152) containing the computer code (132), or includes a computer processor (153) in communication with a computer memory element (154) adapted to communicate with the external ear canal pressure regulation device (1), or downloads the computer code (132) through a wide area network (155), such as the Internet (156), or one or more local area networks (157) into a computer memory element (154) in communication with the computer processor (153). The computer device (151) can, as to particular embodiments, take the form of a limited-capability computer designed specifically for receiving the machine readable medium (152) in the form of a computer memory element (154) containing the computer code (132); however, other embodiments can take the form of set-top boxes, intelligent televisions connected to receive data through an entertainment medium such as a cable television network or a digital satellite broadcast, hand-held devices such as smart phones, slate or pad computers, personal digital assistants or camera/cell telephones, or multiprocessor systems, microprocessor-based or programmable consumer electronics, network personal computers, minicomputers, mainframe computers, or the like.

Again referring primarily to FIGS. 1 and 2, the computer device (151) can encompass one computer device or a plurality of computer devices, each of which can be operated by a user (33) to control one or a plurality of external ear canal pressure regulation devices (1). The user (33) can be a person, a plurality of persons, a business entity, or otherwise, can access to the computer device (151) to retrieve in a common format for display the graphic user interface (149) on computer graphical display surface (147).

As to particular embodiments, the controller (128) of the external ear canal pressure regulation device (1) can further include a communication controller (158) which can include a transceiver (159) associated with an antenna (160) to send and receive communication signals (161) to and from the computer device (151). As to particular embodiments the communication controller (158) can be a BLUETOOTH controller (for example a Texas Instruments CC2540 BLUETOOTH System-on-Chip) including the associated BLUETOOTH transceiver and BLUETOOTH antenna. As to particular embodiments, the communication controller (158) can be a Wi-Fi controller and the associated Wi-Fi receiver and Wi-Fi antenna.

Figure 36A:
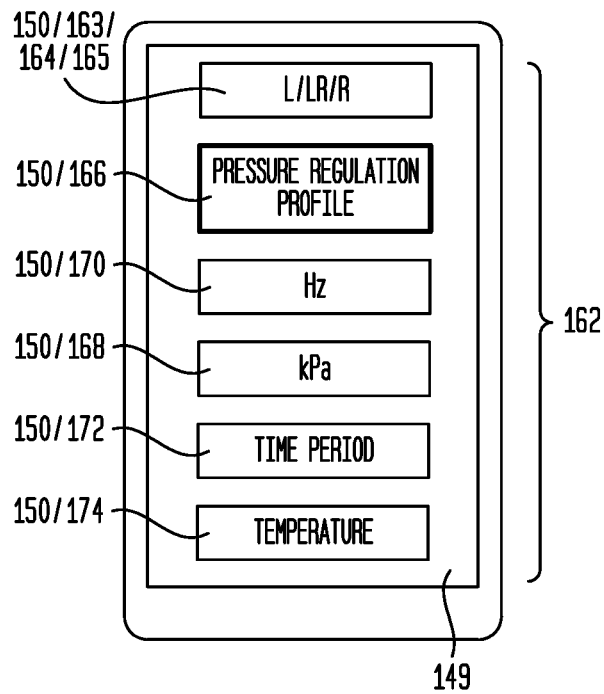
FIG. 36A is an illustration of a particular embodiment of a graphical user interface depicted on the display surface of a computer device and a method of using the graphical user interface to control operation of embodiments of the external ear canal pressure regulation device.
Figure 36B:
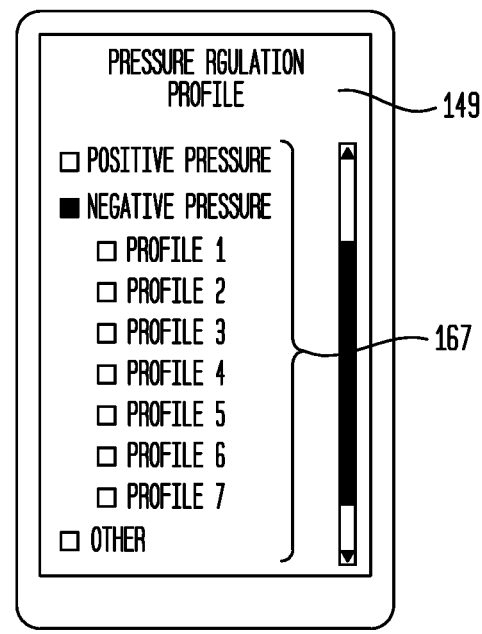
FIG. 36B is an illustration of a particular embodiment of the graphical user interface depicted on the display surface of a computer device and a method of using the graphical user interface to control operation of embodiments of the external ear canal pressure regulation device.

Now referring primarily to FIGS. 36A and 36B, an illustrative example of a graphical user interface (149) can include a mode selection list (162) which by user interaction allows selection of one or a plurality of: a first ear control image (163), a second ear control image (164), or both a first and second ear control image (165) which by user interaction selects administration of a first fluid flow (8) or a second fluid flow (20) or both a first and second fluid flow (8)(20) to the corresponding first and second axial earpiece conduits (4)(13); a pressure regulation profile control image (166) which by user interaction causes depiction of a list of selectable pressure regulation profile icons (167)(as shown in the example of FIG. 36B) which by user interaction allows selection of one of a plurality of pressure regulation profiles (136) to be administered, an external ear canal pressure differential amplitude control image (168) which by user interaction causes depiction of a list of selectable pressure differential amplitude control images which by user interaction allows selection of a pre-selected pressure differential amplitude (37), an external ear canal pressure differential frequency control image (170) which by user interaction causes depiction of a list of selectable pressure differential amplitude oscillation frequency control images which by user interaction allows selection of an pre-selected pressure differential amplitude oscillation frequency (49), a time period control image (172) which by user interaction causes depiction of a list of selectable time period control images which by user interaction allows selection of a time period (39) for administration or treatment, or a temperature regulation control icon (174) which by user interaction causes depiction of a list of selectable fluid flow temperatures and temperature-regulated flow rates which by user interaction selects administration of a fluid flow temperature (79) at a fluid flow rate (83).

Now referring primarily to FIGS. 8 and 28, embodiments of the external ear canal pressure regulation device (1) can further include a power source (177) which can be one or a combination of a transformed power (178) such as 110 volt alternating current transformed to 12 volt direct current or a power cell (179) such as a 12 volt direct current battery.

A method of producing particular embodiments of the external ear canal pressure regulation device (1) can include providing a first fluid flow generator (2) capable of generating a first fluid flow (8); and providing a first earpiece (3) having a first axial earpiece conduit (4) which communicates between a first earpiece first end (92) and a first earpiece second end (93). The first axial earpiece conduit (4) can be capable of fluidicly coupling to the first fluid flow generator (2). The first earpiece (3) can have a first compliant earpiece external surface (7) configured to sealably engage a first external ear canal (5) of a first ear (6) as a first barrier (102) between a first external ear canal pressure (10) and an ambient pressure (11).

The method of producing particular embodiments of the external ear canal pressure regulation device (1) can further include providing additional components of the external ear canal pressure regulation device (1) as above described.

As can be easily understood from the foregoing, the basic concepts of the present invention may be embodied in a variety of ways. The invention involves numerous and varied embodiments of an external ear canal pressure regulation device and methods for making and using such external ear canal pressure regulation devices including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "fluid flow" should be understood to encompass disclosure of the act of "flowing fluid"—whether explicitly discussed or not—and, conversely, were there effectively disclosure of the act of "flowing fluid", such a disclosure should be understood to encompass disclosure of a "fluid flow" and even a "means for flowing fluid." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the external ear canal pressure regulation devices herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A method for treatment of a symptom of a neurological disorder, the method comprising:
providing an earpiece that is configured to engage a first external ear canal of a first ear of a user;
configuring a fluid flow generator to generate a second fluid flow between the earpiece and the first external ear canal based on an effect on the symptom of the neurological disorder from a first fluid flow to either the first external ear canal or a second external ear canal of a second ear of the user, the first fluid flow being prior to generation of the second fluid flow; and
using the fluid flow generator to generate the second fluid flow between the earpiece and the first external ear canal.

2. The method of claim 1, further comprising providing a user interface that includes a symptom ranking element that enables the user to enter a symptom rank value for the symptom of the neurological disorder after the first fluid flow.

3. The method of claim 2, wherein the user interface is on a controller device that is discrete from a fluid transfer device.

4. The method of claim 3, wherein the controller device is configured to communicate wirelessly with the fluid transfer device.

5. The method of claim 1, further comprising providing a graphical user interface configured to display a symptom ranking element prior to or subsequent to generation of the second fluid flow.

6. The method of claim 1, further comprising providing a graphical user interface configured to receive user input of a first symptom rank value for the symptom of the neurological disorder prior to generation of the first fluid flow and to receive user input of a second symptom rank value for the symptom of the neurological disorder subsequent to generation of the first fluid flow.

7. The method of claim 1, wherein the symptom of the neurological disorder is pain.

8. The method of claim 1, wherein the neurological disorder is a migraine headache.

9. The method of claim 1, wherein the second fluid flow is effective to treat the symptom of the neurological disorder.

10. The method of claim 1, wherein the symptom is a headache.

11. The method of claim 1, wherein the neurological disorder comprises tinnitus.

12. The method of claim 1, further comprising: configuring the fluid flow generator to generate the second fluid flow based on the effect on the symptom of the neurological disorder from the first fluid flow in the first external ear canal.

13. The method of claim 1, further comprising: configuring the fluid flow generator to generate the second fluid flow based on the effect on the symptom of the neurological disorder from the first fluid flow in the second external ear canal.

14. The method of claim 1, wherein the second fluid flow is configured to create a negative pressure differential in the first external ear canal versus an ambient pressure outside the first external ear canal.

15. The method of claim 14, wherein:
the fluid flow generator is configured to generate the second fluid flow based on the effect on the symptom of the neurological disorder from the first fluid flow in the second external ear canal; and
the first fluid flow is configured to create a negative pressure differential in the second external ear canal versus the ambient pressure.

16. The method of claim 14, wherein:
the fluid flow generator is configured to generate the second fluid flow based on the effect on the symptom of the neurological disorder from the first fluid flow in the second external ear canal; and
the first fluid flow is configured to create a positive pressure differential in the second external ear canal versus the ambient pressure.

17. The method of claim 1, wherein the second fluid flow is configured to create a positive pressure differential in the first external ear canal versus an ambient pressure outside the first external ear canal.

18. The method of claim 17, wherein:
the fluid flow generator is configured to generate the second fluid flow based on the effect on the symptom of the neurological disorder from the first fluid flow in the second external ear canal; and
the first fluid flow is configured to create a negative pressure differential in the second external ear canal versus the ambient pressure.

19. The method of claim 17, wherein:
the fluid flow generator is configured to generate the second fluid flow based on the effect on the symptom of the neurological disorder from the first fluid flow in the second external ear canal; and
the first fluid flow is configured to create a positive pressure differential in the second external ear canal versus the ambient pressure.

20. The method of claim 1, wherein the second fluid flow is configured to create both a negative pressure differential and a positive pressure differential, at different respective times, in the first external ear canal versus an ambient pressure outside of the first external ear canal.

21. The method of claim 1, wherein the neurological disorder comprises anxiety.

22. The method of claim 1, wherein the neurological disorder comprises seizure.

23. The method of claim 1, wherein the neurological disorder comprises vertigo.

24. The method of claim 1, wherein the neurological disorder comprises an inner ear disorder.

25. The method of claim 1, wherein the neurological disorder comprises a middle ear disorder.

26. The method of claim 1, further comprising using a controller to control the fluid flow generator to generate the second fluid flow based on the effect on the symptom of the neurological disorder from the first fluid flow.

27. An external ear canal pressure system, comprising:
    an earpiece being configured to engage a first external ear canal of a first ear of a user;
    a fluid flow generator that is configured to generate a fluid flow between the earpiece and the first external ear canal to adjust a pressure in the first external ear canal;
    a controller configured to operate the fluid flow generator to:
        produce a first pressure differential in the first external ear canal; and
        produce a second pressure differential in the first external ear canal or a second external ear canal of a second ear of the user; and
    a user interface that includes a symptom ranking element that enables the user to enter a first symptom rank value for a symptom of a neurological disorder prior to the first pressure differential and to enter a second symptom rank value for the symptom of the neurological disorder subsequent to the first pressure differential;
    wherein the second pressure differential is based at least in part on an effect of the first pressure differential on the symptom of the neurological disorder.

28. The external ear canal pressure system of claim 27, wherein the user interface is on a controller device that is discrete from a device containing the fluid flow generator.

29. The external ear canal pressure system of claim 28, wherein the controller device is configured to communicate wirelessly with the device containing the fluid flow generator.

30. The system of claim 27, wherein the user interface is further configured to display the symptom ranking element prior to or subsequent to generation of the second pressure differential.

31. The system of claim 27, wherein the symptom of the neurological disorder is pain.

32. The system of claim 27, wherein the second pressure differential is effective to treat the symptom of the neurological disorder.

33. The system of claim 27, wherein the symptom is a headache.

34. The system of claim 27, wherein the second pressure differential is based on the effect on the symptom of the neurological disorder from the first pressure differential in the first external ear canal.

35. The system of claim 27, wherein the second pressure differential comprises a negative pressure differential in the first external ear canal versus an ambient pressure outside the first external ear canal.

36. The system of claim 35, wherein:
    the second pressure differential is based on the effect on the symptom of the neurological disorder from the first pressure differential in the second external ear canal; and
    the first pressure differential comprises a negative pressure differential in the second external ear canal versus the ambient pressure.

37. The system of claim 35 wherein:
    the second pressure differential is based on the effect on the symptom of the neurological disorder from the first pressure differential in the second external ear canal; and
    the first pressure differential comprises a positive pressure differential in the second external ear canal versus the ambient pressure.

38. The system of claim 27, wherein the second pressure differential comprises a positive pressure differential in the first external ear canal versus an ambient pressure outside the first external ear canal.

39. The system of claim 27, wherein the second pressure differential comprises at least one of a negative pressure differential and a positive pressure differential, at different respective times, in the first external ear canal versus an ambient pressure outside of the first external ear canal.

40. The system of claim 27, wherein the neurological disorder is a migraine.

41. The system of claim 27, wherein the neurological disorder comprises tinnitus.

42. The system of claim 27, wherein the neurological disorder comprises anxiety.

43. The system of claim 27, wherein the neurological disorder comprises seizure.

44. The system of claim 27, wherein the neurological disorder comprises vertigo.

45. The system of claim 27, wherein the neurological disorder comprises an inner ear disorder.

46. The system of claim 27, wherein the neurological disorder comprises a middle ear disorder.

47. A fluid transfer system for treatment of a symptom of a neurological disorder, the fluid transfer system comprising:
    a fluid flow generator that is configured to generate a first fluid flow and a second fluid flow, the first fluid flow being between an earpiece and an external ear canal, and the second fluid flow being between the earpiece and the external ear canal and based on an effect on the symptom of the neurological disorder of the first fluid flow; and
    a graphical user interface that is configured to receive a user input of a first symptom rank value for the symptom of the neurological disorder prior to generation of the first fluid flow and to receive user input of a second symptom rank value for the symptom of the neurological disorder subsequent to generation of the first fluid flow.

48. The fluid transfer system of claim 47, wherein the fluid flow generator is on a first device and wherein the graphical user interface is displayed on a second device that is discrete from the first device.

49. The fluid transfer system of claim 48, wherein the second device is a smart phone.

50. The fluid transfer system of claim 48, wherein the second device is configured to communicate wirelessly with the first device.

51. The fluid transfer system of claim 47, wherein the graphical user interface is configured to display a symptom ranking element that enables the user to enter the symptom rank value prior to or subsequent to generation of the second fluid flow.

52. The fluid transfer system of claim 47, wherein the symptom of the neurological disorder is pain.

53. The fluid transfer system of claim 47, wherein the second fluid flow is effective to treat the symptom of the neurological disorder.

54. The fluid transfer system of claim 47, wherein the symptom is a headache.

55. The fluid transfer system of claim 47, wherein the fluid flow generator is configured to generate the second fluid flow based on the effect on the symptom of the neurological disorder from the first fluid flow in the external ear canal.

56. The fluid transfer system of claim 47, wherein the fluid flow is configured to create a negative pressure differential in the external ear canal versus an ambient pressure outside the external ear canal.

57. The fluid transfer system of claim 56, wherein:
the fluid flow generator is configured to generate the second fluid flow based on the effect on the symptom of the neurological disorder from the first fluid flow in the external ear canal; and
the first fluid flow is configured to create a negative pressure differential in the external ear canal versus the ambient pressure.

58. The fluid transfer system of claim 56, wherein:
the fluid flow generator is configured to generate the second fluid flow based on the effect on the symptom of the neurological disorder from the first fluid flow in the external ear canal; and
the first fluid flow is configured to create a positive pressure differential in the external ear canal versus the ambient pressure.

59. The fluid transfer system of claim 47, wherein the second fluid flow is configured to create a positive pressure differential in the external ear canal versus an ambient pressure outside the external ear canal.

60. The fluid transfer system of claim 47, wherein the second fluid flow is configured to create both a negative pressure differential and a positive pressure differential, at different respective times, in the external ear canal versus an ambient pressure outside of the external ear canal.

61. The fluid transfer system of claim 47, wherein the neurological disorder is a migraine.

62. The fluid transfer system of claim 47, wherein the neurological disorder comprises tinnitus.

63. The fluid transfer system of claim 47, wherein the neurological disorder comprises anxiety.

64. The fluid transfer system of claim 47, wherein the neurological disorder comprises seizure.

65. The fluid transfer system of claim 47, wherein the neurological disorder comprises vertigo.

66. The fluid transfer system of claim 47, wherein the neurological disorder comprises an inner ear disorder.

67. The fluid transfer system of claim 47, wherein the neurological disorder comprises a middle ear disorder.

68. The system of claim 47, further comprising a controller configured to control the fluid flow generator to generate the first fluid flow and the second fluid flow.

* * * * *